United States Patent
Amano et al.

[11] Patent Number: 5,941,837
[45] Date of Patent: Aug. 24, 1999

[54] HEALTH MANAGEMENT DEVICE AND EXERCISE SUPPORT DEVICE

[75] Inventors: Kazuhiko Amano, Suwa; Kazuo Uebaba, Yokohama; Hitoshi Ishiyama, Toride, all of Japan

[73] Assignee: Seiko Epson Corporation, Tokyo, Japan

[21] Appl. No.: 08/894,457

[22] PCT Filed: Dec. 18, 1996

[86] PCT No.: PCT/JP96/03674

§ 371 Date: Oct. 14, 1997

§ 102(e) Date: Oct. 14, 1997

[87] PCT Pub. No.: WO97/22295

PCT Pub. Date: Jun. 26, 1997

[30] Foreign Application Priority Data

Dec. 18, 1995 [JP] Japan .................................. 7-329232
Mar. 12, 1996 [JP] Japan .................................. 8-55115

[51] Int. Cl.⁶ .................................................. A61B 5/00
[52] U.S. Cl. ............................................. 600/595; 600/503
[58] Field of Search .................................. 600/502, 503, 600/587, 595

[56] References Cited

U.S. PATENT DOCUMENTS

| | | | |
|---|---|---|---|
| 4,432,374 | 2/1984 | Osani | 128/694 |
| 5,479,939 | 1/1996 | Ogino | 128/782 |

FOREIGN PATENT DOCUMENTS

| | | |
|---|---|---|
| 57-93036 | 6/1982 | Japan . |
| 63-212327 | 9/1988 | Japan . |
| 2-3927 | 1/1990 | Japan . |
| 2-55035 | 2/1990 | Japan . |
| 6-105829 | 4/1994 | Japan . |
| 7-88092 | 4/1995 | Japan . |
| 7-213499 | 8/1995 | Japan . |
| 8-10234 | 1/1996 | Japan . |

*Primary Examiner*—Max Hindenburg
*Attorney, Agent, or Firm*—Eric B. Janofsky

[57] ABSTRACT

A health management device is provided, which enables the user himself to make a determination of the quality of his state of health, without the presence of a physician or nurse specialist. However, this device may of course be employed to receive measurement directives from, or provide notification to, a third party. Pulse sensor 4 measures the user's fingertip pulse wave. Acceleration sensor calculates an acceleration value from the user's body. These outputs are converted to digital signals at sensor interface 6. CPU1 determines whether or not the user is exercising based on the acceleration value read out from sensor interface 6. Based on this result, CPU1 takes up the user's pulse waves before and after exercise, and determines the acceleration pulse wave. CPU1 then calculates the amplitude ratio of inflection points included in the acceleration pulse waveform, evaluates the exercise performed by the user based on the pre-exercise and post-exercise amplitude ratios, and displays this result on display device 7.

21 Claims, 27 Drawing Sheets

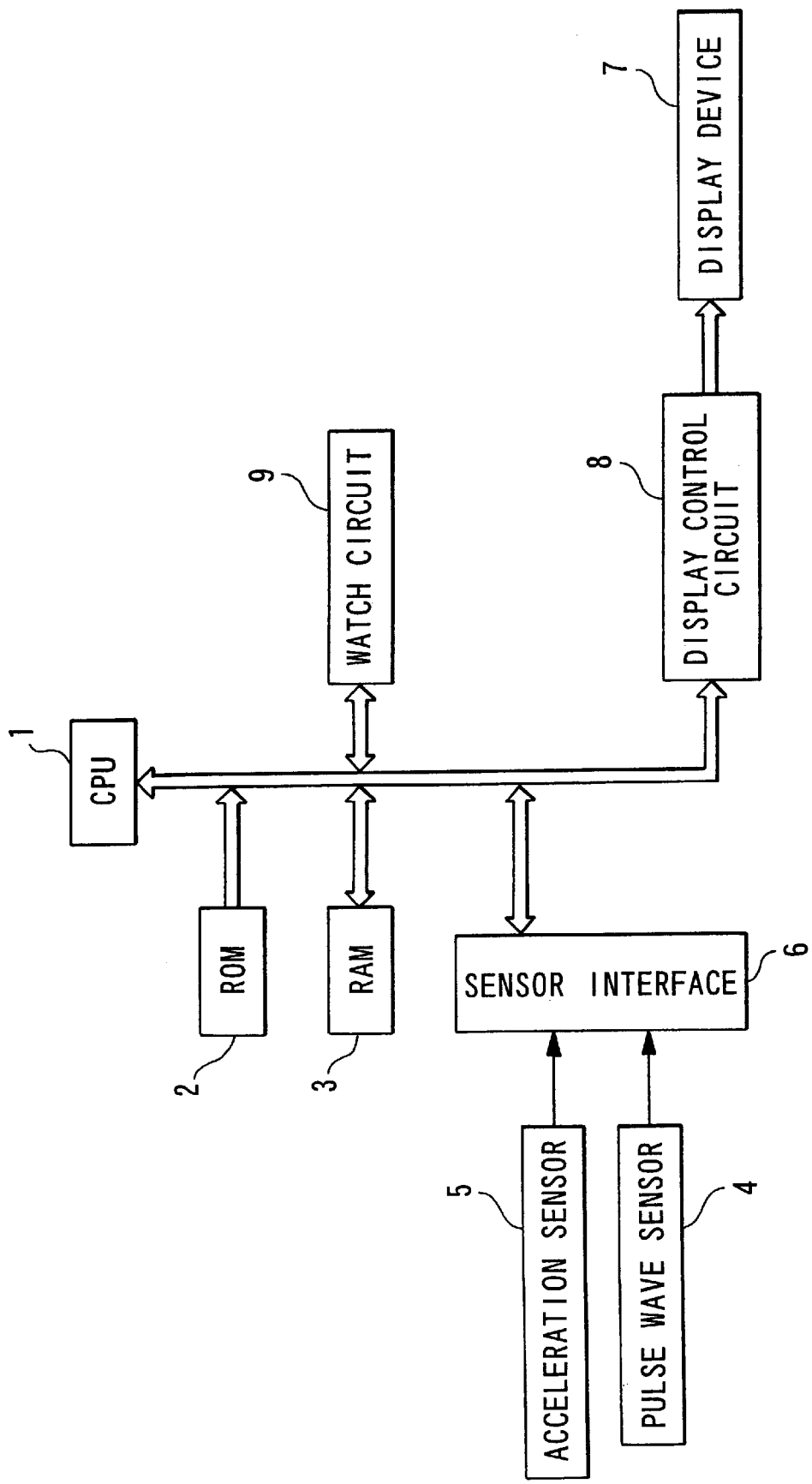

| | ① | ② | ③ | ④ | ⑤ | ⑥ |
|---|---|---|---|---|---|---|
| $\frac{d}{a}$ | WITHIN 10% | 10~35% | 35~60% | 60~100% | 60~100% | 60~100% |
| $\frac{c}{a}$ | WITHIN -10% | 10~15% | WITHIN -15% | 0~20% | 20~40% | OVER 40% |

FIG. 13
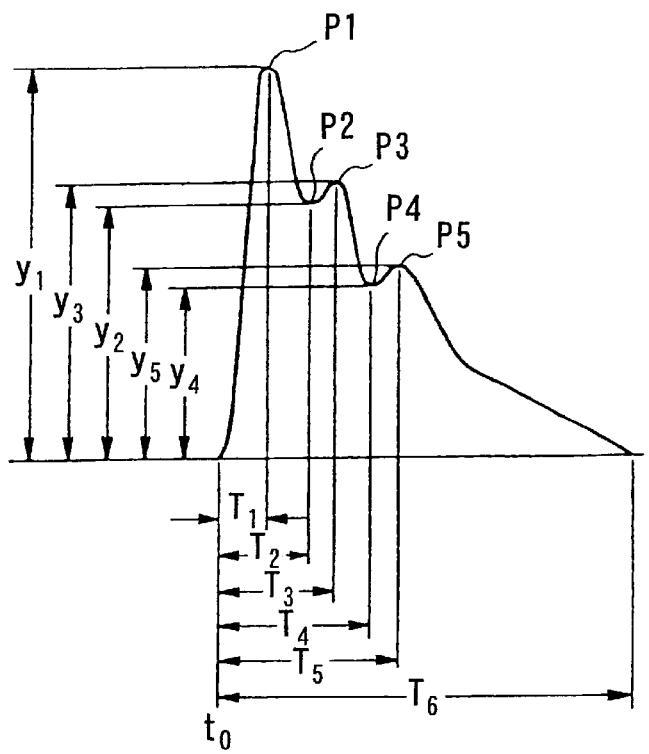
FIG. 14A
PRIOR ART
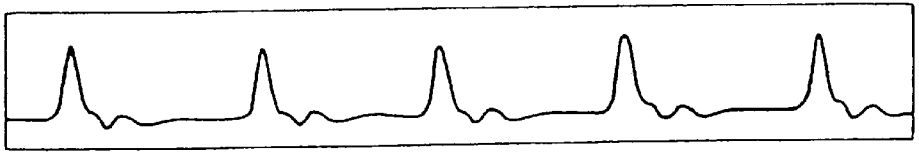
FIG. 14B
PRIOR ART
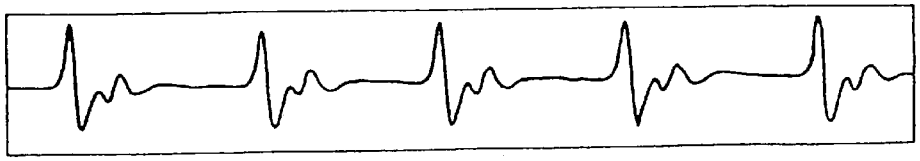
FIG. 14C
PRIOR ART

FIG. 20

TARGET VALUE FOR MAXIMAL OXYGEN UPTAKE (ml/kg/min)

|        | 20~29 | 30~39 | 40~49 | 50~59 | 60~69 |
|--------|-------|-------|-------|-------|-------|
| MALE   | 41    | 40    | 39    | 38    | 37    |
| FEMALE | 35    | 34    | 33    | 32    | 31    |

FIG. 21

REQUIRED AMOUNT OF EXERCISE TO CREATE A STATE OF HEALTH

| AGE | 20~29 | 30~39 | 40~49 | 50~59 | 60~69 |
|-----|-------|-------|-------|-------|-------|
| TOTAL NUMBER OF MINUTES OF EXERCISE PER WEEK | 180min | 170min | 160min | 150min | 140min |
| TARGET HEART RATE (beats/min) | 130 | 125 | 120 | 115 | 110 |

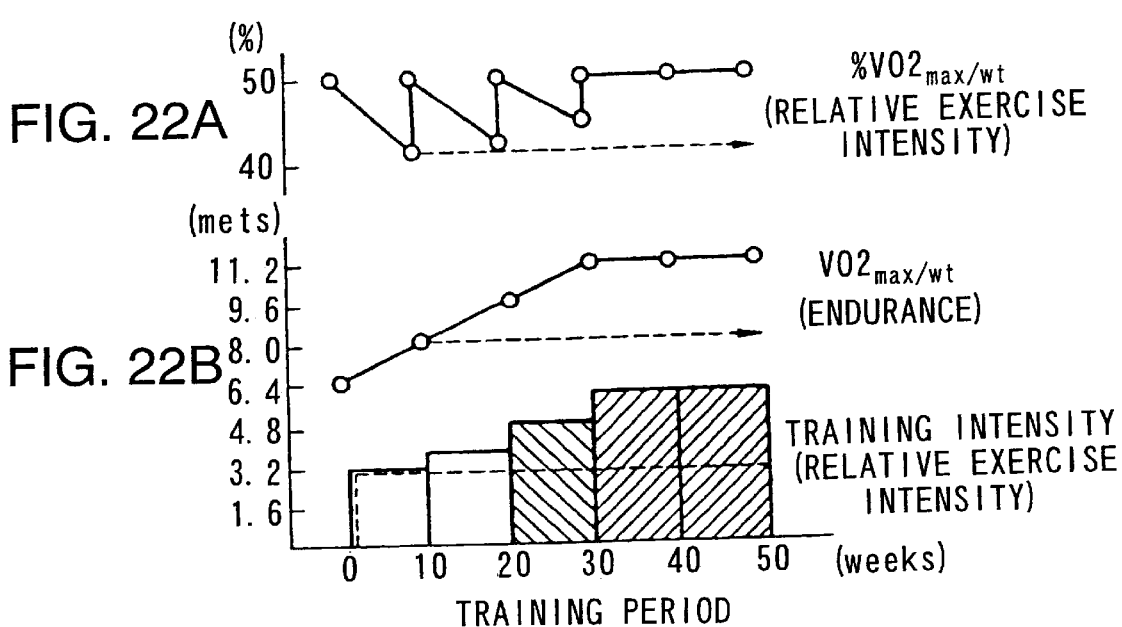
FIG. 22A
FIG. 22B
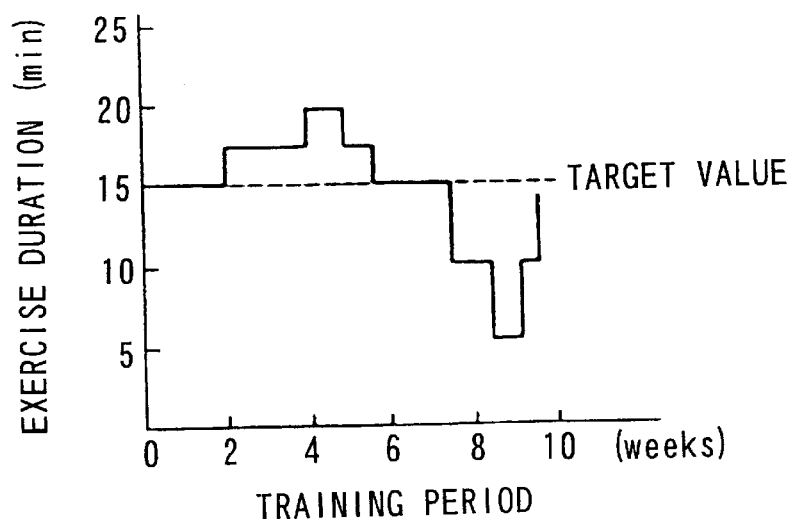
FIG. 23

HEALTH MANAGEMENT DEVICE AND EXERCISE SUPPORT DEVICE

BACKGROUND OF THE INVENTION

1. Technical Field

The present invention relates to a device for measuring physical state in a patient based on the condition of circulation. More specifically, the present invention relates to a health management device for monitoring the user's state of health based on information obtained from the condition of circulation in the user's body, and to an exercise support device which provides appropriate suggestions and guidance to the user, or provides an exercise plan deemed appropriate to create a state of health in the user.

2. Background of the Invention

With the rapid aging of society in recent years, the health issues of middle aged and elderly persons, geriatric diseases being chief among these, have been a topic of much discussion. Various factors have been cited as causes of such diseases. As one example of these factors, evidence has been found which suggests that insufficient circulation can cause health problems. When circulation is insufficient, cells and tissues do not receive the necessary amount of oxygen and nutrients. When this situation persists for a long period of time, organic pathological changes begin to occur in organs and tissues. Once these changes have progressed to a certain extent, symptoms can appear quite suddenly.

Accordingly, various attempts have been made to prevent such diseases before there is significant progression in organic pathological change, by determining the quality of circulation, the basis for these pathological changes. Accordingly, it has been the practice until now to determine the quality of circulation by focusing on risk factors such as blood pressure, changes in the electrocardiogram, blood cholesterol, neutral fat concentration, and the like.

However, in reality, it is not uncommon for cerebral apoplexy or heart failure to occur even in an individual with low blood pressure, while there are examples of elderly persons who have high blood pressure but still are in good health. Similarly, there are numerous instances where a substantial organic pathological change has occurred, but nothing is observed in the electrocardiogram, etc. While examination equipment may discover this change if it progresses further, this is not acceptable because of the additional delay.

Accordingly, the discovery that acceleration pulse waveforms can be useful as an indicator of the quality of circulation has gained attention in recent years. A brief explanation of acceleration pulse wave as a measure of circulation will now be provided. Namely, as is well known, circulation basically involves the heart pumping out blood, which flows through the arteries to the capillaries of the tissues and organs, and then returns through the veins.

The supply of oxygen and nutrients takes place at the capillaries, so that the quality of circulation is correlated to the behavior of the blood in the smallest vessels. Accordingly, transitions in the amount of blood contained in the capillaries may be viewed to serve as a good measure of circulation. Namely, a slight difference in arterial and venal blood pressure give rise to fine differences in nutrient supply and gas exchange at the capillary level. It is for this reason that it is believed that organic pathological changes may occur in tissues and organs if the difference in arterial and venal blood pressure expands over a long period of time.

Accordingly, one widely used method for observing changes over time in the amount of blood contained in the capillaries is the examination of the fingertip plethysmogram. However, the fingertip plethysmogram itself displays a gently undulating waveform. Accordingly, it was considered difficult to interpret very fine changes in the waveform. Further, there has also been the problem that changes in circulation are very small, and are sensitive to changes in the organism s environment.

However, if the second derivative of the fingertip plethysmogram waveform is obtained, to convert the waveform to a double differential plethysmogram (i.e., the acceleration plethysmogram waveform), it then becomes possible to enlarge and extract the information on circulation, and to display the circulation condition in a form which is easy to understand. FIG. 14($a$) is one example of the original waveform obtained at the fingertip plethysmogram; FIG. 14($b$) shows the waveform of the velocity plethysmogram obtained by taking the first derivative of the waveform shown in FIG. 14($a$); FIG. 14($c$) shows the waveform of the acceleration plethysmogram obtained by taking the second derivative of the waveform shown in FIG. 14($a$).

FIG. 15 shows an example in which one waveform of a typical acceleration plethysmogram has been extracted. As shown in this figure, there are three peaks and two valleys in one waveform of an acceleration plethysmogram. Namely, there is an initial peak a, followed by valley b, peak c, valley d, and peak e. The waveform is roughly flat from peak e until the next peak a. Further, if peak a is excluded, then each point does not form a peak or valley, but rather simply becomes a point of inflection.

The significance of the amplitudes of each of the aforementioned peaks and valleys will now be described. To begin with, peak a is a signal that the blood pumped out from the heart has reached the capillaries in the fingertip. Valley b relates to the heart's stroke volume. The larger the stroke volume the deeper valley b falls.

Peak c is related to venal return, and, from the view of circulation, indicates whether or not there is excessive pooling of blood by appropriate contraction of venules. When the venal return is good, peak c is near or above the base line. In contrast, when blood pooling in venules is increasing, peak c ceases to rise, but rather falls below valley b.

Valley d is related to the load on the heart. When the load on the heart is increasing, valley d falls sharply. Peak e corresponds to the position of the rise in the fingertip plethysmogram after a contraction, however the concrete significance of this is not yet understood.

It is known that poor circulation as ascertained from acceleration plethysmograms as described above can be improved by jogging or other forms of endurance training. A temporary improvement may be noted from just a single training session, while a sustained improvement can be confirmed if training is continued. On the other hand, if training is suspended, circulation again deteriorates. Accordingly, it is possible to know the degree of improvement in circulation by analyzing the acceleration plethysmogram.

Japanese Patent Application First Publication No. Hei 8-10234 (Title: Device for Measuring Exercise Quantity) may be cited as one example of a technology which applies the above-described acceleration plethysmograms in exercise. This reference cites the use of a treadmill or bicycle ergometer for performing exercise to increase the health of the patient, with the exercise's effect on the patient measured. For this purpose, information referred to as "waveform representative values", which are calculated from the acceleration plethysmogram waveform, are measured before and after exercise, and the difference in these waveform representative values is displayed. Further, during exercise, the waveform representative values at each point in time are compared to predetermined waveform representative values. When the difference in the measured and predetermined waveform representative values reaches a value which is the patient's load limit, for example, then exercise is halted.

Japanese Patent Application First Publication No. 57-93036 may be cited as one example of an invention which attempts to determine circulation quality in a patient by analyzing the acceleration plethysmograms. Various sites such as the fingertip, earlobe, and the like may be considered for measuring the plethysmogram. However, the aforementioned reference specifically measures the fingertip plethysmogram. This is because the movement of blood from the arteries to the veins can be obtained at the fingertip, and because this is the site where the capillaries are most developed and the amount of blood contained therein is great. Moreover, the fingertip is ordinarily exposed, so that it may be freely brought near the plethysmogram measurement device. Accordingly, this enables a more simplified structure for the device.

The structure of the acceleration plethysmograph according to the invention in the above-cited reference is shown in FIG. 16. This device is formed by means of the cascade connection of a fingertip plethysmogram pick-up 200, preamplifier 201, operational amplifier 202, characteristic extraction circuit 203 which has two analog differentiating circuits utilizing CR circuits, and an oscillograph 204. Fingertip plethysmogram pick-up 200 is comprised of an opening 206 into which the patient inserts his finger, a light source 207, and a photoelectric element 208.

Three types of plethysmogram waveform graphs are displayed on oscillograph 204:

the plethysmogram waveform, and the first and second derivative waveforms of the plethysmogram which are calculated by characteristic extraction circuit 203. Accordingly, based on the acceleration plethysmograms shown on oscillograph 204, it is possible to determine the quality of circulation in the patient.

To begin with, as a first method for this determination, the acceleration plethysmogram waveform is typed according to the depths of valleys b and d into three categories: valley b>valley d, valley b≈valley d, or valley b<valley d. Next, the thus-type patterns are further typed into three categories based on the height of peak c relative to the base line. The measured acceleration plethysmogram waveform is then set to whichever of these patterns it most closely resembles.

A second method of determination makes use of the height of peak c and the depth of peak d from the base line. As shown in FIG. 17, the depth of valley b is divided into four equal parts, for example, with the each partitioned area assigned a number 0, 1, . . . 5, in order from the base line. The number of points corresponding to the height of peak c, the depth of peak d, etc., are then determined from the positions thereof. In this way, the quality of circulation in the patient can be rendered as a numeric value.

This reference provides several working examples, including: 1) a device wherein, in place of a CR circuit, the measured value of the plethysmogram is digitalized using an A/D converter, and the acceleration plethysmogram is calculated by means of digital processing using a microcomputer; 2) a device wherein the third derivative waveform is obtained by taking the derivative of the acceleration plethysmogram waveform, and a microcomputer is used to obtain the position of the valleys and peaks; and 3) a device which corrects for fluctuations in the time interval of the plethysmogram due to respiratory action, by carrying out statistical processing, such as obtaining the arithmetic average for pairs of corresponding peaks and valleys, on the repeating waveform of a plurality of individual plethysmograms.

Japanese Patent Application First Publication No.: Hei 2-55035 discloses an invention which develops the above-described technology. The structure of the acceleration plethysmograph according to this reference is shown in FIG. 18. As shown in this figure, plethysmogram detector 300 includes a lamp 301 which is provided opposite the center of a concavity into which the fingertip is inserted, and a light detector comprising a photoelectric element 302. Photoelectric element 302 is formed of resistors 303 to 306 and a bridge circuit. The output from this bridge circuit is amplified by differential amplifier 307. Further, the brightness of lamp 301 can be adjusted with a switch S so that the bridge circuit is balanced. In this figure, the symbol V is the voltage of the electric source.

The output of differential amplifier 307 is amplified further by amplifier 308. Waveform correcting circuit 309 then modifies the amplified output to a rectangular waveform by clipping voltages which exceed a prefixed standard voltage. This output is differentiated at differentiating circuit 310, with micropulses generated in the negative direction by rectifier 311 to trigger one-shot multivibrator 312. As a result, a rectangular wave of duration $T_0$ is obtained in the output of one-shot multivibrator 312.

In addition, the output of differential amplifier 307 passes through gate circuit 313 during an interval of the aforementioned duration $T_0$. The output signal of gate circuit 313 passes through differentiating circuits 314, 315, with the output of the second derivative of the plethysmogram signal obtained in the output of differential circuit 315. Waveform correcting circuit 316 generates a sampling pulse for the output at each point in time where a valley b, peak c, and valley d appear. In accordance with this sampling pulse, sampling circuit 317 samples the output from differential circuit 315, which has passed through delay circuit 318, and stores the result in successive recording circuit 319. Maximum value detection circuit 320 reads out the contents of successive recording circuit 319, and records the maximum value from among the amplitudes for valley b, peak c, and valley d. The output of maximum value detection circuit 320 is divided at voltage dividing circuit 321, with each divided voltage then output.

Control circuit 322 successively outputs the voltages of valley b, peak c, and valley d, which are the output of successive recording circuit 319. This output is input into pulse height analyzer 323 which employs the output value of the voltage dividing circuit 321 as a comparison voltage, and, based on the voltages of valley b, peak c, and valley d, outputs values in which these voltages have been standardized (for example, ratios c/b, d/b, or ratios b/a, c/a, d/a, etc.) to output terminal OP.

A microcomputer or similar device determines which waveform pattern from among the pre-typed acceleration plethysmogram waveforms the waveform output at output terminal OP is associated with, and displays this result.

When making this determination of the waveform pattern, a determination is first made as to which of the voltage zones classified by voltage dividing circuit 321, the levels of standardized valley b, peak c, and valley d are associated with. For each of the separate voltage zones with which valley b, peak c, and valley d are associated, the measured plethysmogram is typed as one of the aforementioned patterns, based on the respective size relationship, and on the vertical relationship with respect to the base line of valley b, peak c, and valley d, to make a determination of the quality of circulation.

As explained above, maintaining good circulation is necessary to create a state of health. One important factor to accomplishing this is performing the appropriate level of exercise, to maintain a good circulation state for as long a period as possible. However, use of devices such as disclosed in the above-cited references present a problem.

Namely, it is known to be extremely difficult to accurately measure plethysmogram waveforms during exercise. Accordingly, using acceleration plethysmograms measured during exercise as a basis for controlling the exercise performed by a patient is not very successful, so that, as a result, the goal of carrying out the appropriate level of exercise is not achieved. Moreover, the present inventors carried out experiments using devices having the structures disclosed in the aforementioned references, and confirmed that plethysmograms could not be correctly measured. The same conclusion was reached even in the case where a sensor was attached to a patient's hand and the hand was held in place while the subject exercised on a tread mill, for example.

In devices such as those described above, information extracted from the acceleration plethysmogram is simply displayed to the patient. Thus, a doctor or nurse with special training is required to interpret these results. However, if numerous patients are exercising each day, and doctors and nurses must analyze the results and then direct the next exercise plan for each patient, then this creates a considerable burden on hospital personnel, and does not benefit the patient's treatment.

However, it is extremely troublesome and inconvenient for the user of the device himself to make a determination of the quality of circulation, without the assistance of a doctor or nurse. Moreover, there is no assurance that a patient exercising without a doctor present will be able to perform exercise of the same quality as would have been carried out if a doctor were present to provide guidance. Accordingly, when carrying out interval training or physical rehabilitation, various problems may occur, such as the exercise proving ineffective because it was too mild, or the exercise having an effect opposite that desired because it was overly strenuous.

On the other hand, guidance could be provided to the patient once every two or three weeks, but this is bothersome since it necessitates a visit to the doctor's office. Moreover, exercise of the same quality as if regular guidance were being provided still may not be carried out in this case. Accordingly, there have been grave doubts that effective exercise guidance could be carried out in the case where conventional devices were employed.

SUMMARY OF THE INVENTION

The present invention was conceived in consideration of the aforementioned circumstances, and has as its first objective the provision of a device for accurately measuring conditions in a patient based on the circulation state and body movement.

It is a second objective of the present invention to provide a health management device which monitors the user's state of health based on the state of circulation which is obtained from pulse waveforms, and provides appropriate suggestions and guidance to the user, this device moreover being easy to use.

It is a third objective of the present invention to provide a health management device which has a simple structure and which can proscribe an exercise plan deemed appropriate for creating a state of health in the user after taking the user's physical condition into consideration.

In order to achieve the above-stated objectives, the present invention is characterized in the provision of a pulse wave measuring means which measures the user's pulse waves, and a body movement measuring means which measurers the movement of the user's body.

As one preferred embodiment, the present invention composes a pulse wave measuring means for measuring the user's pulse waves, a body movement measuring means which measures the user's body movement, a calculating means which obtains an indicator showing the state of circulation in the user from the pulse waveform when the measured results of the body movement measuring means are below a prespecified value, and a notifying means which notifies the user of the aforementioned indicator.

More specifically, this embodiment composes a pulse wave measuring means for measuring the user's pulse waveforms, a pulse wave measurement directive detection means which detects a directive by the user to measure pulse waves, a calculating means which obtains an indicator showing the state of circulation in the user from the pulse waveform during the time that a plethysmogram measurement directive is being output, and a notifying means which notifies the user of the aforementioned indicator.

The aforementioned calculating means obtains the acceleration plethysmogram pulse waveform, selects two peaks and valleys from among the plurality of peaks and valleys appearing in the acceleration plethysmogram, obtains an amplitude ratio for the selected peaks and valleys, and defines this ratio as the aforementioned indicator.

In this embodiment, notification of the state of circulation is provided to the user based on the measurement of his pulse waves. Accordingly it is possible for the user to know the state of his own circulation at all times, with the exception of during exercise. Thus, advanced notice of such diseases as ischemic heart disease or cerebrovascular disease can be obtained.

The following four arrangements may be considered for the aforementioned calculating means.

(1) The aforementioned indicator is defined as the value obtained by dividing the amplitude value of the second valley by the amplitude value of the first peak in the acceleration pulse waves.

In this arrangement, the amplitude value of the spectral component obtained from a spectral analysis of change across the time period of adjacent pulse waves is defined as the indicator. As a result, it is possible to ascertain and manage the state of health based on an indicator which well displays the activity of the sympathetic and parasympathetic nervous systems.

(2) The time interval between adjacent pulse waves is calculated, spectral analysis is conducted on change over this time interval, and the amplitude value of the spectral component which is obtained from this analysis is defined as the aforementioned indicator.

In this arrangement, the ratio of the amplitudes of the low frequency and high frequency spectral components which are obtained from spectral analysis on changes over the time interval between adjacent pulse waves is defined as the indicator. Therefore, variation in the indicator which arises due to differences between individuals can be eliminated. Thus, in addition to managing the state of health, it is possible to provide objective data for determination.

(3) The time interval between adjacent pulse waves is calculated, spectral analysis is conducted on change over this time interval, the ratio of the amplitude of the low frequency spectral component and the high frequency spectral component obtained from this analysis is calculated, and defined as the indicator.

In this arrangement, the number of times the amount of change in the time interval between adjacent pulse waves exceeds a prespecified time is set as the indicator. Thus, health state can be ascertained and managed based on a indicator which well expresses conditions of arousal or sedation in the body.

(4) The time interval between adjacent pulse waves is calculated, and the number of time in which the amount of change in continuous time intervals exceeds a prespecified time is defined as the indicator.

In another embodiment, the health management device has a pulse measurement means for measuring the pulse rate of the user. When the measured result of the body movement measuring means exceeds a prespecified value, the notifying means notifies the user of the measured pulse rate.

This health management device is provided with an evaluation means which measures an indicator when the measured result of the body movement measuring means is below a prespecified value, and measures the indicator again after the measured result of the body movement measuring means exceeds the prespecified value and then again returns below that prespecified value. The evaluation means then carries out an evaluation of the exercise performed by the user based on the difference in these indicators. Thereafter, the notifying means notifies the user of the results of this evaluation.

In this embodiment, the user is informed of his pulse rate while he is exercising. Thus, even during exercise, it is possible to adjust the amount of exercise appropriately, so that a more desirable training effect can be achieved.

In another embodiment, a pulse measuring means for measuring the user's pulse rate, and a pulse measurement directive detection means, for detecting a directive from the user to measure pulse rate, are provided. As a result, the notifying means notifies the user of the pulse rate measurement result during the time that a pulse measurement directive is being output.

In this embodiment, an evaluation means is provided which takes up the indicator obtained when the user issued a pulse measurement directive prior to the start of exercise, and the indicator obtained when the user issued a pulse measurement directive after the completion of exercise, and then carries out an evaluation of the exercise performed by the user based on the difference in these indicator values. Thereafter, the notifying means notifies the user of the results of this evaluation.

Since the exercise evaluation is made based on the change in the indicator before and after exercise, it is possible to know whether the exercise carried out at each interval in interval training, for example, is overly strenuous, too mild or just right. Thus, it is possible to carry out more effective training.

When measuring the pulse waves or pulse rate based on a directive from the user, it is not necessary to provide a means for detecting whether or not the user's body is moving. Accordingly, the structure of the device can be simplified.

Another embodiment is characterized in the provision of a body movement measuring means, which measures the user's body movement, and a body movement detection means, which detects that the measured result of body movement has exceeded a prespecified value. This embodiment is further characterized in that the notifying means provides a warning to the user when the body movement measurement exceeds a prespecified value during the time that the pulse wave measurement directive is being output.

In this embodiment, the user's movement during the measurement of the pulse waves is monitored, and a warning is provided when movement in excess of a prespecified value is detected. Therefore, the user is informed when his movement presents a hindrance to the accurate measurement of the pulse waves, and is prompted to carry out the measurement of the pulse wave again.

In another embodiment, the exercise to be performed by the user consists of a plurality of stages. This embodiment is characterized in the provision of a recording means in which indicator target values which are to be reached at each stage of exercise are prestored at each stage of exercise; and a comparing means which compares the indicator calculated by the calculating means and the target value corresponding to each exercise stage, at the point in time when the user completes each exercise stage. When the results of this comparison indicate that the indicator calculated by the calculating means has reached the target value, the notifying means notifies the user to proceed to the next stage of exercise.

In this way, the user is directed to proceed to the next stage of exercise when the calculated indicator has reached the target value set for each exercise stage. As a result, when it is necessary to carry out exercise in an escalating manner, as in the case of physical rehabilitation, it is possible to carry out exercise appropriately even when unaccompanied by a doctor or nurse.

Another embodiment is characterized in the provision of a recording means which records indicators obtained at prespecified times and the moving average for indicators obtained over a past prespecified time interval; and a control means which reads out from the recording means past indicators which were obtained at the same clock time as the present time, calculates the moving average of the past indicator and the current indicator, stores this result in the recording means together with the current time, determines the difference between the moving average of the indicators obtained over a past prespecified time interval and the current indicator, and compares this difference to a prespecified value. If this difference exceeds the prespecified value, the notifying means provides a warning to the user.

Because the user is provided with a warning when the difference between the current indicator and the moving average for indicators obtained over a prespecified period of time in the past exceeds a prespecified value, it is possible to provide the user with rapid notification in the case where his health state as observed from circulation has worsened compared to its usual state. Thus, the user is able to make active efforts to maintain his health by promptly consulting with a medical professional.

Another embodiment is characterized in the provision of a device having a target setting means for setting the user's exercise target, a target correction means for correcting the target value based on the user's physical condition, and a first communications means; and a portable device having a notifying means for notifying the user, a measuring means for measuring the user's physical condition, and a second communicating means which can communicate in either direction with the first communications means. This embodiment is further characterized in that the target indicators and physical condition are sent and received by the first and second communications means.

In this way, the user is notified of the exercise target values which have been set, and the target values are corrected as necessary based on the physical condition obtained from the user. As a result, it is possible to change the exercise plan in response to an improvement in the user's physical condition or exercise capacity, and to realize the maintenance or improvement in physical condition without the presence of a doctor or specially trained nurse. Moreover, since the necessary information can be relayed between the two devices using the first and second communications means, processing which requires high speed calculations or large amounts of memory can be performed by a device which is provided external to the portable device. Thus, the portable device can have a simpler structure.

The target value mentioned here is at least one from among exercising pulse rate, exercise duration per session, and frequency of exercise.

In addition, this embodiment is also characterized in the provision of a pulse measuring means for measuring the user's pulse rate; and a guidance means which provides guidance to the user during the time that a pulse rate measurement directive is being received from the user, so that the pulse rate measured by the pulse measuring means is within prespecified limits which include the exercising pulse rate target value.

Since guidance is provided during the time that a pulse rate measurement directive is being received, so that the measured pulse rate is within prespecified limits which include the target value, overly intense or ineffective exercise is not carried out. Thus, it is possible to plan for the maintenance or improvement in health state by carrying out effective exercise.

Additionally, in this case, it is preferable that the target setting means set the initial target value based on age and sex information provided by the user.

In addition, the measuring means is provided with a pulse wave detection means which detects pulse wave in the user, with the measuring means then extracting the physical condition from these pulse waves.

Here, physical state is, for example, the amplitude value of the spectral component obtained from performing spectral analysis of change over the time interval between adjacent pulse wave.

Alternatively, the ratio of the amplitude value of the low frequency spectral component and the amplitude value of the high frequency spectral component obtained from spectral analysis of change over the time interval between adjacent pulse waves may also be used.

In this latter case, since the amplitude ratio of the low and high frequency spectral components obtained from spectral analysis of change over the time interval between adjacent pulse waves is employed as the physical state, it is possible to eliminate variation in the indicator which arises from individual differences, when prescribing an exercise plan.

In addition, the physical state may also be equated to the number of times that the amount of change over the time interval between adjacent pulse waves exceeds a prespecified time.

Moreover, an acceleration pulse wave calculating means may also be provided for calculating the pulse wave's acceleration pulse wave. In this case, the physical state is the amplitude ratio between two peaks or valleys which are selected from among the plurality of peaks and valleys appearing in an acceleration pulse wave.

Since this design equates the physical state with the amplitude ratio between two peaks or valleys selected from the plurality of peaks and valleys appearing in an acceleration pulse wave, it is possible to prescribe an exercise plan based on indicators which directly express the state of circulation.

Additionally, it is acceptable for the physical state to be the amplitude ratio obtained when the amplitude value of the second valley is divided by the amplitude value of the first peak appearing in the acceleration pulse wave.

Also, an exercise quantity calculating means may be provided for calculating the amount of exercise performed by the user. In this case, the target correction means evaluates changes in the user's state due to exercise, based on the quantity of exercise and the amplitude ratio, and then corrects the exercise target values based on the results of this evaluation.

In this design, since exercise is evaluated based on the quantity of exercise performed and the amplitude ratio obtained from the acceleration pulse waves, and correction is made to provide a new exercise target value, it is possible to prescribe a prescribe an exercise plan which takes into consideration the fact that the user's physical state as estimated from the amplitude ratio is dependent on the amount of exercise performed.

In another embodiment, the measurement means is provided with a sensor for measuring physical state. This embodiment is characterized in that a first connection member for attaching the sensor to the portable device, and a second connection member for attaching the second communication means to the portable device, are attached in a freely releasable manner to a connector which is provided to the portable device.

In this design, the connection members for respectively attaching the sensor and the second communication means to the portable device can be freely attached to and released from the connector which is provided to the portable device. Thus, the connector can be made compact, while the sensor and the second communication means can be used as necessary by connecting to the portable device.

Additionally, in the preceding embodiments, a means can be provided for newly setting the initial value of the exercise target value, based on the user's exercise capacity which is re-evaluated each time the user's performs exercise over a prespecified period of time.

As a result, since a new initial value is set for the exercise target value based on the user's exercise capacity which is re-evaluated each time he performs exercise over a prespecified period of time, it is possible to realize an optimal exercise plan which resembles the improvement in exercise capacity which occurs when the user is under the guidance of someone specialized in this area.

An example of the structure of the present invention is shown in FIG. 32. In this figure, 601 is a pulse wave measuring means which is realized, for example, by the pulse wave sensor 4 and sensor interface 6 shown in FIG. 1. 602 is a body movement measuring means which is realized, for example, by acceleration sensor 5 and sensor interface 6. 603 is a calculating means which is realized by CPU1, for example. 604 is a recording means which is realized by RAM3, for example. 605 is a control means and 606 is an evaluation means, these being realized by CPU1, for example. 608 is a notifying means which is realized by display device 7 and display control circuit 8. 607 is a pulse wave measurement directive detection means which is realized by the operational portion 506 shown in FIG. 19, for example.

BRIEF DESCRIPTION OF THE FIGURES

FIG. 1 is a block diagram showing the structure of the health management device according to one embodiment of the present invention.

FIG. 2(*a*) shows various arrangements of the acceleration plethysmogram of the fingertip plethysmogram.

FIGS. 12(a) through 12(c) show the original waveform of a typical pulse wave, wherein FIG. 12(a) is a normal wave, FIG. 12(b) is a smooth wave, and FIG. 12(c) is a violent wave.

FIG. 13 is a diagram for explaining the characteristics of the pulse waveform, over a single beat in the pulse wave.

FIGS. 14(a) through 14(c) show the waveform of the fingertip plethysmogram, wherein FIG. 14(a) is the measured original waveform, FIG. 14(b) is the velocity plethysmogram, and FIG. 14(c) is the acceleration plethysmogram.

FIG. 20 is a diagram showing the target value for the maximal oxygen uptake quantity.

FIG. 21 is a diagram showing the required amount of exercise necessary to create a state of health.

FIGS. 22(a) and 22(b) are diagrams showing how the maximal oxygen uptake quantity transitions together with duration of training, in the case where training is carried out at an exercise intensity corresponding to 50% of the maximal oxygen uptake quantity.

FIG. 23 is a diagram showing the slight adjustment in the exercise target value in response to the user's physical condition.

PREFERRED EMBODIMENTS OF THE PRESENT INVENTION

Basic Theory Employed in Preferred Embodiments

Various preferred embodiments of the present invention will now be explained with reference given to the accompanying figures.

To develop the basic theory of the preferred embodiments described below, we will first discuss the types of the acceleration pulse waveforms, followed by an explanation of the type of exercise which is preferable for creating a state of health.

(1) Types of acceleration pulse waveforms

Figures 2A, 2B:
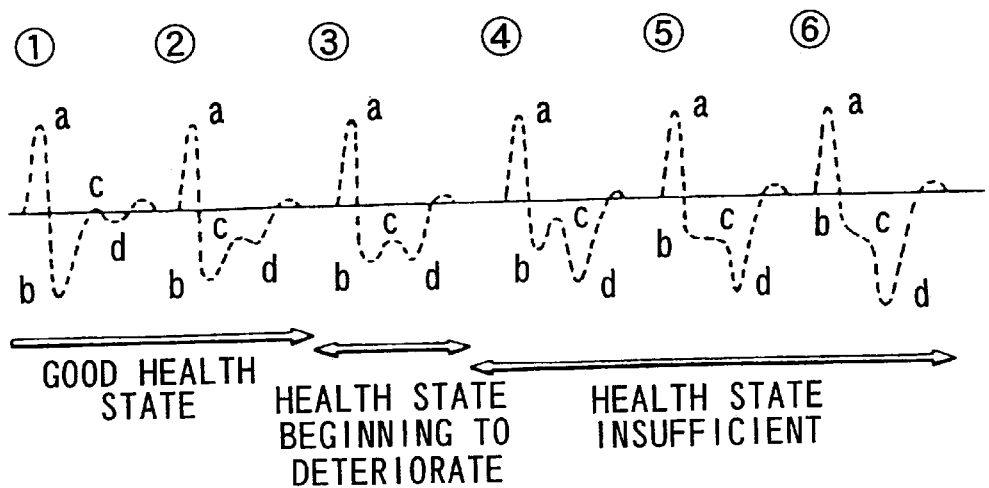
FIG. 2(b) shows the ranges for amplitude ratios d/a and c/a for each of the patterns in FIG. 2(b).

FIG. 2(a) shows acceleration pulse waveforms of a variety of types. When circulation is good, a waveform is observed in which valley b falls significantly with respect to peak a, peak c rises to around the base line, and valley d falls only a small amount (see ① or ② in figure). On the other hand, when circulation is insufficient, the load on the heart increases. In this case, valley b and valley d fall to about the same extent (see ③ in figure). When circulation is significantly poor, the waveform may deform to one in which valley d falls below valley b (see ④ in figure), one in which peak c is positioned about on par with valley b (see ⑤ in figure), or one in which peak c is lower than valley b (see ⑥ in figure).

As one standard for determining which of the patterns (1) through (6) in FIG. 2(a) is expressed by a measured acceleration pulse wave, an approach may be considered using the ratio of the amplitude of peak a and the amplitude of another peak or a valley.

In the case where employing the ratio of the amplitude of valley d to the amplitude of peak a, i.e., amplitude ratio d/a, as the standard, then a value for d/a of within 10% indicates pattern (1); 10–35% indicates pattern (2); 35–60% indicates pattern (3); and 60–100% indicates patterns (4) through (6).

On the other hand, when the ratio of the amplitude of peak c to the amplitude of peak a, i.e. amplitude ratio c/a, is employed as the standard, then a value for c/a of within −10% indicates pattern (1); 10–15% indicates pattern (2); within −15% indicates pattern (3); 0–20% indicates pattern (4); 20–40% indicates pattern (5); and above 40% indicates pattern (6). Since, the range for patterns (2) through (4) overlap, this approach may be used to categorize patterns (4) through (6) only, or may be used in combination with the value of the amplitude ratio d/a.

It should be noted that the amplitude ratio may be a negative value, indicating that peak c or valley d are located above the base line.

Taking the case of an individual user, the more closely the waveform of his acceleration pulse wave resembles the pattern (1) type waveform, the better the user's state of health. Conversely, the more closely the waveform of his acceleration pulse wave resembles a pattern (6) type waveform, the worse the state of his health tends to be. Accordingly, by observing the acceleration pulse waveform in this way, it becomes possible to estimate the user's state of health. For example, this may be considered useful for predicting the occurrence of ischemic heart disease (myocardial infarction, angina pectoris) or cerebrovascular disease (cerebral apoplexy, arachnoideal bleeding).

When the relationship between age and the acceleration pulse wave are examined, a trend is observed in which the acceleration pulse waveform shifts from pattern (1) through pattern (6) in accordance with advancing age. Thus, if the user's measured acceleration pulse waveform is compared to an acceleration pulse waveform which has been estimated based on the user's age, and a significant tendency toward pattern (6) is observed, then this may be presumed to indicate a sign of the diseases mentioned above.

(2) Exercise to create a state of health

An explanation will now be made of the type of exercise which is preferable for creating a state of health. Additionally, it is noted here that more intense exercise or a longer workout does not necessarily facilitate creating a state of health in the user. Indeed, excessive exercise can be harmful to health.

Accordingly, research has been carried out on the appropriate exercise for creating a state of health. In recent years it has become understood that an index referred to as the "maximal oxygen uptake quantity" can serve as a measure of the state of health, and serves an important function in setting the level of intensity in exercise. Maximal oxygen uptake quantity, which is defined as the maximum amount of oxygen which can be taken in one minute, can serve as an absolute index for evaluating an individual's exercise capacity. The value for the maximal oxygen uptake quantity is typically employed after converting to a per kilogram body weight value.

From the perspective of maintaining health, it is recommended to keep the maximal oxygen uptake quantity above a prespecified target value for health maintenance. Typically, this target value is determined based on sex and age, as shown in FIG. 20, for example (source: Research Related to Application Methods for Required Amount of Exercise and Measurement of Effects Thereof and Research Related to the Use of Exercise Duration, Intensity and Frequency to Create a State of Health, 1989, 1991, and 1992 subsidies for Public Welfare and Science Research No. 00209065, No. 00264886, No. 00464607; and Industry Committee to Research Development of Physical Health).

Aerobic exercise, which generates energy as oxygen is taken in through respiration during exercise is suitable for safely reaching and maintaining this maintenance target value. To maintain aerobic exercise, it is necessary to maintain exercise intensity below 70% of the maximal oxygen uptake quantity. There are various views on the appropriate level of exercise intensity. However, it is the present inventors' opinion that it is appropriate to set exercise intensity at 50% of the maximal oxygen uptake quantity.

The advantages for setting exercise intensity at this level may be enumerated as follows. First, this level of exercise is not hard and leaves the user psychological leeway while exercising. Second, this level is more appropriate to activation of fat metabolism as compared to more intense exercise. Third, an oxygen shortage to the heart is not likely to occur, so that this level of exercise is highly safe and free from the concern that blood pressure will rise to an extent which is dangerous. And fourth, at this level of exercise, there is almost no pain in the leg muscles and joints, and little generation of lactic acid, a metabolite of muscle fatigue, so that exercise can be continued for a long period of time.

When exercise intensity is set at 50% of the maximal oxygen uptake quantity, then the targeted amount of exercise, i.e., the desired amount of exercise needed to create a state of health, is as shown in FIG. 21. Taking as its subject an average individual in which the resting heart rate ($\approx$pulse rate) is about 70 beats/min., this figure shows the total number of minutes of exercise to be carried out in one week and the targeted heart rate. For example, if exercise in which the heart rate is maintained at 110 beats/min. is carried out for just 140 minutes per week, then the maximal oxygen uptake quantity reaches the targeted value of 37 ml/kg/min (male) or 31 ml/kg/min (female) for a person in their sixties (see FIG. 20). In addition, it may be understood from FIG. 21 that when exercise intensity is fixed at 50% of the maximal oxygen uptake quantity, then the achievable level of the maximal oxygen uptake quantity is directly proportional to the number of minutes of exercise per week.

With regard to the duration of each exercise session, in order for the body to respond to aerobic exercise, it is necessary to continue exercising for at least 10 minutes or more. Also, it is preferable to exercise a total of 20 minutes or more per day, and three or more times per week (but preferably every day).

To sum up, it is desirable to exercise at a suitable intensity and for the required number of minutes per week based on age and sex, to raise the maximal oxygen uptake quantity to the desired target value.

FIGS. 22(a)–22(c) show the transition in exercise intensity from training carried out under the standards described above (source: same as above). FIG. 22(a) shows the change in % $Vo_{2max}$/wt, where the training period is plotted on the horizontal axis and the % $Vo_{2max}$/wt value is plotted on the vertical axis. Here, % $Vo_{2max}$ is the maximal oxygen uptake quantity, and % $Vo_{2max}$ is the proportion of the oxygen uptake quantity at each point in time with respect to the maximal oxygen uptake quantity. % $Vo_{2max}$/wt is the value obtained when % $Vo_{2max}$ is converted to a per kilogram body weight value. FIG. 22(b) shows the change over time in the maximal oxygen uptake quantity per unit body weight $VO_{2max}$/wt and training intensity as a result of training. The training period is plotted on the horizontal axis and the absolute exercise intensity is plotted on the vertical axis. The units for the vertical axis are mets (metabolic equivalents), which can be employed as a unit for absolute evaluation of energy metabolism. The patients were male, and exercise of an intensity corresponding to 50% of the maximal oxygen uptake quantity was carried out for 180 minutes per week.

As shown in FIG. 22(a), at week 0 when training began, the exercise intensity was set at 50%. As training at this intensity level accumulates, the individual's exercise capacity gradually increases. As a result, the value of % $Vo_{2max}$/wt rises as shown in FIG. 22(b). Accordingly, the exercise becomes easier for the individual, causing the pulse rate during exercise to fall. Namely, the relative exercise intensity over weeks 0 through 10 falls as shown in FIG. 22(a), so that by week 10 this value has reached 40%.

Therefore, in order to carry out a suitable level of training accompanying the improvement in exercise capacity, at week 10, 50% of the new maximal oxygen uptake quantity corresponding to the user's improved exercise capacity is reset as the exercise target value. Namely, as shown in FIG. 22(b), the training intensity is reset to a higher level. Subsequently, after each 10 week training period, the exercise target value is reset in response to the user's improved exercise capacity (maximal oxygen uptake quantity), with training then carried out at the new target level. Accordingly, % $\text{Vo}_{2max}$/wt changes along a zigzag pattern every $10^{th}$ week as shown in FIG. 22(a), while $\text{Vo}_{2max}$/wt increases as training progresses. However, there is a final limit to exercise capacity. Accordingly, at week 40 in FIG. 22(a), neither % $\text{Vo}_{2max}$/wt nor $\text{VO}_{2max}$/wt change from the values noted at week 30. From this point on then, training is continued at the intensity level set at week 30.

Accordingly, over the long-term, the present invention consists of a continuous cycle of:

1) prescribing an exercise target value
2) carrying out training over a prespecified period of time
3) evaluating exercise capacity due to training
4) setting a new target value based on the result of this evaluation In the case of (3) and (4) above, discussions may be carried out between doctor and patient, or coach and athlete, in each training period (10 weeks, for example), with the doctor or coach then reevaluating the patient's or athlete's exercise capacity, and resetting the target value.

The required amount of exercise as described above is a standard value based on an average person. In reality, the amount of exercise required for a given individual will vary depending on age, sex, degree of health, and other physiological conditions. In view of this, the present invention makes it possible to prescribe an exercise plan which takes into consideration individual differences and conditions by evaluating a person's state of health using physiological conditions obtained from the acceleration pulse wave and the like, and then adjusting the target value for exercise based on the results of this evaluation, so that the user is guided to perform exercise which is suitable to creating a state of health.

Namely, using FIGS. 22(a)–22(c) show as an example, as a general rule training is carried out for 10 weeks without receiving any guidance from a doctor or coach, so that exercise is carried out in accordance with the fixed target value indicated for that period. However, for the reasons just mentioned, fine adjustments are made in the time, intensity and frequency target values after taking into consideration the patient's or athlete's physical condition. Accordingly, from the short term perspective, every 10 weeks, for example, the device of the present invention carries out a continuous cycle of:

1) training according to a prescribed plan
2) evaluating the state of health as a result of training
3) fine adjustment of target values based on result of evaluation
4) prescribing (notifying) target values after fine adjustment Taking exercise duration as an example, the target value will change as shown in FIG. 23 in response to the quality of the individual's physical condition. This is also true for the case of exercise intensity and exercise frequency. Moreover, this fine adjustment is of course carried out weekly and daily, but may also be carried out any number of times when training is performed in a single day, for example, at each 15 or 20 minute training session, to finely adjust the next exercise target.

Embodiment 1

The structure of the health management device according to the present invention will now be explained. FIG. 1 is a block diagram showing the structure of this device. In this figure, CPU1 (central processing unit) is the central part which controls each circuit in the health management device. The function of CPU1 will be explained below under the section covering operation.

The control programs carried out by CPU1 and various control data and the like are stored in ROM2 (read-only memory). In addition, ROM2 also stores the target value for exercise duration, the values of the upper and lower limits for exercise intensity, and the target value for exercise intensity (average exercise intensity), for realizing desirable exercise corresponding to the pattern of the user's health state, i.e., amplitude ratio d/a, etc.

Random access memory RAM3 is employed as an operational area when CPU1 is carrying out operations (for example, the area for storing the total exercise amount while the user is exercising). In addition, RAM3 also stores the measured values and operational results from a variety of sensors which will be explained below.

Pulse wave sensor 4 is an optical pulse wave detection sensor which is attached to the user's first finger, for example. This pulse wave sensor 4 is composed of a light emitting diode and a light sensor employing a phototransistor or the like, for example. Light radiated from the light emitting diode is received by the light sensor after being reflected via the blood vessels under the skin, and undergoes photoelectric conversion, to obtain a pulse wave pulse wave detection signal as a result. Where consideration is given to the signal noise ratio, it is acceptable to employ a diode which emits blue light.

Acceleration sensor 5 is a body movement sensor which senses movement of the user's body. It may be attached to the same location, for example the finger, as pulse wave sensor 4.

Sensor interface 6 uptakes the output of pulse wave sensor 4 and acceleration sensor 5 at specified intervals, converts the analog signal taken up into a digital signal and outputs it.

Display device 7 displays a variety of information such as messages and the like to the user and may, for example, be a liquid crystal display provided to a wristwatch. Display control circuit 8 receives display information from CPU1, converts the display information to the format employed by display device 7, and carries out the display of the information on display device 7.

In addition to having the ordinary functions associated with a watch, watch circuit 9 also sends out an interrupt signal to CPU1 at clock times which have been preset by CPU1, or after the elapse of a time period which has been preset by CPU1.

A number of arrangements may be considered as a method for attaching a health management device to the body as a portable device. One example of these is described below, however, other arrangements with a variety of other portable devices are of course possible.

Figure 3A:
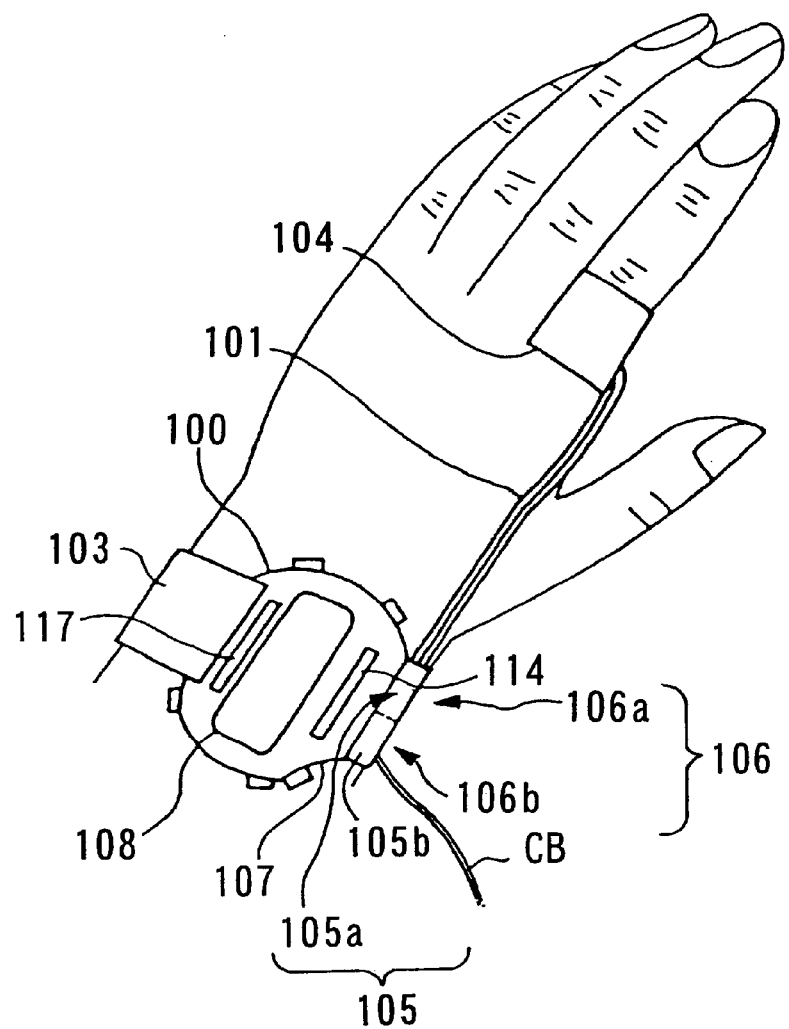
FIGS. 3(a) and 3(b) show the same device incorporated in a wristwatch.
Figure 3B:
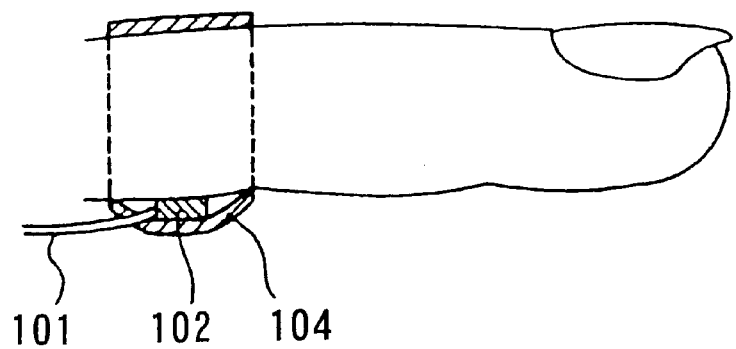

As a first arrangement, an embodiment may be proposed in which the health management device is incorporated into a wristwatch such as shown in FIGS. 3(a) and 3(b).

As shown in this figure, the health management device of this embodiment is formed of a device main body 100 having a wristwatch structure, a cable 101 connected to device main body 100, and a sensor unit 102 provide to the end of cable 101. A wristband 103 is attached to device main body 100 which wraps around the user's wrist from the 12 o'clock position and affixes at the 6 o'clock position of the wristwatch. Device main body 100 can be freely attached and removed from the user's wrist by means of this wristband 103.

Sensor unit 102 is blocked from light by band 104 employed for fixing the sensor in place, and is attached between the base and second joint of the user's index finger. By attaching sensor unit 102 in this way to the base of the finger, cable 101 can not only be made shorter, but will not present an interference to the user during exercise. Additionally, it is known that when the temperature distribution from the palm to the tip of the finger is measured, the temperature at the tip of the finger drops markedly in the case where the temperature of the surrounding environment is low, whereas the temperature at the base of the finger falls comparatively little. Accordingly, if sensor unit 102 is attached to the base of the finger, it is possible to accurately measure pulse rate and the like, even in the case where exercising outdoors during cold weather.

A connector 105 is provided at the 6 o'clock position on the face of the wristwatch. A connector piece 106, which is provided to the end of cable 101, is releasably attached to connector 105. By releasing connector piece 106 from connector 105, the device may be used as an ordinary wristwatch or stopwatch. Also, in order to protect connector 105, a specific connector cover is attached when cable 101 and sensor unit 102 are released from connector 105. With the exception of an electrode component, this connector cover may be formed of parts formed in the same way as connector piece 106.

As a result of a connector design as described above, connector 105 is disposed toward the user, facilitating its manipulation. In addition, since connector 105 does not extend out from device main body 100 in the 3 o'clock position, the user can freely move his wrist during exercise. Thus, even if the user falls during exercise, the back of the hand will not impact connector 105.

The other parts shown in FIG. 3 will now be explained in greater detail with reference given to FIG. 4.

Figure 4:
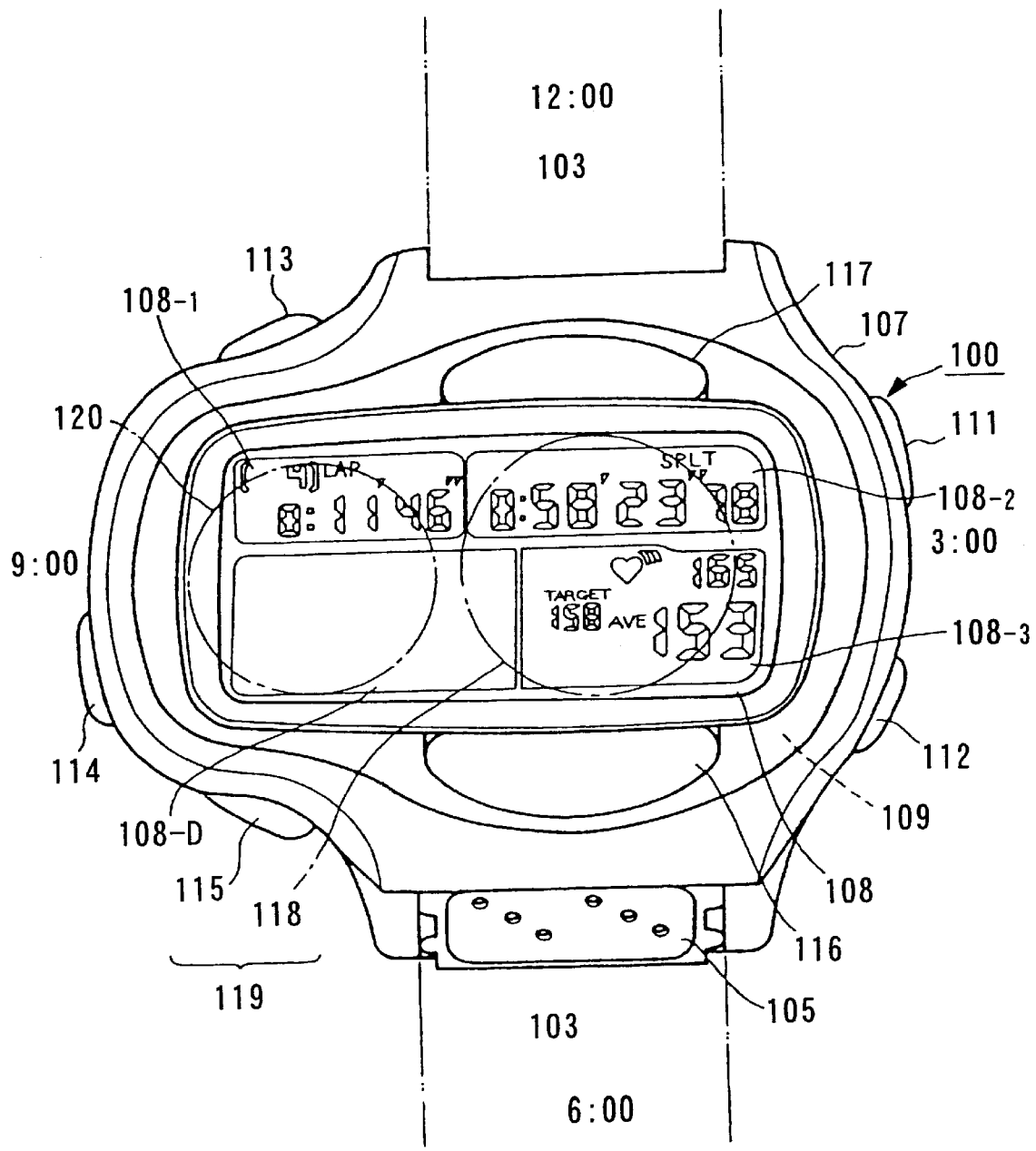
FIG. 4 is a level view showing the structure of the wristwatch in greater detail, in the case where the device is incorporated in a wristwatch.

FIG. 4 shows the device main body 100 of this embodiment in detail, with cable 101 and wristband 103 detached. In this figure, parts which are equivalent to those shown in FIGS. 3(*a*) and 3(*b*) have been assigned the same numeric symbol and an explanation thereof has been omitted.

In this figure, device main body 100 is provided with a watch case 107 made of a resin. A liquid crystal display 108 is provided to the face of watch case 107 which displays in digital form the current time and date, as well as pulse information such as pulse rate and the like. LCD device 108 is comprised of first, second, and third segment display regions 108-1, 108-2, and 108-3, respectively, and a dot display region 108-D. First segment display region 108-1 is positioned at the upper left area of the display panel; second segment display region 108-2 is positioned at the upper right area of the display panel; third segment display region 108-3 is positioned at the lower right area of the display panel; and dot display region 108-D is positioned at the lower left area of the display panel.

In this example, the date, day of the week and current time are displayed in first segment region 108-1, while the passage of time when carrying out various time measurements is displayed in second segment region 108-2. Pulse rate and the like measured during the measurement of pulse wave pulse waves are displayed in third segment region 108-3. Finally, various information can be graphically displayed in dot display region 108-D, in addition to a variety of other displays such as a mode display, which indicates which mode the device is in at a particular time, the pulse waveform's original waveform/velocity pulse waveform/ acceleration pulse waveform display, a bar graph display which shows change in the pulse rate over time, and the like.

The term "mode" as used here refers to a variety of modes such as a mode for using the device as a health management device, a mode for setting the time and date, a mode for using the device as a stop watch, and the like.

A controller 109 for carrying out signal processing for displaying changes in pulse rate or the like on LCD device 108 is housed inside watch case 107. Controller 109 includes a watch circuit for carrying out watch functions. Further, an ordinary clock time display may be used for LCD device 108, however, live time or split time displays for use when the device is operated as a stop watch are also possible.

Button switches 111–117 are provided to the outer periphery and surface of watch case 107.

When button switch 111, which is at the 2 o'clock position on the wristwatch, is pressed, an alarm is set to sound one hour thereafter.

Button switch 112, which is at the 4 o'clock position on the wristwatch, is provided for directing switching of the various modes the device has when functioning as an ordinary wristwatch.

When button switch 113, which is at the 11 o'clock position on the wristwatch, is pressed, an electroluminescence (EL) back light on liquid crystal display device 108 is turned on for 3 sec, for example, after which it automatically turns off.

Button switch 114, which is at the 8 o'clock position on the wristwatch, switches between the various graphic displays which are to be displayed on dot display region 108-D. By pressing button switch 115, which is at the 7 o'clock position on the wristwatch, the form of time and date display (i.e., time displayed in seconds/minutes/hours, 12 or 24 hour display, etc.) can be switched in the day and date correction mode.

Button switch 116, which is positioned below LCD display 108, can be used when correcting time or date, by decreasing the setting by one. Additionally, when timing a lap, button switch 116 can be used as a switch for informing CPU1 of the completion each lap. Button switch 117, which is positioned above LCD 108, is employed for indicating the initiation or termination of operation of the health management device. In addition to being used to increase the time and date setting by one, button switch 117 can also be used to indicate the initiation or termination of a variety of time elapse measurements.

A button-shaped battery 118 is housed in watch case 107 and serves as an power source for the device. Cable 101 shown in FIG. 3 supplies electric power from battery 118 to sensor unit 102, and sends the detection results from sensor unit 102 to controller 109.

It becomes necessary to enlarge device main body 100 as the functions of the watch itself are increased. Device main body 100 cannot be enlarged in the 6 or 12 o'clock directions, however, since a limitation on size is imposed because the watch must be worn on the arm. Therefore, in this embodiment, a horizontally long watch case 107 is employed which is longer in the horizontal, (i.e., 3 o'clock to 9 o'clock) direction, than in the vertical (i.e., 6 o'clock to 12 o'clock) direction.

In this embodiment, wrist band 103 is connected to a watch case 107 at a position shifted toward the 3 o'clock side of the watch. As seen from wrist band 103, a large overhang 119 is present on the 9 o'clock side the wristwatch, but is absent from the 3 o'clock side of the watch. Accordingly, the user can bend his wrist when using or carrying the horizontally long watch case 107. Further, even if the user falls, he will not hit the watch case with the back of his hand.

A flat piezo element 120 used as a buzzer is disposed inside the watch case 107, at the 9 o'clock position with respect to the battery 118. Battery 118 is heavier than piezo element 120, such that the position of the weight center of device main body 100 shifts toward the 3 o'clock side. Moreover, wrist band 103 is connected to the side of the main body 100 toward which the weight center has shifted. As a result, device main body 100 can be attached to the arm in a stable manner. Further, since battery 118 and piezo element 120 are disposed in the planar direction, device main body 100 may be made thinner. By providing a battery cover to the rear surface of the wristwatch, the user can easily change the battery.

The correspondence between the parts in FIG. 1 and those in FIGS. 3(*a*), 3(*b*) and 4 is as follows. The controller 109 in FIG. 4 is equivalent to CPU1, ROM2, RAM3, sensor interface 6, display control circuit 8 and watch circuit 9 in FIG. 1. Also, sensor unit 102 in FIGS. 3(*a*), 3(*b*) is equivalent to pulse wave sensor 4 and acceleration sensor 5 in FIG. 1, while the liquid crystal display 108 in FIGS. 3 and 4 is equivalent to display device 7 in FIG. 1.

Next, an explanation will be made of the operation of a health management device of the above design.

Before beginning to exercise, the user presses button switch 117 to activate the functioning of the device. As a result, the pulse waveform and the acceleration value are then sent to the sensor interface 6 from pulse wave sensor 4 and acceleration sensor 5, respectively, and converted to a digital signal. Meanwhile, CPU1 sends the pulse wave pulse waveform taken up to display control circuit 8, after which the pulse waveform is displayed on display device 7. As a result, the user can observe as a graphic display the pulse wave pulse waveform, which is changing over time, on the dot display area of 108-D of the liquid crystal display 108 shown in FIG. 4, for example.

CPU1 is designed to measure the resting pulse rate just once prior to the start of exercise after the user has pressed button switch 117. In this case, CPU1 determines whether or not the user is moving (i.e., whether or not the user is in a state or repose) according to whether or not the movement of pulse wave sensor 4 accompanying movement of the user is to an extent which will impair detection of the pulse wave. In other words, if the output value of acceleration sensor 5 exceeds a prespecified value (0.1 G, for example), then CPU1 determines that the user is moving (i.e., not in a state of repose). Since detection of the pulse wave cannot be accurately carried out in this case, CPU1 displays a message on display device 7 alerting the user not to move.

When the output value of acceleration sensor 5 is below a prespecified value, then CPU1 determines that the user is not moving (i.e., is in a state of repose). The pulse waveforms are then taken up for a prespecified period of time only from sensor interface 6, and stored in RAM3. The pulse waveforms taken up during this time period are then separated into wavelength units, and the number of wavelengths is counted. This is then converted to a per minute value to calculate the pulse rate. The thus calculated pulse rate is then stored in RAM3 as the resting pulse rate.

Figure 15:
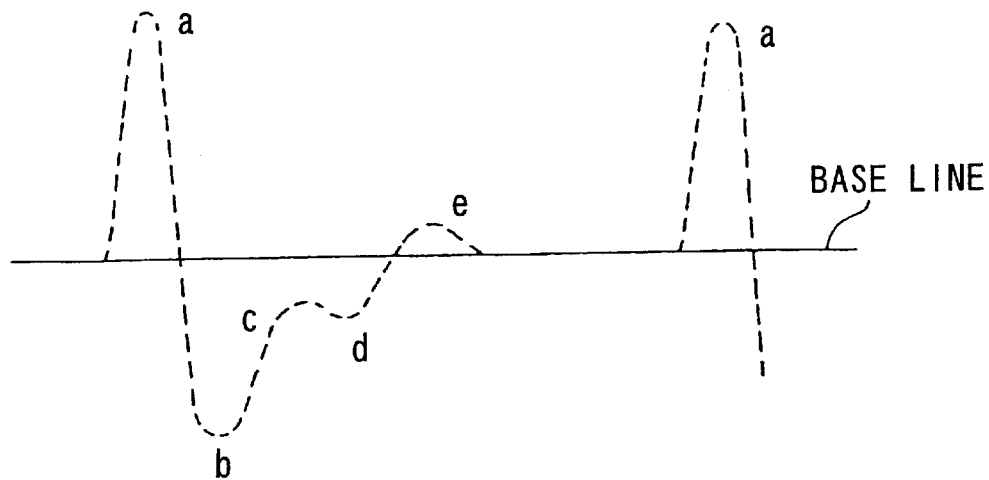
FIG. 15 shows the extraction of a portion of the waveform of the acceleration plethysmogram in the fingertip plethysmogram.
Figure 16:
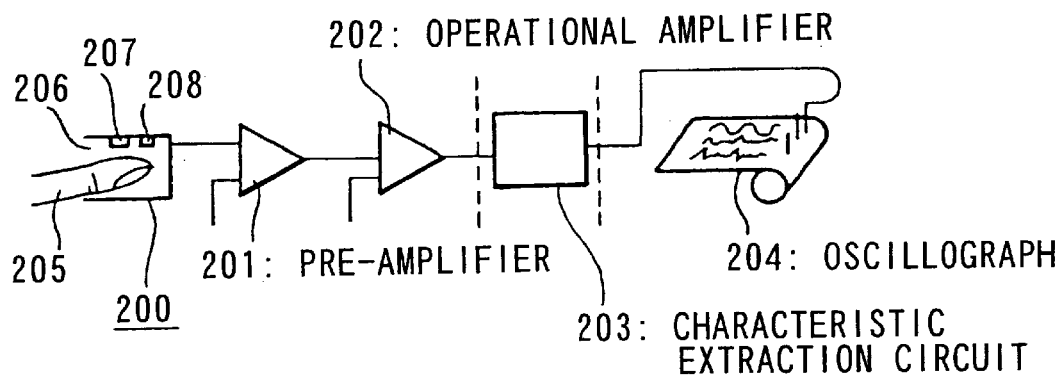
FIG. 16 is a block diagram showing the structure of a conventional acceleration plethysmograph.
Figure 17:
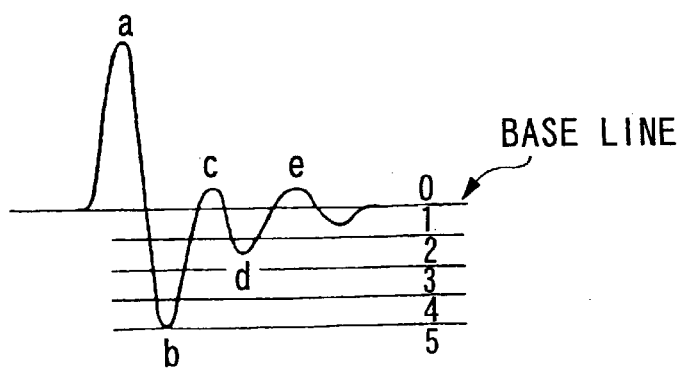
FIG. 17 shows the division of an acceleration plethysmogram waveform which is carried out when a measured acceleration plethysmogram is typed.
Figure 18:
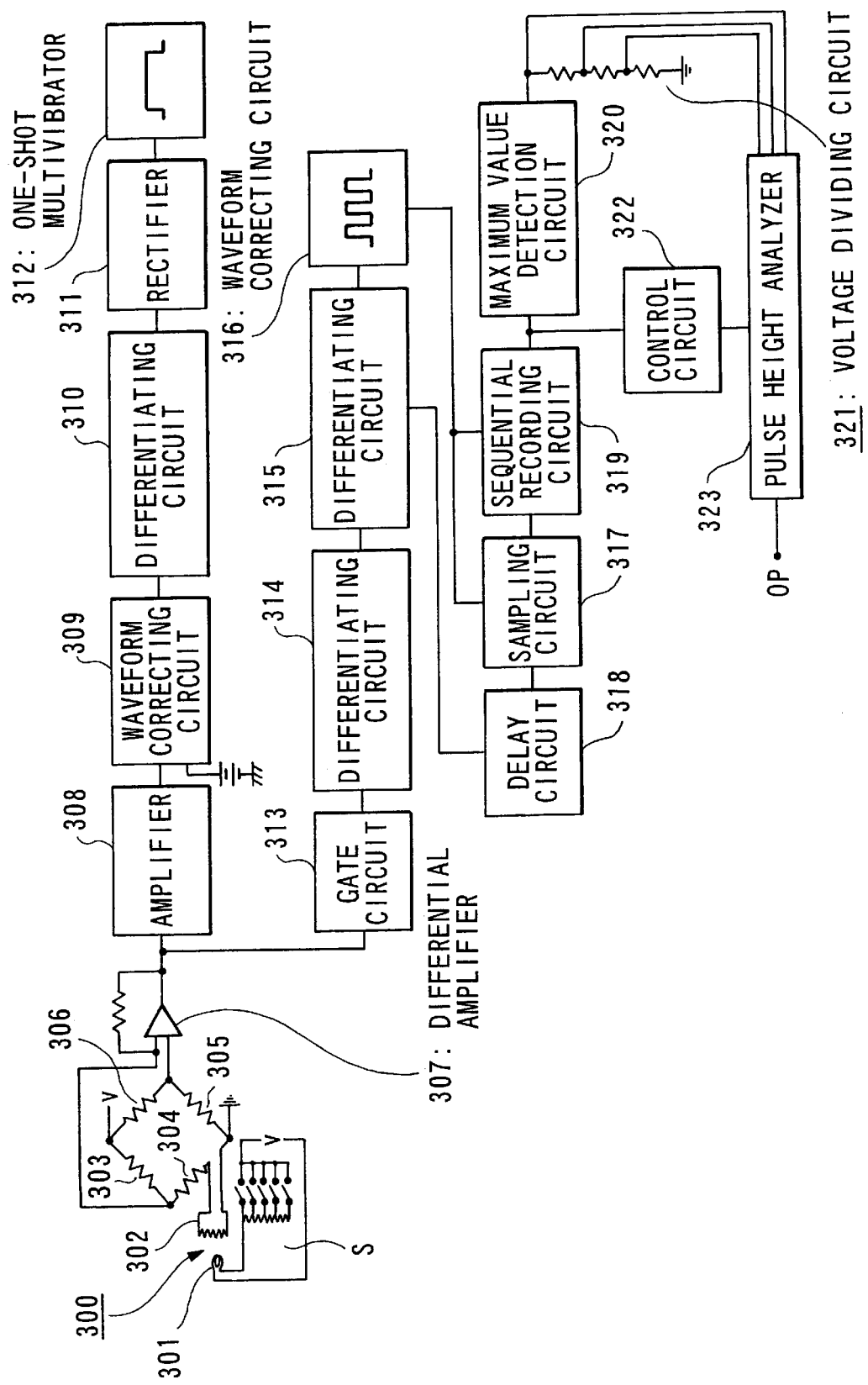
FIG. 18 is a block diagram showing the structure of another conventional acceleration plethysmograph.

CPU1 reads out a single wavelength segment from the pulse waveform stored in RAM3, and then differentiates this waveform twice with respect to time, to obtain an acceleration pulse waveform such as shown in FIG. 15. CPU1 then determines peak a, valley b, peak c and valley d by obtaining the inflection points of the acceleration pulse waveform. The value of the amplitude at each of these inflection points is then obtained. These inflection points can be obtained by the typical methods, such as by taking the time derivative of the acceleration pulse wave. The calculated acceleration pulse waveform, and the velocity pulse waveform which was obtained in the process of obtaining the acceleration pulse waveform, may be graphically displayed on display device 7.

Next, CPU1 calculates values in which each of the amplitude values of valley b, peak c and valley d are normalized by the amplitude value of peak a, i.e., the amplitude ratios b/a, c/a, and d/a, and stores the calculated results in RAM3. From among these, amplitude ratio d/a is most useful as an indicator which expresses the state of circulation. Therefore, as a general rule, the explanation of the embodiments of the present invention which follows hereinafter will employ just amplitude ratio d/a. Further, while strictly speaking, it is preferable to employ both amplitude ratios d/a and c/a, the following discussion of determination will employ only amplitude ratio d/a as the most convenient method.

Next, CPU1 guides the user as to what degree of exercise should be performed. First, CPU1 determines which pattern (1) through (6) is associated with the user's acceleration pulse waveform prior to exercise, based on the amplitude ratio d/a obtained as above and the table shown in FIG. 2(*b*). The pattern type is stored in RAM3 as the pattern of the user's acceleration pulse waveform prior to exercise, and is displayed on display device 7. However, it would be difficult for the user to interpret the significance if just the pattern type was displayed. Accordingly, if, for example, the pulse waveform is found to be a pattern (3) type waveform, then a supplementary message such as "health state beginning to deteriorate" is displayed on display device 7.

Next, the exercise intensity target value, the upper and lower limit values for exercise intensity, and the exercise duration target value corresponding to the obtained pulse wave pattern are read out from ROM2 and stored in RAM3, and displayed on display device 7 as target values for the user during exercise.

When the user starts to exercise, the output value from acceleration sensor 5 gradually increases as the movement of the body becomes more rigorous. When the output value of the acceleration sensor exceeds the aforementioned prespecified value at some point in time onward, CPU1 recognizes that the user has begun to exercise. CPU1 then reads out the clock time from watch circuit 9 and stores this as the exercise-start time in RAM3. At the same time, CPU1 sets watch circuit 9 to generate an interrupt signal when the targeted time for exercise duration has elapsed. Also, in order to calculate the total amount of exercise during the exercise session, CPU1 initializes the memory area provided in RAM3 at [0].

CPU1 then measures the user's pulse rate and exercise amount, and provides guidance as the user is exercising.

In order to accomplish this, CPU1 first reads out the pulse waveform from sensor interface 6 at prespecified time intervals, and calculates the user's pulse rate. This pulse rate is converted to display information, sent to display control circuit 8, and then displayed on display device 7.

CPU1 calculates the amount of exercise, which, in this case, is displayed in the form of calories. Since calories burned are approximated as the product of pulse rate and exercise duration, CPU1 multiplies the pulse rate obtained as described above by the time which has elapsed from the immediately preceding pulse rate measurement to the current pulse rate measurement. When calculating the exercise amount, it is typically the case that the immediately preceding pulse rate will differ from the current pulse rate. Therefore, it is acceptable to employ the average of the two values. CPU1 obtains the total exercise amount by adding the current exercise quantity to the total amount of exercise calculated through the immediately preceding pulse rate measurement. The total exercise amount since the beginning of the exercise session, and the exercise amount from the previous pulse rate measurement through the current pulse rate measurement, are stored in RAM3, and displayed on display device 7.

The amount of exercise may be obtained as the product of exercise intensity and exercise duration. Accordingly, it is also acceptable to display the exercise amount obtained as this product in place of the calorie display. In other words, the measured pulse rate and the exercise intensity satisfy the following well-known Karvonen equation, so that exercise intensity can be calculated from the resting pulse rate which was prestored in RAM3 and the pulse rate which is measured during exercise, to obtain the amount of exercise.

$$\text{Measured pulse rate} = (\text{resting pulse rate}) + \{(220-\text{age}) - \text{resting pulse rate}\} * \text{exercise intensity} \quad \ldots (1)$$

When "exercise intensity" in this formula reaches 80%, exercise is very difficult, while a level of 50% is moderately challenging. With regard to "age" in this formula, the user inputs his age using an input means not shown, with this value prestored in RAM3.

CPU1 checks whether or not the exercise intensity calculated from the measured pulse rate using formula (1) is outside the range determined by the aforementioned upper and lower limit values for exercise intensity. If exercise intensity exceeds the upper limit value, then CPU1 guides the user to exercise a bit more moderately, while if exercise intensity falls below the lower limit, CPU1 guides the user to slightly increase the intensity of exercise.

Accordingly, by displaying the pulse rate and exercise amount on display device 7, the user can increase or decrease the exercise being performed. At the same time, since it is possible to check whether or not exercise of the appropriate intensity is being carried out, excessive or ineffective exercise is avoided. In this way, monitoring is carried out to ensure that exercise of the appropriate intensity is performed.

When an interrupt from watch circuit 9 is generated after the elapse of the targeted exercise duration, CPU1 outputs a directive to the user to stop exercising. The user either stops immediately, or continues until reaching a more convenient stopping point. Accordingly, the output value of acceleration sensor 5 gradually decreases. Meanwhile, since CPU1 is monitoring the output value of acceleration sensor 5, it detects that the output value has again fallen below the prespecified value described above, and thereby recognizes that the user has suspended exercise.

Next, CPU1 calculates the amplitude ratio d/a following the same procedure as performed prior to starting exercise, and reads out the current clock time from watch circuit 9, which it records in RAM3 as the exercise-stop time. CPU1 then calculates the total exercise duration based on the exercise-start time and the exercise-stop time, and stores this in RAM3 in the same manner.

Next, CPU1 displays the pre-exercise amplitude ratio d/a, the post-exercise amplitude ratio d/a, the total exercise amount, and the total exercise duration on display device 7 in accordance with the manipulation of a button switch by the user. In addition, CPU1 obtains the target exercise amount from the exercise intensity target value and the exercise duration target value, and determines whether or not the total exercise amount measured is within a prespecified range centered around this target value. If the exercise amount is not correct, then CPU1 notifies the user of this fact, together with the targeted value for the exercise amount, so that the user is made aware that exercise was not carried out as directed. CPU1 also carries out the same processing with respect to exercise duration, and alerts the user when a notable difference is found between the targeted value and the actual measured value.

Next, in the same manner as carried out prior to exercise, CPU1 determines which of the patterns shown in FIG. 2(b) is associated with the amplitude ratio d/a measured after exercise, and displays the post-exercise pattern type on display device 7. If a comparison of the pre-exercise and post-exercise patterns reveals that there was an improvement toward a type (1) pattern, then a message such as "health state improved" is displayed on display device 7. On the other hand, a comparison may reveal a deterioration toward a type (6) pattern. Since further exercise may not be desirable in this case, the user is cautioned not to exercise, and to consult a physician if necessary.

In the absence of such a warning, however, when the user plans to continue exercising further, such as in the case of interval training, for example, then this post-exercise exercise pattern (i.e., amplitude ratio d/a) is set as the pre-exercise pattern (amplitude ratio d/a) for the exercise which is to be performed from that point on. A new target value is set from this pattern (amplitude ratio d/a), and exercise guidance is continued. Subsequently, if the user again pushes button switch 117 after completing the necessary amount of exercise, CPU1 determines that exercise has ended, and terminates further exercise guidance.

On the other hand, if the user exercises on the following day or beyond, then exercise guidance is suspended once button switch 117 is depressed. Thereafter, the acceleration pulse wave patterns for the health state on that day are determined in accordance with the procedure described above. Thus, exercise guidance in line with the exercise target value corresponding to the pattern for that day is carried out.

In this way, the user's health state is moved toward a better condition by providing guidance to the user to carry out appropriate exercise.

In this embodiment, it is also acceptable to continually display the measured pulse rate, both before and after exercise, on display device 7.

Additionally, the following may be considered as one method for evaluating the exercise performed by the user.

Figure 8:
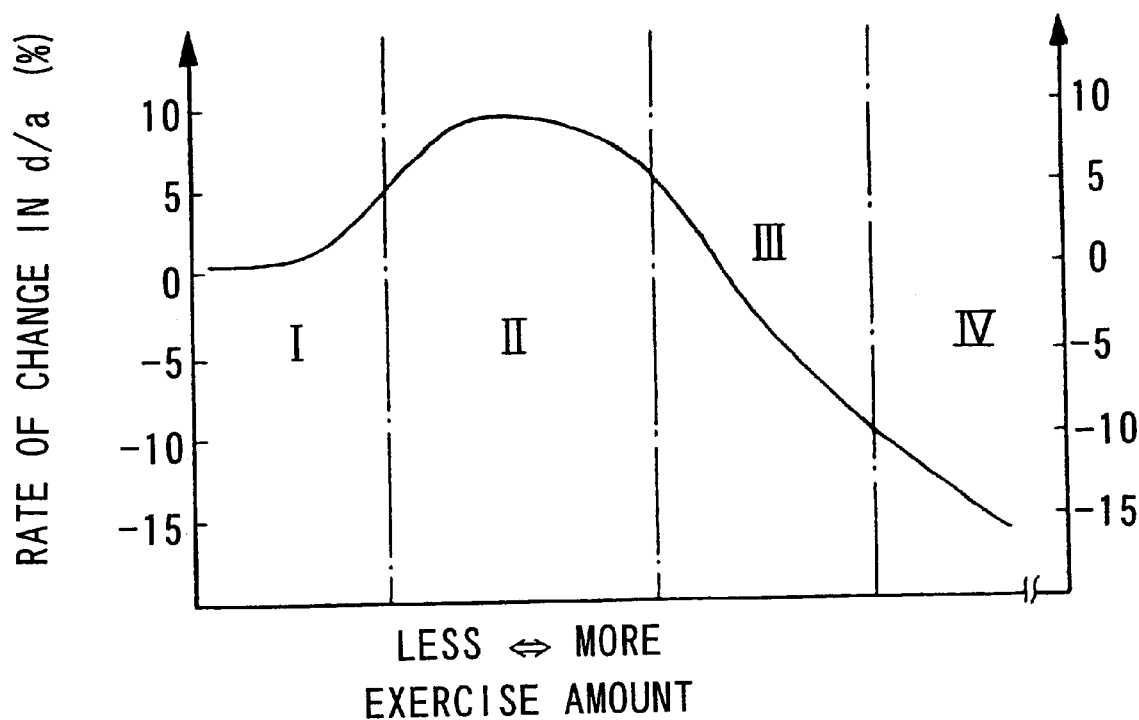
FIG. 8 is a view showing the relationship between the amount of exercise performed by the user and the rate of change in amplitude ratio d/a measured before and after exercise.

FIG. 8 shows an example of the relationship between the amount of exercise performed by the user and the rate of change in amplitude ratio d/a before and after exercise. As shown in this figure, when the amount of exercise is little, then the rate of change in amplitude ratio d/a is small, with a value of +5% or less generally obtained (region I in FIG. 8). When the amount of exercise is greater than this, then the rate of change in amplitude ratio d/a gradually increases above +5%. Subsequently, the rate of change begins to fall after a certain point, until it again is around +5% (region II in FIG. 8). When the amount of exercise is increased further, the rate of change in amplitude ratio d/a falls further, dropping below +5% to around −10% (region III in FIG. 8). A further increase in the amount of exercise leads to a further decline in the rate of change in amplitude ratio d/a, to below −10% (region IV in FIG. 8).

CPU1 carries out an evaluation of exercise based on the relationship between the amount of exercise and the rate of change in amplitude ratio d/a. In order to do this, CPU1 determines the difference between the post-exercise amplitude ratio d/a and the pre-exercise amplitude ratio d/a and divides this difference by the pre-exercise amplitude ratio d/a, thereby calculating the rate of change in amplitude ratio d/a. The rate of change in the obtained amplitude ratio d/a and the measured amount of exercise are plotted on the graph in FIG. 8, and CPU1 then makes an evaluation of the exercise performed by the user according to which region I–IV this plot is positioned in.

Namely, if the plot is in region I of FIG. 8, then CPU1 determines that exercise was too mild. If the plot is in region II, then CPU1 determines that exercise was appropriate. If the plot is in region III, then CPU1 determines that exercise was slightly strenuous. And if the plot is in region IV, then CPU1 determines that exercise was too strenuous. Based on these results, the messages "exercise too mild", "exercise appropriate", "exercise slightly too strenuous", and "exercise too strenuous" are displayed on display device 7, in the case of plots in region I, II, III and IV, respectively. In this way, the user is notified of the results of the exercise evaluation.

The preceding embodiment described a case employing the amplitude ratio d/a only. However, by employing an evaluation method which uses both amplitude ratio d/a and c/a, it is possible to carry out an evaluation of exercise which is even more accurate. Namely, if, for example, the value of the amplitude ratio is 20%, then a determination can be made that the waveform of the acceleration pulse wave is associated with a pattern (2) type waveform. On the other hand, if the value of amplitude ratio d/a is 80%, then it is possible to specify that the acceleration pulse waveform is associated with one of patterns 4 through 6. Reference is then made to the value of the amplitude ratio c/a to determine which is the pattern from among these. If the value of amplitude ratio c/a is 30%, for example, then, from FIG. 2(b) it is possible to determine that the acceleration pulse waveform is associated with a pattern (5) type waveform.

In addition to exercise intensity and exercise duration, other parameters may be considered for use as target values during exercise. Calorie consumption may be cited as one example. CPU1 sets the targeted value for calorie consumption prior to beginning exercise, and calculates calorie consumption each time the pulse rate is measured during exercise. CPU1 calculates the total calorie consumption from the start of exercise and stores this value in RAM3. When this value exceeds the set target value, CPU1 provides notification to the user.

Embodiment 2

Information such as the power spectrum obtained from heartbeat variation has begun to be used in the diagnosis and treatment of various ailments such as heart disease, central nerve disorders, peripheral nerve disorders, diabetes, high blood pressure, cerebrovascular disease, sudden death and the like in recent years. Accordingly, this embodiment obtains the LF (low frequency), HF (high frequency) and RR50 indicators from an analysis of the pulse tidal wave, which corresponds to the tidal wave in heartbeat variation, and employs these as indicators of the user's physical state. We will first explain the significance of these indicators.

Figure 9:
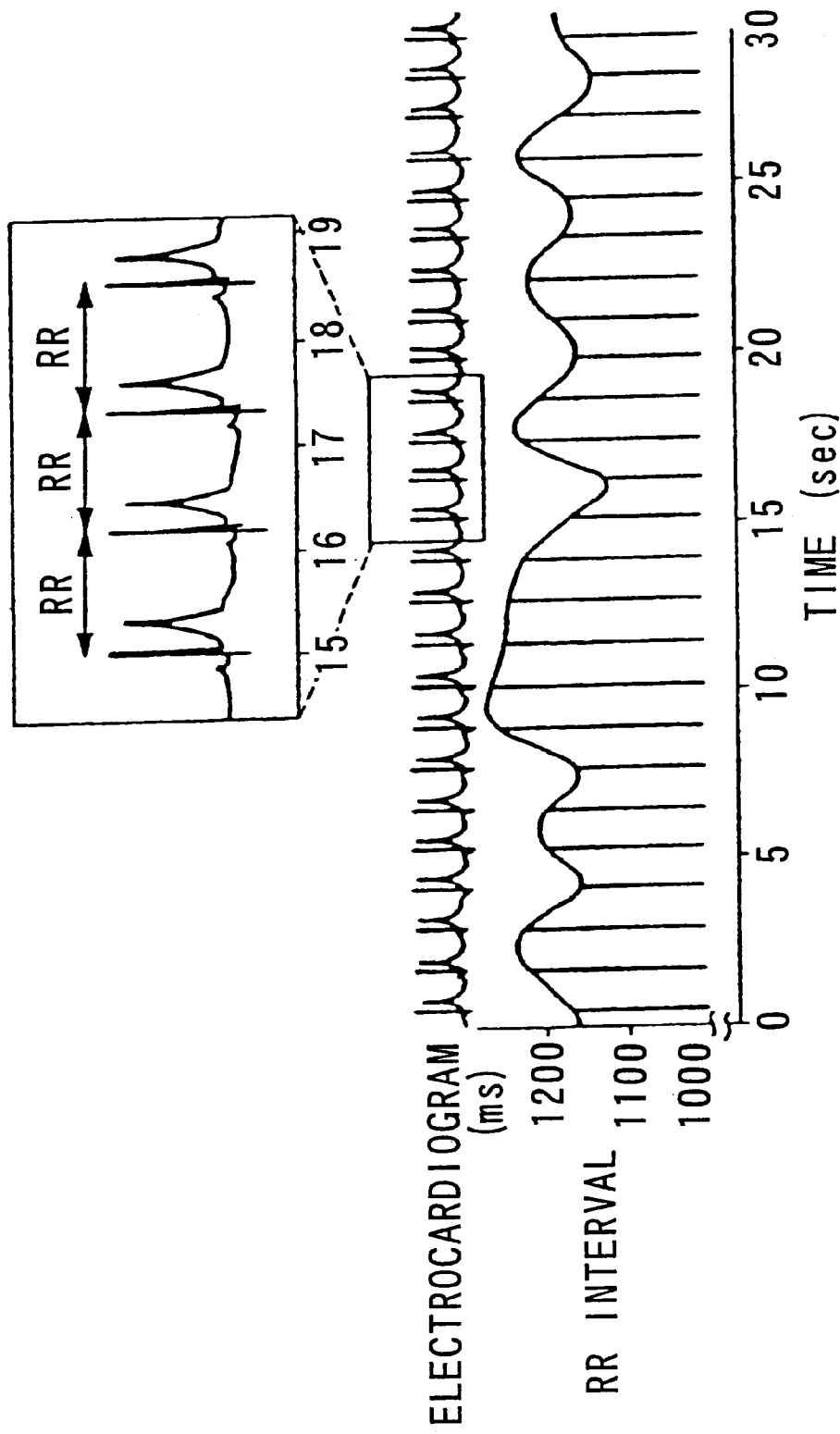
FIG. 9 shows the relationship between an electrocardiogram and the RR interval.

In an electrocardiogram, the interval between the R wave of one heart beat and the R wave of the next heart beat is referred to as the RR interval. This RR interval is a numerical value which serves as an indicator of the functioning of the autonomic nervous system in the human body. FIG. 9 shows heartbeat and the RR interval obtained from the waveform of this heartbeat in an electrocardiogram. As may be understood from this figure, an analysis of the measured results in an electrocardiogram reveals that the RR interval varies over time.

Figure 10:
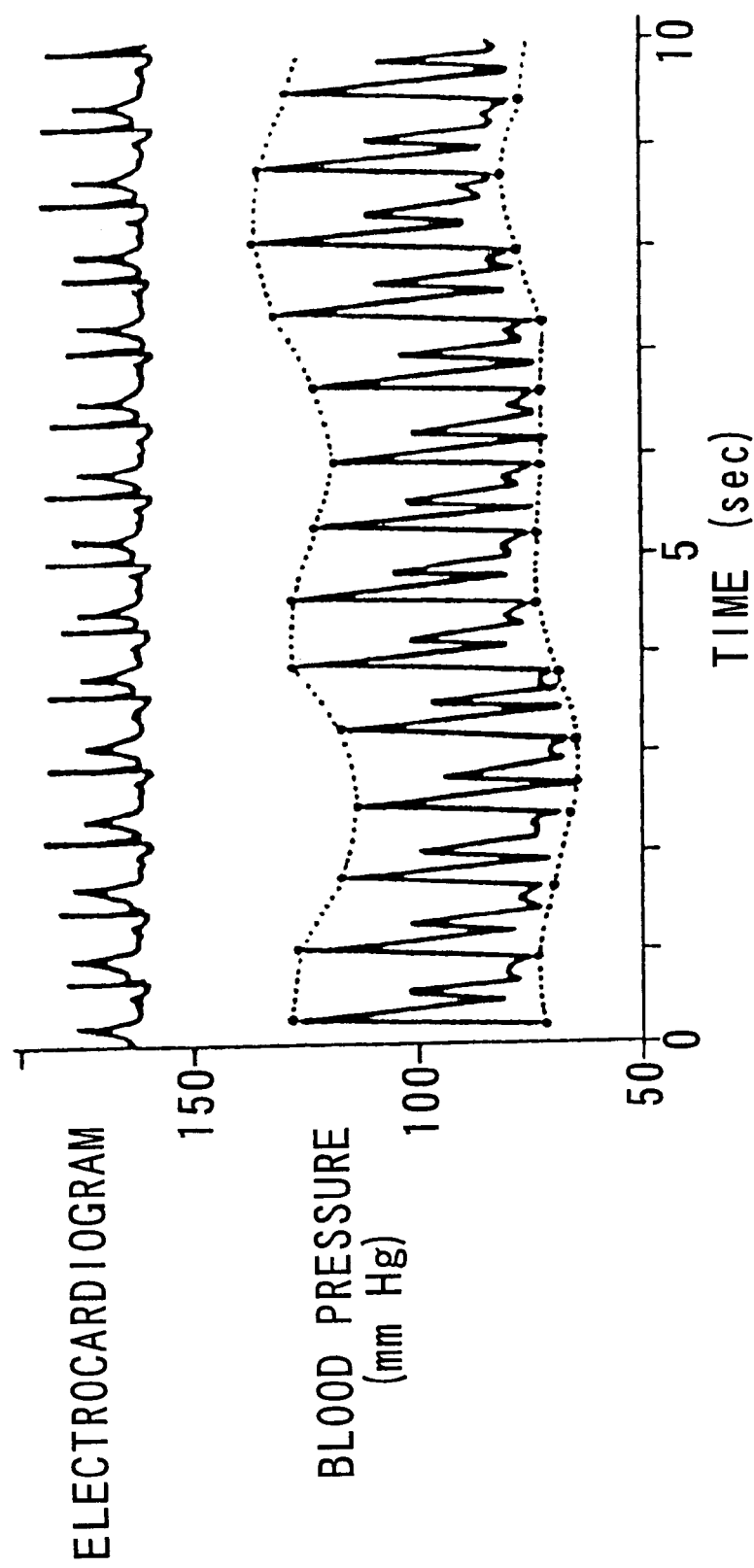
FIG. 10 shows the relationship between an electrocardiogram and the pulse wave.

On the other hand, variation in blood pressure measured at the radius artery or the like, is defined as the variation in blood pressure at each beat from contraction to relaxation of the heart, and corresponds to variation in the RR interval in an electrocardiogram. FIG. 10 shows the relationship between the electrocardiogram and blood pressure. As may be understood from this figure, the blood pressure during each contraction and relaxation in a heart beat can be measured as the maximum value of arterial pressure, and the minimum value immediately preceding this maximum value in each RR interval.

By carrying out spectral analysis of variations in heart beat or blood pressure, it may be understood that the variations are composed of waves having a plurality of frequencies. These may be classified into the following three types of variation components.

Figure 11B:
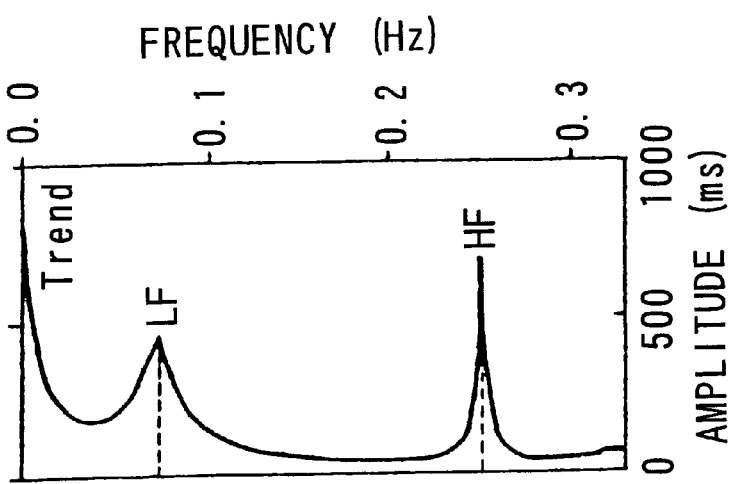
FIG. 11(b) shows the results of spectral analysis of change in the RR interval.
Figure 11A:
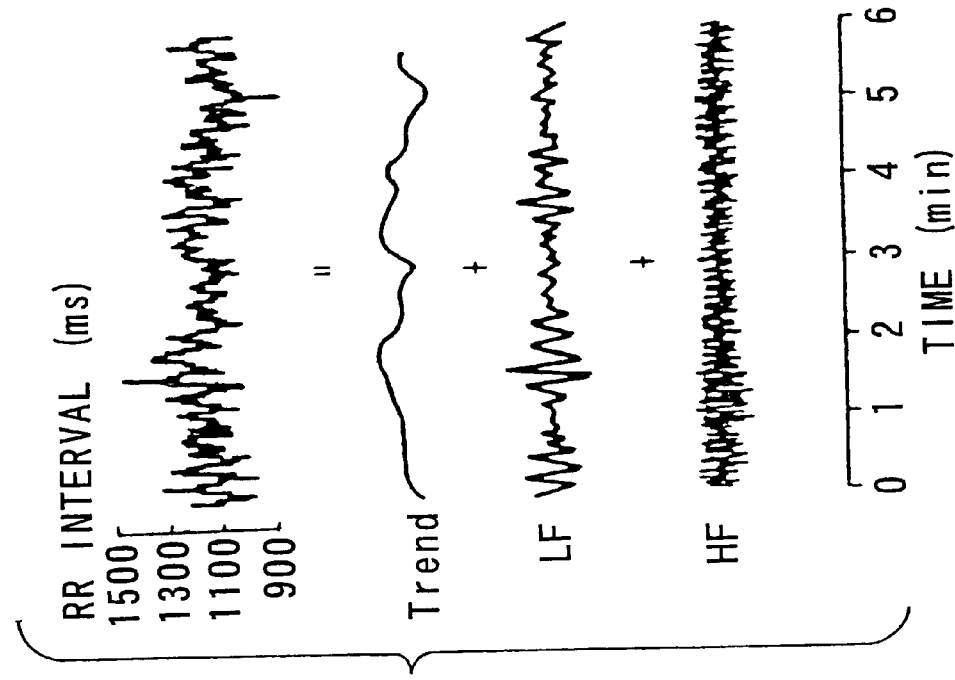
FIG. 11(a) shows the relationship between change in the RR interval and the frequency component which composes the change.

1. HF (high frequency) component which is the variation coinciding with respiration
2. LF (low frequency) component which varies with a periodicity of around 10 seconds
3. Trend which varies with a frequency which is lower than the measurement limits In order to obtain these components, the RR interval between neighboring pulse waves is obtained for each measured pulse wave, and the discrete value of the obtained RR interval is interpolated using a suitable method (for example, 3rd order spline interpolation) (see FIG. 9). An FFT operation is carried out on the curved lined after interpolation, followed by spectral analysis. As a result, it is possible to pick out the variation component as a peak on the frequency axis. FIG. 11(a) shows the waveform of variation in the RR interval of a measured pulse wave and the waveform of each of the components of variation in the case where the waveform of variation is segregated into the three frequency components noted above. FIG. 11(b) shows the results of spectral analysis on the waveform of variation in the RR interval shown in FIG. 11(a).

As may be understood from this figure, peaks are apparent at two frequencies near 0.07 Hz and 0.25 Hz. The former frequency value is the LF component, while the latter is the HF component. The trend component cannot be read in the figure because it is below the limit for measurement.

The LF component is related to the activity of the sympathetic nervous system. The larger this component, the greater the increase in tension. On the other hand, the HF component is related to the activity of the parasympathetic nervous system. The larger the amplitude of this component, the more relaxed the state.

The amplitude values for the LF and HF components will vary according to the individual. Accordingly, with this in mind, the proportion LF/HF, which is the ratio of the amplitudes of the LF and HF components, is useful to estimate the state of the subject. When the value of LF/HF is large, than the degree of tension is high, while when LF/HF is small, the degree of tension is low indicating the subject is relaxed.

RR50 is defined by the fixed number at which the absolute value of the pulse wave interval corresponding to the RR interval for two consecutive heart beats varies by 50 milliseconds or more, when measurements of pulse wave are carried out over a prespecified period of time. The larger the value of RR50, the more sedate the subject is, while the smaller the value of RR50, the more aroused the subject is.

There is, by the way, a correlation between these indicators and the physical state of the user.

As a result of lowering functioning of the parasympathetic nervous system and placing the sympathetic nervous system in a position of dominance through intensified training, it is possible to create a condition which resembles the physical state of a patient afflicted with a disease such as described above. If the intensified training is then suspended, and the change in the aforementioned indicators is observed as the body recovers, the HF component is found to increase as the day passes, while the LF/HF value tends to fall as the day goes by.

In other words, as the body's state recovers, the HF component or the LF/HF value increase or decrease from a value indicating a state of tension to a value indicating a state of relaxation. Accordingly, it may be hypothesized that by observing not only the HF component and LF/HF value, but also the LF component and the RR55 value, it is possible to judge whether or not the body state is good by observing the increase and decrease in the values in each of the indicators. Accordingly, these indicators may be used in place of amplitude value d/a.

The health management device according to this embodiment will now be explained. In this embodiment, one of the four indicators described above is used in place of the amplitude ratio d/a employed in Embodiment 1. The structure of this device is the same as that in Embodiment 1. Therefore, the following explanation will focus on those aspects of the device's operation which are specific to this embodiment.

Additionally, the acceleration pulse waveform was divided into 6 patterns in the preceding embodiment. In this embodiment, however, the indicators are divided into a number of grades according to the value thereof. An exercise intensity target value, upper and lower limit values for exercise intensity, and a target value for exercise duration have been preset in ROM2 corresponding to each of these grades.

When the user presses button switch 117 prior to beginning exercise, CPU1 checks the output value of acceleration sensor 5 and, after confirming whether or not the user is in a state of repose, measures the resting pulse rate once, and stores this value in RAM3. Next, CPU1 takes up the pulse waveform, and calculates the four indicators based on this pulse waveform. The processing which follows thereafter will now be explained in detail below.

First, in order to extract the maximum points from the pulse waveform, CPU1 calculates the time derivative of the pulse waveform, and obtains all the clock times at which there is pole in the waveform by determining the where the time derivative is zero. Next, CPU1 determines whether each pole is a maximum or minimum, from the slope of the waveform in the vicinity the pole (i.e., the time derivative). In other words, for a given pole, CPU1 calculates the moving average of the slope of the waveform over a fixed time interval preceding the pole. If this moving average is positive, then the pole is a maximum, while if the value is negative, the pole is a minimum.

Next, for each extracted maximum point, CPU1 determines the minimum point present immediately preceding the maximum point. The pulse wave amplitudes at the maximum and minimum points are read out from RAM3, and the difference between them is determined. If this difference exceeds a prespecified value, then the clock time of that maximum point is designated as a peak in the pulse wave. After carrying out this peak detection processing on all the pulse waveforms taken up, the time interval between two adjacent pulse wave peaks is calculated based on the clock time at which these peaks occur (corresponding to the RR interval between heartbeats).

The value of the obtained RR interval is discrete along the time axis. Accordingly, a curved line such as shown in FIG. 11(a) is obtained by interpolation between neighboring RR intervals using a suitable interpolation method. Next, a spectrum such as shown in FIG. 11(b) is obtained by carrying out FFT processing on the interpolated curved line. Processing to determine maximums is carried out in the same manner as performed on the pulse waveform, to obtain the frequencies in the spectrum corresponding to the aforementioned maximum and maximum values. The maximum value obtained in the low frequency region is defined as the LF component, while the maximum value obtained in the high frequency region is defined as the HF component.

Further, the amplitudes of these components are obtained and the amplitude ratio LF/HF is calculated. The time difference in neighboring RR intervals is sequentially obtained based on the RR interval obtained above. Next, a check is made of each of these time differences to confirm whether or not the time difference exceeds 50 milliseconds, and the fixed number of time differences exceeding 50 milliseconds is counted and set as RR50.

CPU1 directs the user regarding the exercise to be carried out. First, CPU1 determines the grade to which the index value obtained as above is associated. The determined grade and the value of the index are stored in RAM3, and displayed on display device 7. The exercise intensity target value, the upper and lower limit values for exercise intensity, and the target value for exercise duration are read out from ROM2, stored in RAM3 and displayed on display device 7, so that the user is presented with these exercise target values.

Next, the user begins to exercise. CPU1 recognizes this, and stores this as the exercise-start time in RAM3, and sets the targeted exercise duration in watch circuit 9. Then, in the same manner as in Embodiment 1, CPU1 measures the user's pulse rate and exercise amount during exercise, and provides guidance to the user as he exercises. In other words, CPU1 calculates the user's pulse rate and the amount of exercise from the previous pulse rate measurement to the current pulse rate measurement, thereby determining the total amount of exercise since the user started to exercise. These values are stored in RAM3, and displayed on display device 7. CPU1 checks whether or not the exercise intensity calculated from equation (1) is within the range determined by the upper and lower limit values for exercise intensity, and outputs directive relating to the appropriate exercise intensity to the user.

CPU1 directs the user to end exercise when an interrupt from watch circuit 9 is generated after the targeted exercise duration has elapsed. CPU1 observes the output of acceleration sensor 5 and waits for the user to actually stop exercising. Next, CPU1 calculates each indicator in the same way as prior to the start of exercise, and reads out the exercise-stop time from watch circuit 9 to calculate the total exercise duration. CPU1 then stores all these values in RAM3, and displays them on display device 7. Next, CPU1 determines whether the total amount and duration of the exercise just performed are within the prespecified limits based on the respective target values. When exercise has not been carried out as directed, then CPU1 notifies the user of this fact.

Next, in the same way as before exercise, CPU1 determines the grade to which the index value after exercise is associated, and displays the obtained grade and index value on display device 7. Next CPU1 compares the index values before and after exercise. If an improvement in physical state is observed, then a message to that effect is displayed on display device 7, while if a deterioration in physical state is observed, then a warning is provided to stop exercise and consult a physician.

Where using LF and LF/HF as standards for judging whether physical state has improved or deteriorated, a decrease in the value due to exercise indicates improvement, while an increase indicates deterioration. In contrast, when HF and RR50 values are employed, a decrease indicates deterioration, while an increase indicates improvement.

If the user plans to continue to exercise beyond this point, then the grade obtained after exercise is set as the pre-exercise grade for the exercise to performed from that point on. A new target value is obtained based on this grade, and CPU1 continues exercise guidance.

Additionally, it should be noted that while one indicator from among the four described above was employed in this embodiment, it is acceptable to use any number of these indicators in a composite way.

Embodiment 3

Part of the health management device described in Embodiment 1 is modified in this embodiment. Namely, in the Embodiment 1, the device (or more specifically, CPU1) automatically determined whether or not the user was in a state of repose based on the measured result from acceleration sensor 5. In contrast, in this embodiment, the user himself determines whether or not he is in a state of repose, and provides direction of this fact to the device.

Additionally, the operational mode in the first embodiment was composed of two modes, namely, one mode in which the device functions as a health management device, and another mode in which the device is used as a stop watch or an ordinary watch in which time and date is set. In contrast, in this embodiment, the operational mode is divided into three types of modes.

In the first mode, the device has no function as a health management device, but serves as an ordinary wristwatch when incorporated in a timepiece. In the remaining two modes, the device functions as a health management device. Namely, the second mode is a pulse wave measurement mode which carries out measurement and analysis of the user's pulse waves before or after exercise, based on the assumption that the user is in a state of repose. The third mode is a pulse measurement mode for measuring the pulse rate while the user is exercising, and providing exercise guidance.

The user carries out switching between these three modes using button switch 117. In the first embodiment, button switch 117 was a switch for starting or terminating the operation of the device as a health management device. In contrast, in this embodiment, button switch 117 serves as a button switch for cyclic switching between the three modes described above. Namely, each time button switch 117 is pressed, the device cycles from mode 1 through mode 3 (mode 1→mode 2→mode 3→mode 1). Further, the device is designed not to fix the mode while mode switching is being carried out. Rather, the user continues pressing button switch 117 until the desired mode appears.

As is clear from the preceding explanation, in this embodiment, the user himself makes the determination that he is in a state of repose, whereas in the first embodiment the determination was made using acceleration sensor 5. Accordingly, in this embodiment, an acceleration sensor 5 is not needed.

Next, an overview will be provided of the operation of the present embodiment's health management device.

First, prior to beginning exercise, the user presses button switch 117 and sets the device in pulse wave measurement mode while taking care not to move pulse wave sensor 4. As a result, CPU1 reads out the pulse waveforms over a prespecified period of time from sensor interface 6, calculates the resting pulse rate from the pulse waveforms taken up, and stores these results in RAM3.

Next, CPU1 reads out a portion of the pulse waveform, determines the acceleration pulse waveform, sets peak a, valley b, peak c and valley d, calculates amplitude ratio d/a, and determines the acceleration pulse waveform pattern from this amplitude ratio d/a. CPU1 then stores these values in RAM3. Next, CPU1 reads out the exercise target values corresponding to this pattern from ROM2, stores them in RAM3, and displays these values on display device 7, along with a message stating that pre-exercise pulse wave measurement is completed.

Having confirmed this message, the user operates button switch 117 and sets the device in pulse measurement mode. Accordingly, CPU1 reads out the exercise-start time from watch circuit 9, stores this in RAM3, and sets the exercise duration in watch circuit 9. Having pressed button switch 117, the user starts to exercise. As a result, CPU1 measures the user's pulse rate and exercise amount, and provides exercise guidance to the user in the same way as in Embodiment 1.

CPU1 directs the user to end exercise when an interrupt from watch circuit 9 is generated. When exercise is terminated in accordance with this directive, the user again switches the device to pulse wave measurement mode by manipulating button switch 117. As a result, CPU1 reads out the exercise-stop time, calculates the total exercise duration, and stores this in RAM3. CPU1 then recognizes that the current pulse wave measurement mode is for measuring the post-exercise pulse wave. Then, following the same procedure employed prior to the start of exercise, CPU1 calculates the amplitude ratio d/a from the pulse waveforms taken up, determines the acceleration pulse wave pattern, and stores these values in RAM3.

Next, CPU1 displays the pre-exercise amplitude value d/a, post-exercise amplitude value d/a, and total exercise amount during the session on display device 7, and checks whether or not the amount and duration of exercise was correct, providing a warning to the user as necessary. Also, CPU1 checks the change in the acceleration pulse waveform before and after exercise, and carries out the appropriate direction to the user according to the degree of improvement or deterioration therein.

Subsequently, after the user has regulated respiration so that the resting pulse rate can be obtained, the above-described operations are repeated, starting from the operation for measuring the pre-exercise pulse waves.

It may occur that the user's body moves, impairing measurement during the pulse wave measurement mode. Therefore, as a supplementary measure, an acceleration sensor 5 may be employed. Namely, when measuring the pulse waves before and after exercise, CPU1 regularly reads the output of acceleration sensor 5. If CPU1 detects that the user's body is moving, a warning message may be displayed on display device 7, or a warning may be generated by means of an alarm housed inside the device.

Additionally, it is also acceptable to provide separate modes for measuring the pre-exercise pulse wave and post-exercise pulse wave, with the user selecting one of these modes according to whether he is starting or has finished exercise.

The device of the present embodiment was explained as an application to the first embodiment. However, if LF, HF, LF/HF and RR50 are substituted for the amplitude ratio d/a, then this device may of course be applied to the second embodiment as well.

Embodiment 4

An explanation will now be made of an embodiment in which a health management device of the above structure is applied to guide a physical rehabilitation process, using the case where the amplitude ratio d/a obtained from the acceleration pulse wave is employed.

A rehabilitation process is ordinarily comprised of a number of steps, with the process moving toward more intense exercise as the treatment proceeds, so that the patient's condition improves. In this embodiment, exercise guidance is automatically provided to a patient undergoing rehabilitation, without the intervention of an additional person.

Standard target values for the amplitude ratio d/a or the like for each step of the rehabilitation process are stored in the ROM2 shown in FIG. 1. In addition, an exercise intensity target value, the upper and lower limit values for exercise intensity, and the target value for exercise duration, which are deemed appropriate so that the body will reach a state having the targeted amplitude ratio d/a are also set in ROM2.

First, preparation to begin rehabilitation is carried out. Namely, CPU1 takes up the patient's pulse waves, obtains the acceleration pulse wave, and determines each amplitude ratio. CPU1 also calculates the resting pulse rate. As will be explained below, these values indicate the state of the patient who is to undergo rehabilitation on that day. The standard target value for the amplitude ratio stored in ROM2 is corrected using the resting pulse rate value and the measured amplitude ratio. The targeted amplitude ratio coinciding with the patient's physical state at the start of rehabilitation is calculated, and stored in RAM3. Next, the exercise intensity target value, the upper and lower limit values for exercise intensity, and the target value for exercise duration, corresponding to this targeted amplitude ratio are read out from ROM2, and are reported to the user along with the targeted amplitude ratio. When correcting the standard amplitude ratio, both the measured amplitude ratio and the pulse rate may be used, or just one of these may be used.

Next, CPU1 displays a message on message display 7 prompting the user to begin rehabilitation. As a result, the patient starts first-stage exercise. CPU1 measures the patient's pulse rate during exercise, and calculates the exercise intensity from the measured pulse rate. CPU1 then checks whether or not exercise intensity is within the upper and lower limit values described above, and directs the patient as appropriate to maintain the correct exercise intensity. In addition, CPU1 also obtains the exercise amount at fixed intervals of time, and adds this to the total exercise amount since the start of rehabilitation.

After the elapse of the targeted exercise duration, CPU1 directs the patient to stop exercising. Once the patient stops exercising, CPU1 again takes up the pulse waves, calculates the post-exercise amplitude ratio, and checks whether or not this amplitude ratio has reached the target value for that exercise stage in the rehabilitation process. If the measured value has not reached the targeted value, then CPU1 directs the patient to continue exercise until the measured value reaches the target value.

On the other hand, if the measured value has reached the targeted value for exercise at that stage in the rehabilitation process, then CPU1 displays a message on display device 7 prompting the patient to move on to the next exercise stage. At this second stage, the new standard target value for the amplitude ratio is read out from ROM2, and corrected in the same manner as described above. Then, a new exercise intensity target value, new upper and lower limit values for exercise intensity, and a new target value for exercise duration, corresponding to the corrected amplitude ratio target value, are displayed. As a result, the patient terminates first stage exercise and moves on to second stage exercise. In this way, the patient proceeds through the rehabilitation menu by stages.

When all stages have been completed, CPU1 displays a message on display device 7 indicating rehabilitation is complete. Accordingly, the patient ends rehabilitation.

The present embodiment was explained using the amplitude ratio d/a. However, LF, HF, LF/HF and RR50 values may of course be substituted therefor.

Embodiment 5

An explanation will now be made of the case where the user applies a health management device of the above structure to the management of his own health.

CPU1 takes up pulse waves from sensor interface 6 daily, at times preset for this measurement. In this embodiment, measurements are carried out every two hours. Amplitude ratio d/a is calculated by the same process as employed in the first embodiment, and stored in RAM3 together with the clock time read out from watch circuit 9. If the user is exercising at the time for pulse wave measurement, the amplitude ratio cannot be calculated. Accordingly, in this case, CPU1 is designed to monitor the output of an acceleration sensor 5 and wait until exercise is completed, after which it carries out the measurement of the amplitude ratio.

When it is time for pulse wave measurement (for example, 2 o'clock), CPU1 reads out from RAM3 amplitude ratios which were obtained at the same time (i.e., 2 o'clock) over a past interval of time (one week in this embodiment). The moving average between the current amplitude ratio and these past amplitude ratio values is obtained, and is stored in RAM3 together with the current amplitude ratio and the clock time at which the measurement was conducted.

Next, the value of the moving average calculated at the same time on the prior day (i.e., 2 o'clock on the previous day) is read out from RAM3, and compared to the current amplitude ratio. A check is made to see if the difference between these two values exceeds a prespecified value. If the difference exceeds this value, then a warning message is displayed on display device 7, so that the user is made aware and provide with a warning that his current state deviates from his average state at that time over the past week.

In the preceding explanation, the amplitude ratio obtained from the pulse wave was used without modification. However, if the acceleration sensor 5 is viewed as an activity monitor, then it is possible to obtain the correlation between the user's body movement and the acceleration pulse wave. Thus, when calculating the amplitude ratio, the value of the measured amplitude ratio may be corrected using this correlation information and the output value of acceleration sensor 5.

The transitions in the amplitude ratio over an interval of time in the past (one week, one month, one year, etc.), which are stored in RAM3, are displayed as a graph on display device 7. In this way, it is possible for the user to be informed of changes in the state of circulation.

The preceding explanation employed the amplitude ratio d/a described above, however, it is of course acceptable to use LF, HF, LF/HF and RR50.

Embodiment 6

Figure 19:
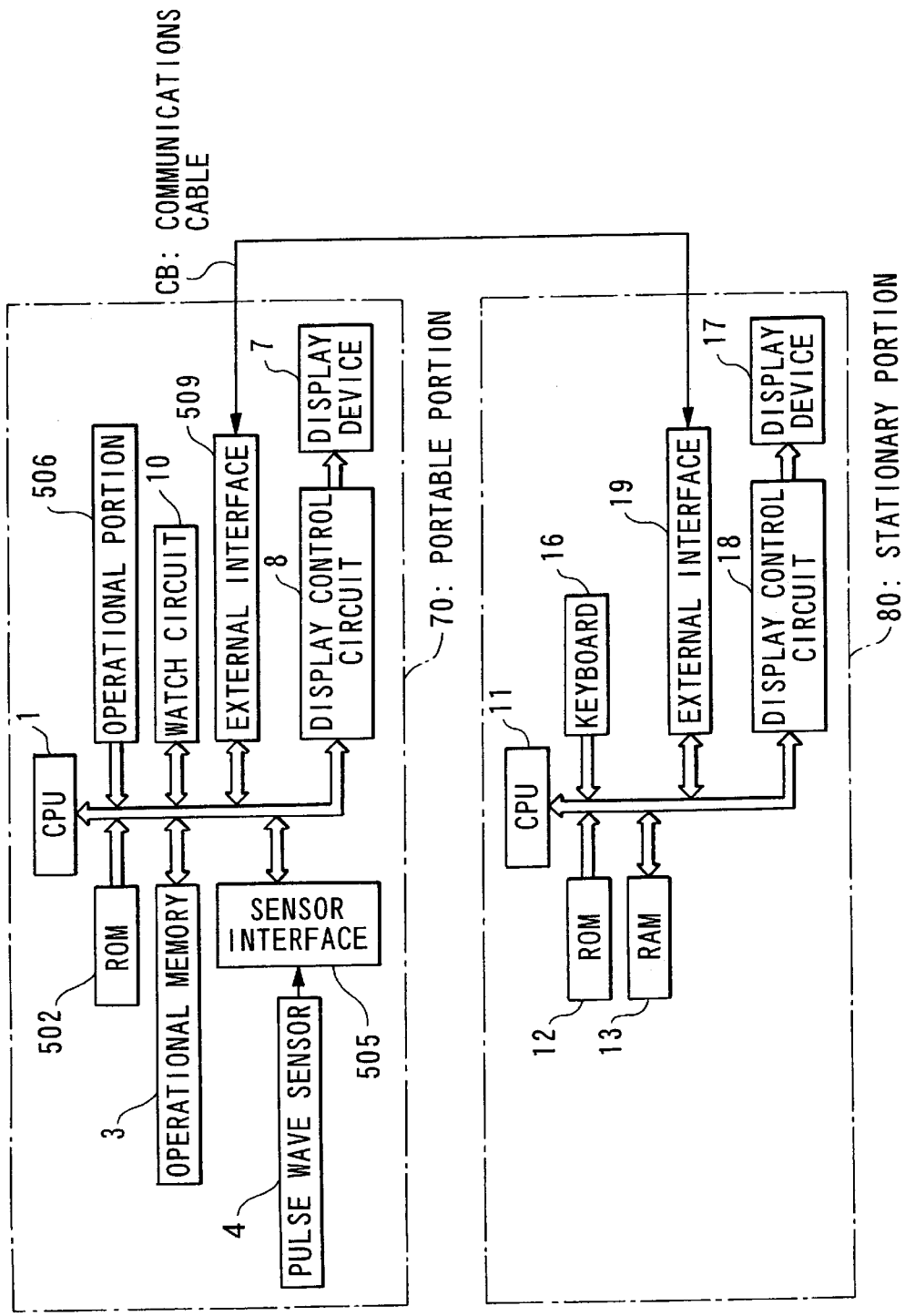
FIG. 19 is a block diagram showing the structure of an exercise support device according to one embodiment of the present invention.

Next, the structure of an exercise support device according to this embodiment will be explained. FIG. 19 is a block diagram showing the structure of this device. The device is roughly divided into two blocks. The first block is a portable portion 70, which is incorporated in a portable device such as a watch. Portable portion 70 cooperates with a stationary portion 80, which will be explained below, to measure the acceleration pulse wave before and after exercise, measure the pulse rate during exercise, and provide guidance to the user to carry out the appropriate exercise.

Figure 24:
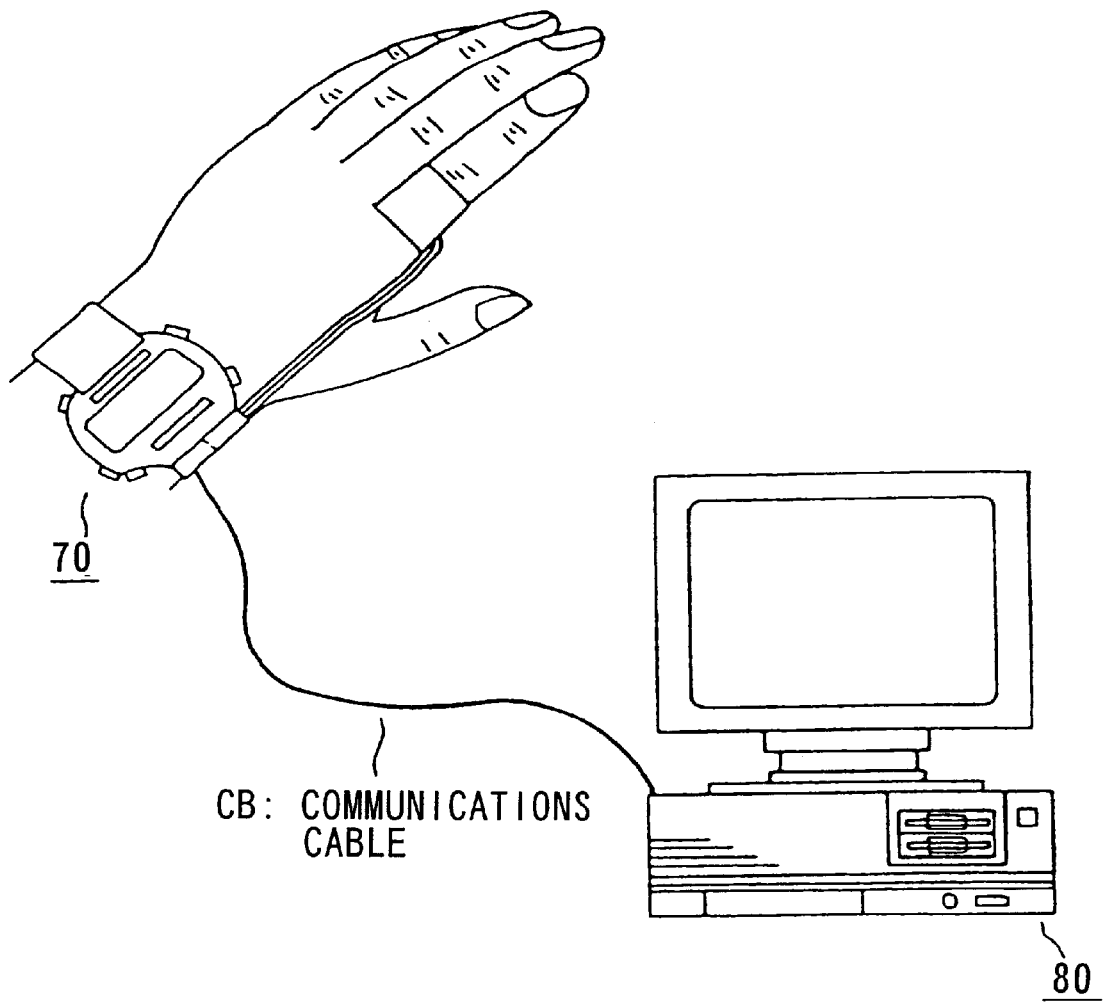
FIG. 24 is a diagram showing the mechanical connection between portable portion 70 and stationary portion 80 of the device.

In contrast, the second block, stationary portion 80, is a so-called personal computer. Stationary portion 80 carries out analysis of the pulse waves and various processing, such as forming the exercise plan, which is too great for portable portion 70 to handle. Further, as shown in FIGS. 19 or 24, portable portion 70 and stationary portion 80 are connected in a freely detachable manner by a communications cable CB.

The roles of portable portion 70 and stationary portion 80 will now be explained in greater detail. Portable portion 70 and stationary portion 80 are connected and a measurement of the acceleration pulse wave is made prior to exercise. Processing to determine the exercise plan to be subsequently performed by the user is carried out by stationary portion 80. Next, stationary portion 80 is detached during exercise, so that portable portion 70 alone is used to measure the pulse rate and provide appropriate guidance to the user so that the planned exercise is executed faithfully. After performance of exercise, portable portion 70 and stationary portion 80 are again connected, and the acceleration pulse waves are measured. In addition, the data measured by portable portion 70 during exercise is sent to stationary portion 80. Stationary portion 80 then evaluates the user's health state based on this data. Based on the results of this evaluation, adjustment of the exercise plan is carried out as necessary.

An explanation will now be made of each of the circuits which make up portable portion 70. It should be noted that the CPU1 shown in FIG. 19 is the central part for controlling each of the circuits inside portable portion 70. An explanation of its function will be made below under the section concerning operations. In FIG. 19, the same numeric symbols have been applied to those parts which are identical to those pictured in FIG. 1.

The control programs executed by CPU1 and the various control data are stored in ROM 502 (read only memory). RAM3 stores the measurement data taken up from pulse wave sensor 4, the clock time at which the measurement data was taken up, the pulse rate calculated from the pulse wave taken up, and the total exercise amount since the user began exercising.

Pulse wave sensor 4 is an optical sensor which is attached to the user's finger. As in the first embodiment, pulse wave sensor 4 may be composed of a light-emitting diode and a light sensor using a photo transistor, for example.

Sensor interface 505 takes up the output of pulse wave sensor 4 over a prespecified art interval of time, converts the obtained analog signal into a digital signal, and outputs this digital signal.

Operational portion 506 is used by the user to direct portable portion 70 to carry out measurement of the acceleration pulse wave, pulse rate or the like. It may comprise a button switch or the like attached to a wristwatch, for example.

Display device 7 is a liquid crystal display provided to a wristwatch, for example. In addition to displaying the measured pulse rate and the total exercise amount, display device 7 also displays the details of the exercise plan to be carried out from that point on. For this purpose, display control circuit 8 receives display information from CPU1, converts it to a suitable format for display device 7, and displays it thereon.

External interface 509 is a circuit for carrying out data exchange between portable portion 70 and stationary portion 80 which is external to portable portion 70. For example, when realizing serial transmissions between portable portion 70 and stationary portion 80, external interface 509 may compose an exchange circuit which mutually exchanges serial data and parallel data.

Watch circuit 10 has the ordinary functions associated with a watch. The output thereof is employed as clock time at which data was measured. This watch circuit 10 also sends out an interrupt signal to CPU1 at clock times which have been preset by CPU1, or after the elapse of a time period which has been preset by CPU1.

Next, the circuits which form stationary portion 80 will be explained. CPU11 (central processing unit) is the central portion for controlling the circuits housed in stationary portion 80. Its functions will be explained below under the section concerning operations. Since it is necessary that CPU11 carry out various analytical processing over a short period of time, higher functioning is employed in CPU11 as compared to the CPU1 provided in portable portion 70.

The control programs executed by CPU11 and the various control data are housed in ROM12. In addition, as shown in FIG. 20 through 21, target values which form the standard for realizing desirable exercise are also stored in ROM12.

RAM13 (random access memory) provides an operational area for CPU11. The various data uploaded from portable portion 70 is stored in RAM13 over a prespecified interval of time. Accordingly, RAM13 is formed of a memory element which has a larger capacity than the RAM3 which is provided in portable portion 70.

Keyboard 16 is an input device by which the user inputs commands to stationary portion 80.

Display device 17 is an output device which is capable of graphic display. It displays various data measured by portable portion 70 and stationary portion 80, as well as various messages. In the same manner as display control circuit 18, display control circuit 18 is a controller for display device 17.

External interface 19 is a circuit for carrying out the exchange of data with portable portion 70, and has the same circuit structure as external interface 509.

The connection between portable portion 70 and stationary portion 80 is as shown in FIG. 24. Namely, a connector (not pictured) is provided to the personal computer composing stationary portion 80 for connecting communications cable CB. FIG. 24 shows the case where the wristwatch shown in FIG. 3 is employed as portable portion 70, however, arrangements such as shown in FIGS. 5(a) through 7, which will be discussed below, are also possible.

When incorporating portable portion 70 in a portable device, a number of arrangements may be considered. One example of these will be discussed below, however, the combination of portable portion 70 with a variety of other portable devices is of course possible.

As a first arrangement, an embodiment in which portable portion 70 is incorporated in the wristwatch shown in FIGS. 3(a) and 3(b) may be cited. As shown in this figure, portable portion 70 in this arrangement is composed of a device main body 100 which has the structure of a wristwatch, a cable 101 connected to the device main body 100, and a sensor unit 102 which is provided to the end of cable 101. Further, a wristband 103, which is wrapped around the wrist of the user from the 12 o'clock position and fixed in place at the 6 o'clock position of the wristwatch is attached to the device main body 100. This device main body 100 is designed to be freely detachable from the arm of the user by means of wrist band 103.

In the same manner as in the first embodiment, sensor unit 102 is blocked from light by a band 104 for fixing the sensor in place, and is attached between the base and the second joint of the index finger.

A connector 105a and connector 105b are provided to the surface of the wristwatch at the 6 o'clock position. Unit sensor 102 is connected to connector 105a via cable 101, while connector 105b is connected to stationary portion 80 via communications cable CB. Connector pieces 106a and 106b, which are provided to an end of cable 101 and communications cable CB, are attached to connectors 105a and 105b respectively, so as to be freely detachable. By releasing connector pieces 106a,106b from connectors 105a,105b, portable portion 70 may be used as a regular wristwatch or stopwatch.

Further, with the intention of protecting connectors 105a, 105b, a prespecified type of connector cover may be attached when cable 101 and cable CB are released from connectors 105a,105b. A component formed in the same way as connector pieces 106a,106b may be employed for the connector cover, with the exception that electrodes and the like are omitted from this connector cover component.

As stated in the first embodiment, in the above connector construction, the user can freely move his wrist during exercise. Moreover, even if the user falls during exercise, the back of the hand does not hit connectors 105a,105b.

A liquid crystal display 108 for the digital display of date, time, pulse rate and exercise quantity are provided to the surface of watch case 107 which is formed of a resin material. A number of button switches are provided to the outer periphery and surface of watch case 107. From among these, button switch 114, which is located at the 6 o'clock position on the wristwatch, is pressed when the user starts or completes exercise, and is for directing the start or stop of pulse rate measurement. Button switch 117, which is located at the 12 o'clock position of liquid crystal display 108 is a button switch for directing measurement of the acceleration pulse wave from portable portion 70 to stationary portion 80.

A button-shaped battery (not shown) is housed in watch case 107 and serves as an power source for the watch. Cable 101 supplies electric power from the battery to sensor unit 102, and sends the detection results from sensor unit 102 to device main body 100.

With regard to the correspondence between FIG. 19 and FIGS. 3(*a*) and 3(*b*), the CPU1, ROM502, RAM3, sensor interface 505, display control circuit 8, external interface 509, and watch circuit 10 in FIG. 19 are all incorporated inside watch case 107. The sensor unit 103, various button switches, and liquid crystal display 108 shown in FIG. 3 respectively correspond to the pulse wave sensor 4, operational portion 506, and display device 7 in FIG. 19.

An explanation will now be made of the operation of an exercise support device of the above construction, using the case of a wristwatch in which the sensor is attached to the base of the finger, such as shown in FIG. 24.

When the user begins exercise intended to create a state of health, processing is first carried out prior to the start of exercise to measure the acceleration pulse wave and analyze the pulse waves, so that the effect of the exercise subsequently carried out may be observed.

Accordingly, the user attaches portable portion 70 to stationary portion 80 using communications cable CB, and, after confirming that he is in a state of repose such that the measurement of the pulse waves will not be impaired, presses button switch 117 to initiate measurement. As a result, in addition to measuring the acceleration pulse waves, the following processing is carried out by portable portion 70.

First, pulse waveforms detected by pulse wave sensor 4 are sent to sensor interface 505 and converted to a digital signal. CPU1 reads out the pulse waveforms from sensor interface 505 for a prespecified period of time only, and sequentially stores this data in RAM3.

Next, the user's resting pulse rate is measured. Namely, CPU1 divides the pulse waveforms taken up in RAM3 into pulse units, and counts the pulse rate. The counted value is converted to a per minute value, and the thus-obtained value is stored in RAM3 as the resting pulse rate.

As will be explained below, the user's age and sex are necessary to prescribe an exercise plan. When the user's age and sex are not yet set in CPU1, a message is displayed on display device 7 prompting the input of this information. In response to the message, the user operates the button switches provided to the wristwatch, and sequentially inputs his age and sex via operational portion 506. CPU1 sequentially stores the input values in RAM3.

Next, CPU1 reads out the resting pulse rate, age, sex, and measured pulse waveform data from RAM3 via external interface 509, and sends this data to stationary portion 80. CPU11 then sequentially stores this data, which has been sent via external interface 19, in RAM13.

CPU11 then reads out one beat component from the pulse waveform stored in RAM13, and takes the second derivative of this waveform with respect to time. In this manner, the acceleration pulse waveform shown in FIG. 15 is obtained. Next, CPU11 obtains the inflection points of the acceleration pulse waveform, and determines peak a, valley b, peak c, and valley d. CPU11 then determines the amplitude values for each of these inflection points. These inflection points may be determined using a typical method such as taking the time derivative of the acceleration pulse wave. Additionally, it is also acceptable to send the waveform data of the calculated acceleration pulse waveform and the velocity pulse waveform obtained during the process of determining the acceleration pulse waveform to display control circuit 18, and display a graph of these waveforms on display device 17.

Next, CPU11 calculates the values when each of the amplitude values of valley b, peak c and valley d are normalized by the amplitude value of peak a, i.e., the amplitude ratios b/a, c/a, and d/a, and stores the calculated results in RAM13. From among these, amplitude ratio d/a is most useful as an indicator showing the state of circulation. Therefore, as a general rule, the embodiments of the present invention explained hereinafter will be explained using amplitude ratio d/a only. Additionally, we note here that, while it is preferable to employ both amplitude ratios d/a and c/a, the discussion hereinafter will employ only the amplitude ratio d/a as the most convenient method.

CPU11 determines which pattern (1) through (6) is associated with the acceleration pulse waveform, based on the amplitude ratio d/a obtained as above and the table shown in FIG. 2(*b*). This pattern type is stored in RAM13 as the pattern of the user's acceleration pulse waveform. In cooperation with CPU1, CPU11 displays the pattern type on display device 7. However, it would be difficult for the user to interpret the significance if just the pattern type was displayed. Accordingly, if, for example, the pulse waveform is found to be a pattern (3) type waveform, then a supplementary message such as "health state beginning to deteriorate" is sent to portable portion 70, and CPU1 displays this message on display device 7.

Next, CPU11 prescribes the exercise plan to be carried out by the user from that point. However, since the user's health state is initially not known, the standard target values stored in RAM12 are employed. Namely, assuming, for example, that the user is a 51 year old male, which is determined by the age and sex input by the user, then CPU11 reads out a total exercise duration for one week of 150 minutes and a target heart rate of 115. If the exercise capacity of the individual user, i.e., his maximal oxygen uptake quantity, can be ascertained, then the initial target settings may of course be carried out by a physician or other specialist, with the set value indicated to the user.

CPU11 then determines the frequency of exercise and the exercise duration per session from the targeted value for the total exercise duration for one week. In this case, for example, CPU11 determines that exercise will be carried out twice a day for five days. Accordingly, the preceding conditions are satisfied by having the user exercise 15 minutes each time, for a total of 30 minutes per day. CPU11 calculates the upper and lower limit values for pulse rate by determining limits in which it will not be a problem if the measured pulse rate during exercise deviates from the targeted heart rate just determined.

Next, CPU11 stores the exercise duration per session, the heart rate and its upper and lower limit values, and the frequency of exercise (5 times per week, twice daily) in RAM13, and then sends these values to portable portion 70. As a result, CPU1 then sequentially stores the relayed data in RAM3.

When all of the processing above is completed, CPU11 notifies portable portion 70 that all of the pre-settings for exercise performance are completed. CPU1 displays this message on display device 7. In addition, CPU1 also displays the details of the exercise to be performed (i.e., exercise to be performed five days a weeks, as two 15 minute daily sessions) on display device 7.

When the preceding is displayed, the user disconnects communications cable CB from portable portion 70, and connects connector covers 106a,106b to connectors 105a, 105b. As a result, the user is now able to move freely from the site of stationary portion 80 to another location.

Thereafter, the use carries out the indicated exercise. Namely, the user pushes button switch 114 of portable portion 70 to notify the device that he is starting exercise. The depression of this button is communicated to CPU1 via operational portion 506. CPU1 then reads out the clock time from watch circuit 10, and stores this as the exercise-start time in RAM3. CPU1 also sets watch circuit 10 to generate an interrupt after the elapse of the targeted exercise duration per session which is indicated by stationary portion.

Next, the user starts to exercise. Meanwhile, CPU1 sets the watch circuit 10 to generate an interrupt at prespecified time intervals (one minute, for example). As the user is exercising, the pulse rate and exercise quantity per minute are measured, and exercise guidance is provided to the user. This processing will now be explained in greater detail.

First, in order to calculate the total amount of exercise during the session, CPU1 initializes the memory area provided in RAM3 at [0]. Next, each time an interrupt is introduced, CPU1 takes up the pulse waves over a prespecified period only from sensor interface 505 and stores them in RAM3. The pulse rate is then calculated by the same procedure as described above.

Next, CPU1 calculates the amount of exercise, which is displayed in the form of calories. Since calories are approximated as the product of pulse rate and exercise duration, CPU1 multiplies the pulse rate obtained as described above by the time which has elapsed from the immediately preceding pulse rate measurement to the current pulse rate measurement. In this way, the exercise quantity is obtained. When calculating the exercise amount, it is typically the case that the immediately preceding pulse rate will differ from the current pulse rate. Therefore, it is acceptable to employ the average of these values.

Next, CPU1 reads out the details stored in the area of RAM3 for storing total exercise amount, determines the total exercise amount since the user began exercising by adding the exercise amount just obtained, and writes this information back to the aforementioned storage area. CPU1 stores the pulse rate obtained as described above, the total exercise amount through the current point in time, and the time of measurement which is read out from watch circuit 10, together in RAM3. These values are then displayed on display device 7.

The amount of exercise may be obtained as the product of exercise intensity and exercise duration. Accordingly, it is also acceptable to display the exercise amount obtained as this product in place of calories. In other words, the measured pulse rate and the exercise intensity satisfy the following well-known Karvonen equation, so that exercise intensity can be calculated from the pulse rate measured during exercise, the user's age and the resting pulse rate which are stored in RAM3, to obtain the amount of exercise.

$$\text{Measured pulse rate} = \\ \text{(pulse rate at rest)} + \{(220\text{-age}) - \text{pulse rate at rest}\} * \text{exercise intensity} \quad \ldots (1)$$

CPU1 checks whether or not the measured pulse rate deviates from the range determined by the upper and lower limit values for target heart rate as described above. If the pulse rate exceeds the upper limit, then a directive is displayed on display device 7 for the user to exercise a bit more moderately, while if the pulse rate falls below the lower limit, the user is directed to somewhat increase the intensity of exercise.

Accordingly, by displaying pulse rate and other information on display device 7, the user can increase or decrease the exercise being performed. At the same time, since it is possible to check whether or not the appropriate level of exercise is being performed, excessive or ineffective exercise is avoided. Thus, monitoring is carried out to ensure that the intensity of exercise is appropriate.

When an interrupt from watch circuit 10 is introduced after the elapse of the preset exercise duration, CPU1 outputs a directive to the user to stop exercising. The user either stops immediately, or continues until he reaches a more convenient stopping point. Then, the user presses button switch 114 again to notify portable portion 70 that he has stopped exercising. As a result, CPU1 takes up the current clock time from watch circuit 10, stores this as the exercise-stop time in RAM3, and ends pulse rate measurement and exercise guidance.

Then, in order to measure the post-exercise acceleration pulse waves, the user connects cellular portion 70 and stationary portion 90 via communications cable CB, and presses button switch 117. CPU1 then sequentially relays the pulse rates and total exercise amount from the start of exercise which were measured at each point in time and have been stored in RAM3, and the respective time of measurement, exercise-start times, and exercise-end times, to stationary portion 80. In synchronization with this, CPU11 writes the relayed data in detail in RAM13.

Next, CPU11 inspects in detail the pulse rate measured during exercise, and checks the degree to which the measured pulse rate deviates from the targeted heart rate and the upper and lower limits therefor. The total exercise time is then determined from the exercise-start time and exercise-stop time, and the degree to which this value deviates from the targeted exercise duration is checked. When there is a marked degree of deviation, the user is informed of this fact so that he knows that exercise was not carried out as directed. At the same time, the number of times the measured pulse rate deviated from the preset limits, the actual measured value of exercise duration, and the targeted value of exercise duration, are each relayed to portable portion 70 and displayed on display device 7.

CPU11 measures the acceleration pulse waves after exercise, following the same procedure as prior to exercise. The amplitude ratio d/a is calculated from this result, and stored in RAM13. Also, the pattern type of the post-exercise amplitude ratio d/a is determined, stored in RAM13, and displayed on display device 7.

Next, CPU11 compares the pre-exercise and post-exercise patterns. If the comparison reveals an improvement toward a type (1) pattern, or that the pattern has been maintained without change, then a message such as "health state improved" or "health state maintained" is relayed to portable portion 70, and display on display device 7 Additionally, it should be noted that it is of course also acceptable to directly compare the values of the amplitude ratios d/a, rather than comparing the pattern types.

On the other hand, if a comparison reveals that the pattern has worsened toward a type (6) pattern, then it may be viewed that the exercise just performed was excessive with respect to the user's physical condition on that day. Therefore, CPU11 adjusts at least one of the preset conditions for target heart rate, weekly exercise frequency, and exercise duration per session, so that exercise is made more moderate.

As the simplest method for adjusting exercise to be more moderate, the exercise target value may shifted up one age level on the table of target values shown in FIG. 21. For example, if the initial target value was for a user in his fifties, the target value may be shifted to the target value for a person in their sixties. Further, in the case where the user's target value has become the target value used for a person in their sixties, i.e., the maximum age class, as a result of gradually lowering the target value, the present invention may be designed to direct the user to consult with a physician, or, alternatively, to subsequently lower the total exercise duration per week by 10 minutes while decreasing the targeted heart rate by 5.

In the case where raising the target value, a procedure opposite to that described above may be followed. Namely, the targeted total exercise duration per week may be increased 10 minutes each week and the targeted heart rate may be increased by 5. Since heart rate (pulse rate) and exercise intensity are related as defined by equation (1), lowering the targeted heart rate corresponds to reducing the exercise intensity. As one example of a method for this adjustment, the three items (heart rate, frequency of exercise each week, exercise duration per session) described above may be suitably combined, and one target value from among these may be adjusted.

Once the above processing is finished, processing for prescribing an exercise plan prior to the start of exercise based on the new exercise target value, providing exercise guidance during the exercise session, evaluating the health state and the details of the executed exercise after exercise is completed, and readjusting the target value, is repeatedly carried out. After the above-described training has been carried out for 10 weeks, for example, a physician or other specialist evaluates the user's exercise capacity. Based on the results of this evaluation, the initial values for new exercise target values are set in the device.

By providing an appropriate exercise plan and guidance during exercise in this way, it is possible to shift the user's physical condition toward a better state safely and without excess.

In this embodiment, display commands are input via keyboard 16, and CPU11 displays the various data stored in RAM13 on display device 17. This data includes the pre-exercise amplitude ratio d/a, post-exercise amplitude ratio d/a, pulse rate measured at each point in time, the total exercise amount from the time exercise started, total exercise duration, graph displays of the transition in pulse rate over time, and the pulse waveforms measured before and after exercise.

As a method for evaluating the exercise performed by the user, an approach as discussed below may be considered.

FIG. 8 shows an example of the relationship between the total amount of exercise performed by the user since the exercise session began and the rate of change in amplitude ratio d/a before and after exercise. As shown in this figure, when the amount of exercise is little, then the rate of change in amplitude ratio d/a is small, with a value of about +5% or less obtained (region I in FIG. 8). When the amount of exercise is greater than this, then the rate of change in amplitude ratio d/a gradually increases above +5%. Subsequently, the rate of change begins to fall after a certain point, until it again is around +5% (region II in FIG. 8). When the amount of exercise is increased further, the rate of change in amplitude ratio d/a falls further, dropping below +5% to around −10% (region III in FIG. 8). A further increase in the amount of exercise leads to a further decline in the rate of change in amplitude ratio d/a, to below −10% (region IV in FIG. 8).

CPU11 carries out the exercise evaluation each time a measurement is made, based on the relationship between the total amount of exercise since the exercise session began and the rate of change in amplitude ratio d/a In order to do this, CPU11 determines the difference between the post-exercise amplitude ratio d/a and the pre-exercise amplitude ratio d/a, and divides this difference by the pre-exercise amplitude ratio d/a, thereby calculating the rate of change in amplitude ratio d/a. The thus-obtained rate of change in amplitude ratio d/a and the exercise amount measured during the session are plotted on the graph in FIG. 8. CPU11 then makes an evaluation of the exercise performed by the user according to which region I–IV this plot is positioned in.

Namely, if the plot is in region I of FIG. 8, then CPU11 determines that exercise was too moderate. If the plot is in region II, then CPU11 determines that exercise was appropriate. If the plot is in region III, then CPU11 determines that exercise was slightly in tense. And if the plot is in region IV, then CPU11 determines that exercise was too intense. Based on these results, CPU11 adjusts the target values for the exercise which is to be performed next, and carries out the following processing.

For example, it the case where the evaluation result indicates that the plot is in region I, then the target values are shifted down one stage to a lower age category from the age categories shown in FIG. 21. Similarly, in the case where the evaluation result indicates that the plot is in region III or IV, then the target values are shifted up one or two stages to a higher age category in the age categories shown in FIG. 21.

Further, with respect to an evaluation result indicating that the plot is in regions I, II, III or IV, CPU11 relays the messages "exercise too mild", "exercise appropriate", "exercise slightly too strenuous", and "exercise too strenuous," respectively, to portable portion 70. The message is then displayed on display device 7, so that the user is notified of the results of the exercise evaluation.

The preceding embodiment described the case where the amplitude ratio d/a alone was employed. However, by employing an evaluation method which uses both amplitude ratio d/a and amplitude ratio c/a, it is possible to carry out an exercise evaluation which is even more accurate. Namely, if, for example, the value of the amplitude ratio d/a is 20%, then a determination can be made from FIG. 2(b) that the waveform of the acceleration pulse wave is associated with a pattern (2) type waveform. On the other hand, if the value of amplitude ratio d/a is 80%, then it is possible to specify that the acceleration pulse waveform is associated with one of patterns 4 through 6. Reference is then made to the value of the amplitude ratio c/a to determine which is the pattern from among these. For example, if the value of amplitude ratio c/a is 30%, then it is possible to determine from FIG. 2(b) that the acceleration pulse waveform is associated with a pattern (5) type waveform.

Embodiment 7

Information such as the power spectrum obtained from heartbeat variation has begun to be used in the diagnosis and treatment of various ailments such as heart disease, central nerve disorders, peripheral nerve disorders, diabetes, high blood pressure, cerebrovascular disease, sudden death and the like in recent years. Accordingly, this embodiment obtains the LF (low frequency), HF (high frequency) and RR50 indicators from an analysis of the pulse tidal wave corresponding to the tidal wave in heartbeat variation, and employs these as indicators of the user's physical state in place of the indicators obtained from the acceleration pulse wave. An explanation will first be made of the significance of these indicators.

In an electrocardiogram, the interval between the R wave of one heart beat and the R wave of the next heart beat is referred to as the RR interval. This RR interval is a numerical value which serves as an indicator of the functioning of the autonomic nervous system in the human body. FIG. 9 shows heartbeat and the RR interval obtained from the waveform of this heartbeat in an electrocardiogram. As may be understood from this figure, an analysis of the measured results in an electrocardiogram reveals that the RR interval varies over time.

On the other hand, variation in blood pressure measured at the radius artery or the like, is defined as the variation in blood pressure at each beat from contraction to relaxation of the heart, and corresponds to variation in the RR interval in an electrocardiogram. FIG. 10 shows the relationship between the electrocardiogram and blood pressure. As may be understood from this figure, the blood pressure during each contraction and relaxation in a heart beat can be measured as the maximum value of arterial pressure, and the minimum value immediately preceding this maximum value in each RR interval.

By carrying out spectral analysis of the variation in heart beat or blood pressure, it may be understood that the variations are composed of waves having a plurality of frequencies. These may be classified into the following three types of variation components.

1. HF (high frequency) component which is the variation coinciding with respiration
2. LF (low frequency) component which varies with a periodicity of around 10 seconds
3. Trend which varies with a frequency which is lower than the measurement limits The RR interval between neighboring pulse waves is obtained for each measured pulse wave, and the discrete value of the obtained RR interval is interpolated using a suitable method (for example, 3rd order spline interpolation) (see FIG. 9). An FFT operation is carried out on the curved line after interpolation, followed by spectral analysis. As a result, it is possible to pick out the variation component as a peak on the frequency axis. FIG. 11(a) shows the waveform of variation in the RR interval of a measured pulse wave and the waveform of each of the components of variation in the case where the waveform of variation is segregated into the three frequency components noted above. FIG. 11(b) shows the results of spectral analysis on the waveform of variation in the RR interval shown in FIG. 11(a).

As may be understood from this figure, peaks are apparent at two frequencies near 0.07 Hz and 0.25 Hz. The former frequency value is the LF component, while the latter is the HF component. The trend component cannot be read in the figure because it is below the limit for measurement.

The LF component is related to the activity of the sympathetic nervous system. The larger this component, the greater the increase in tension. On the other hand, the HF component is related to the activity of the parasympathetic nervous system. The larger the amplitude of this component, the more relaxed the state.

The amplitude values for the LF and HF components will vary according to the individual. Accordingly, with this in mind, the proportion LF/HF, which is the ratio of the amplitudes of the LF and HF components, is useful to estimate the state of the subject. When the value of LF/HF is large, than the degree of tension is high, while when LF/HF is small, the degree of tension is low indicating the subject is relaxed.

RR50 is defined by the fixed number at which the absolute value of the pulse wave interval corresponding to the RR interval for two consecutive heart beats varies by 50 milliseconds or more, when measurements of pulse wave are carried out over a prespecified period of time. The larger the value of RR50, the more sedate the subject is, while the smaller the value of RR50, the more aroused the subject is.

There is, by the way, a correlation between these indicators and the physical state of the user.

As a result of lowering functioning of the parasympathetic nervous system and placing the sympathetic nervous system in a position of dominance through intensified training, it is possible to create a condition which resembles the physical state of a patient afflicted with a disease such as described above. If the intensified training is then suspended, and the change in the aforementioned indicators is observed while the body recovers, the HF component is found to increase as the day passes, while the LF/HF value tends to fall as the day goes by.

In other words, as the body's state recovers, the HF component or the LF/HF value increase or decrease from a value indicating a state of tension to a value indicating a state of relaxation. Accordingly, it may be hypothesized that by observing not only the HF component and LF/HF value, but also the LF component and RR50 value, it is possible to judge whether or not the body state is good by observing the increase and decrease in the values in each of the indicators. Accordingly, these indicators may be used in place of amplitude value d/a.

The exercise support device according to this embodiment will now be explained. In this embodiment, one of the four indicators described above is used in place of the amplitude ratio d/a employed in Embodiment 6. The structure of the device is the same as that in Embodiment 6. Therefore, the following explanation will focus on those aspects of the device's operation which are specific to this embodiment.

Additionally, the acceleration pulse waveform was divided into 6 patterns in the sixth embodiment. In this embodiment, however, the indicators are divided into a number of grades according to the value thereof. However, the indicator values may of course be used as is, without division into these grades.

Prior to beginning exercise, the user connects portable portion 70 and stationary portion 80, and, after confirming that he is in a state of repose, presses button switch 117. As a result, CPU1 takes up the pulse waveform over a prespecified period of time, and calculates the resting pulse rate from the pulse waveform. If the user's age and sex have not yet been input, the user is directed to input these values. Then, the pulse waves over the specified time interval, the resting pulse rate, and the user's age and sex are each stored in RAM3. Next, CPU1 and CPU11 operate together to relay the data from RAM3 to RAM13.

Next, CPU11 begins processing to calculate the aforementioned four indicators based on the relayed pulse waveforms. An explanation of this processing follows below.

First, in order to extract the maximum points from the pulse waveform, CPU1 calculates the time derivative of the pulse waveform stored in RAM13, and obtains all times at which there is a pole in the waveform by determining the times where the time derivative is zero. Next, CPU1 determines whether each pole is a maximum or minimum, from the slope of the waveform about the pole (i.e., the time derivative). In other words, for a given pole, CPU1 calculates the moving average of the waveform slope over a prespecified time interval preceding the pole. If this moving average is positive, then the pole is a maximum, while if the value is negative, the pole is a minimum.

Next, for each extracted maximum point, CPU11 determines the minimum point present immediately preceding it. The pulse wave amplitudes at the maximum and minimum points are read out from RAM13, and the difference between them is determined. If this difference exceeds a prespecified value, then the time at which this maximum point appeared is designated a pulse wave peak. After carrying out peak detection for all the pulse waveforms taken up, the time interval between two adjacent pulse wave peaks is calculated based on the time at which these peaks occur (corresponding to RR interval between heartbeats).

The value of the obtained RR interval is discrete along the time access. Accordingly, a curved line such as shown in FIG. 11(a) is obtained by interpolation between neighboring RR intervals using a suitable interpolation method. Next, a spectrum such as shown in FIG. 11(b) is obtained by carrying out FFT processing on the interpolated curved line. Processing to determine maximums is carried out in the same manner as carried out on the pulse waveform, to obtain the frequencies in the spectrum corresponding to the aforementioned maximum and minimum values. The maximum value obtained in the low frequency region is defined as the LF component, while the maximum value obtained in the high frequency region is defined as the HF component. Further, the amplitudes of these components are obtained and the amplitude ratio LF/HF is calculated. The time difference in neighboring RR intervals is sequentially obtained based on the RR interval obtained above. Next, a check is made of each of these time differences to confirm whether or not the time difference exceeds 50 milliseconds, and the fixed number of time differences exceeding 50 milliseconds is counted and set as RR50.

CPU11 determines the grade to which the index value obtained as above is associated. The determined grade and the value of the index are stored in RAM13, and displayed on display device 17. Next, in the same manner as in Embodiment 6, CPU11 carries out preparations for prescribing the subsequent exercise plan. Namely, CPU11 determines the exercise duration per session, the target heart rate and upper and lower limit values therefor, and the exercise frequency, and stores these in RAM13. Next, in cooperation with CPU1, CPU11 sends these values to RAM3.

When the above processing is complete, CPU11 sends notice that pre-setting is completed together with the details of the exercise plan to portable portion 70. These are displayed on display device 7. As a result, after separating portable portion 70 and stationary portion 80, the user presses button switch 14, notifying the device that exercise is beginning. Subsequent operations are carried out as in Embodiment 1. Namely, CPU1 calculates the user's pulse rate and the total amount of exercise from the start of the session, writes these together with the time at which the measurement were made in RAM3, and displays this information on display device 7. Additionally, CPU1 carries out exercise guidance based on the measured pulse rate, the targeted pulse rate, and the upper and lower limit values therefor.

After the elapse of the targeted exercise duration, CPU1 directs the user to stop exercising, and ends measurement of the pulse rate, etc. and exercise guidance when the user pushes button switch 114. Next, the user connects portable portion 70 and stationary portion 80, and presses button switch 117. As a result, CPU11 calculates the above indicators in the same way as prior to the start of exercise, determines a grade for the indicators, and stores the grade values and indicator values in RAM13. Then, working in cooperation with CPU1, CPU11 uploads the data measured by portable portion 70 from RAM3 to RAM13. CPU11 then determines whether the measured pulse rate and the total exercise duration deviate notably from their respective target values, and notifies the user in this event.

Next, CPU11 compares the index values before and after exercise, and notifies the user that his health state is improved, unchanged or worse. Where using LF and LF/HF as standards for judging whether physical state has improved or deteriorated, a decrease in the value due to exercise indicates improvement, while an increase indicates deterioration. In contrast, when HF or RR50 values are employed, a decrease indicates deterioration, while an increase indicates improvement.

When a determination is made that the user's health state has deteriorated, CPU11 adjusts the exercise plan so that more moderate exercise is performed. Thereafter, in the same manner as above, the exercise plan, guidance and diagnosis cycle is repeated.

Additionally, it should be noted that while one indicator from among the four described above was employed in this embodiment, it is acceptable to use any number of these indicators comprehensively.

Modifications

The present embodiment is not limited to the aforementioned embodiments. For example, a variety of modifications as follow are also possible.

Modification 1

In the preceding embodiments, pulse waves were measured at the base of the user's finger. However, measurement of pulse waves in the present invention is not limited to this position. For example, the pulse wave may be measured at the radius artery or in the vicinity thereof.

Figure 5A:
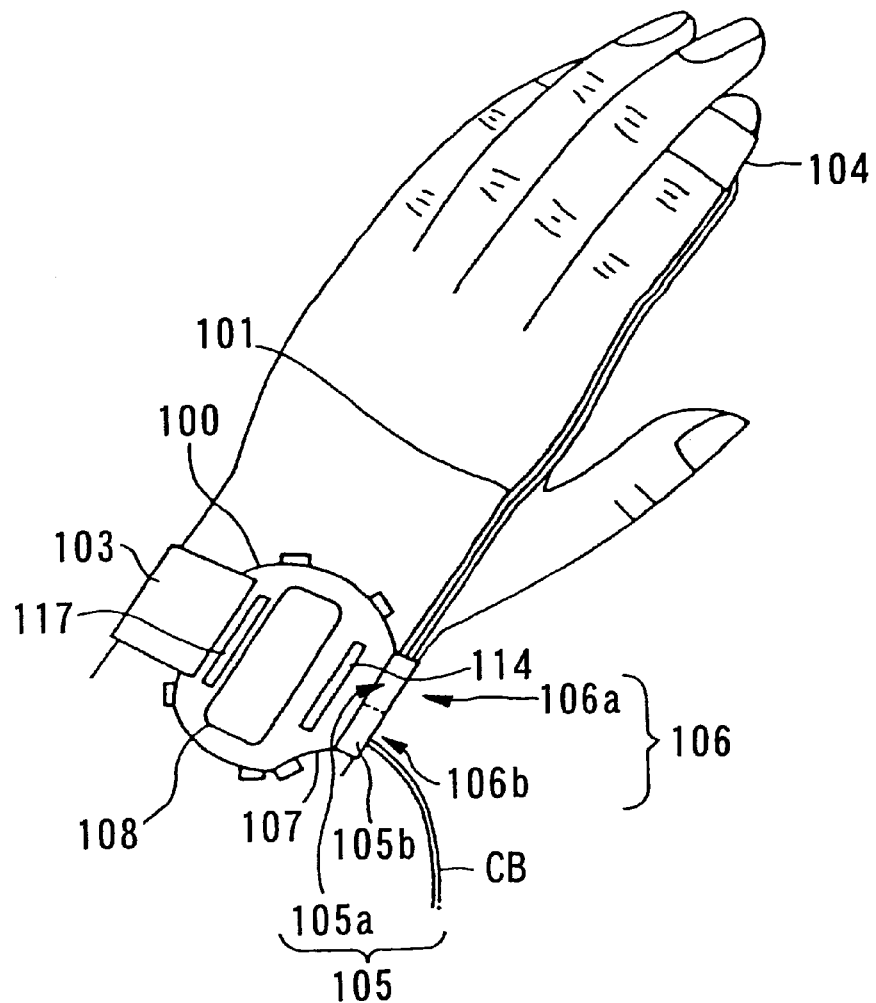
FIGS. 5(a) and 5(b) show another arrangement for the case where the device is incorporated in a wristwatch.
Figure 5B:
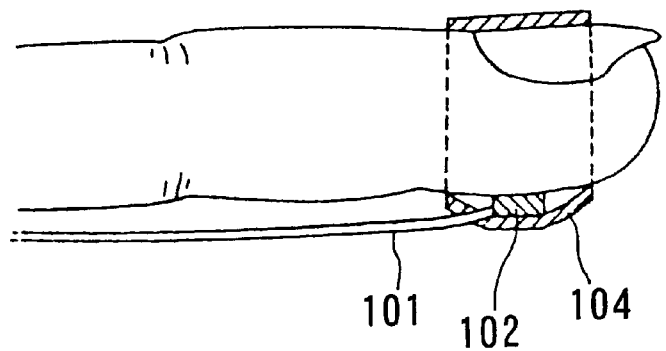

Additionally, as one modification in this regard, an arrangement such as shown in FIGS. 5(a) and 5(b) may be considered in which a sensor unit 102 and band 104 for holding the sensor in place are attached to the fingertip, and the fingertip plethysmogram is measured.

Figure 6:
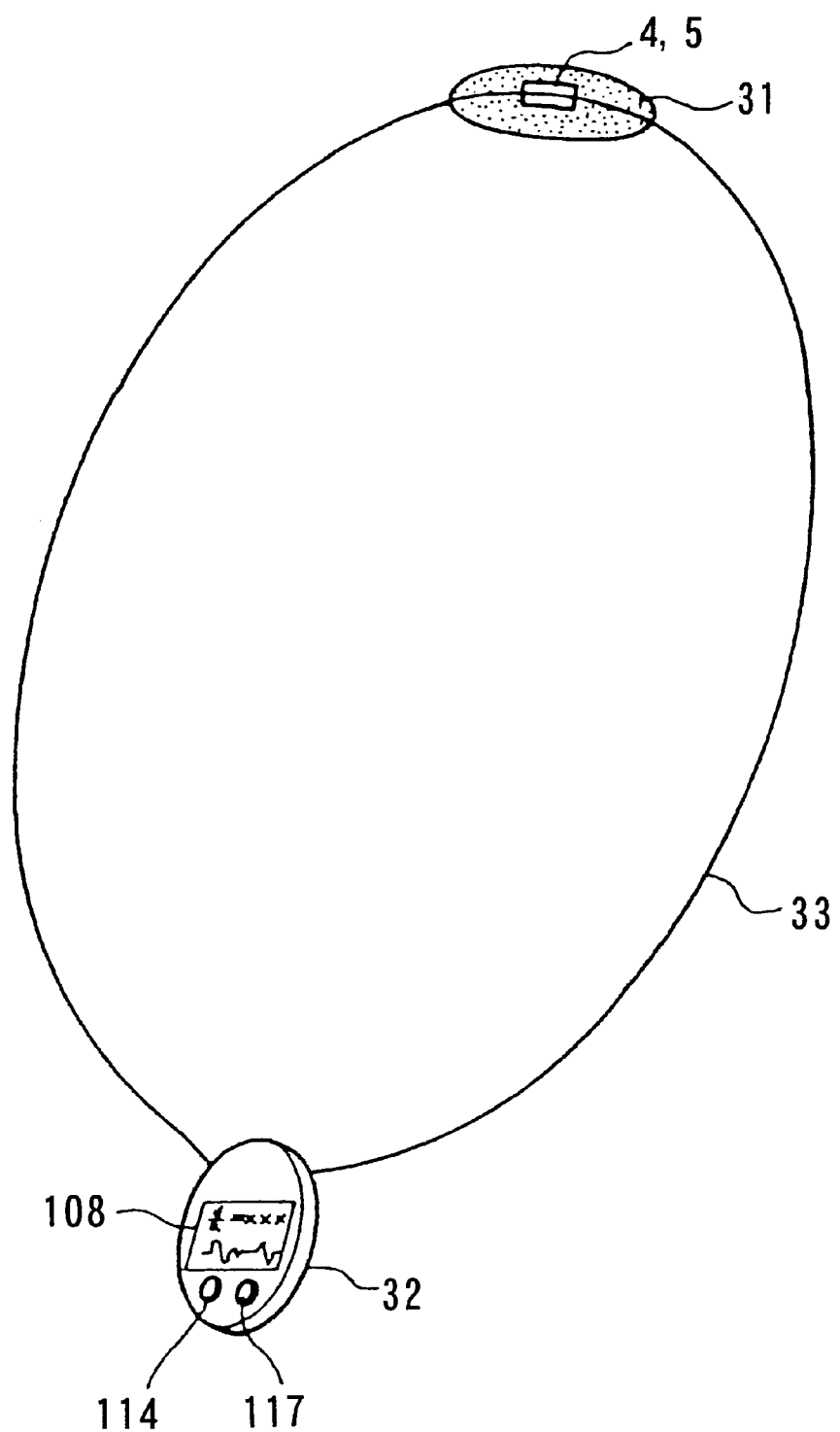
FIG. 6 shows the case where the device is incorporated in a necklace.

Next, a second arrangement such as shown in FIG. 6 in which the device is incorporated in an accessory such as a necklace may be considered. In this figure, the parts of the device which are equivalent to those shown in FIGS. 3(a) and 3(b) have been assigned the same numeric symbol and will not be explained here.

In this figure, 31 is a sensor pad, and is comprised, for example, of a shock absorbing material such as a sponge. The pulse wave sensor 4/acceleration sensor 5 shown in FIG. 1 (or pulse wave sensor 4 shown in FIG. 19) are attached in the middle of sensor pad 31. As a result, when the necklace is worn around the neck, this sensor comes in contact with the skin surface on the back of the neck, to enable measurement of the pulse waves.

The CPU1, ROM2, RAM3, sensor interface 6, display control circuit 8, and watch circuit 9 shown in FIG. 1 (or the CPU1, ROM502, RAM3, sensor interface 505, display control circuit 8, external interface 509 and watch circuit 10 shown in FIG. 19) are incorporated inside a brooch-shaped case 32. A connector (not shown in the figures) is provided to the back of case 32 for attachment of communications cable CB, while a conductive wire, corresponding to cable 101 shown in FIG. 3, is embedded in chain 33. Moreover, since watch functioning is not necessary in this embodiment, display device 7 may be composed of just dot display region 108-D which is capable of graphic display.

Figure 7:
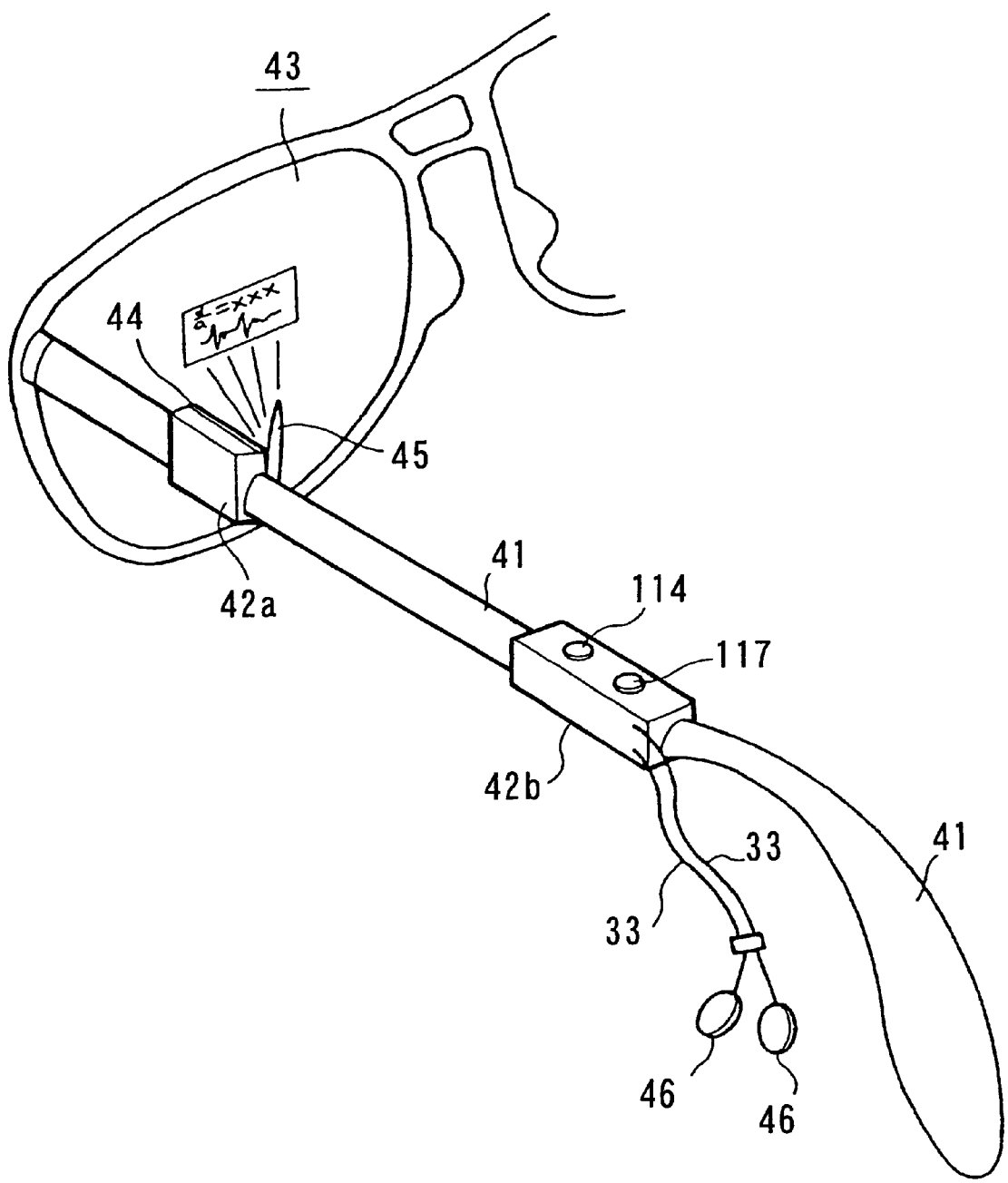
FIG. 7 shows the case where the device is incorporated in a pair of eyeglasses.

Next, a third arrangement may be considered in which the device is incorporated into a pair of eye glasses such as shown in FIG. 7. The parts of the device which are the same as those pictured in FIGS. 3(a) through 6 have been assigned the same numeric symbol, and an explanation thereof will be omitted here.

As shown in FIG. 7, the main body of the device is attached to the stems 41 of a pair of eyeglasses. The main body of the device is divided into cases 42a and 42b which are connected via a lead wire embedded inside stems 41. The lead wire may also extended along the outside of stems 41.

A liquid crystal panel 44 is provided across the entire lateral surface of the lens 43 side of case 42a. A mirror 45 is fixed at a specific angle at one edge of this lateral surface. A drive circuit for liquid crystal panel 44 which includes a light source (not shown) is incorporated in case 42a. The light emitted from this light source passes via liquid crystal panel 44, and is reflected at mirror 45 to incident on lens 43 of the eyeglasses. Accordingly, in this arrangement, lens 43 may be viewed to have the functions of the display device 7 shown in FIGS. 1 and 19.

The CPU1, ROM502, RAM3, sensor interface 505, display control circuit 8, external interface 509, and watch circuit 10 are incorporated in case 42b, with a connector (not shown) for connecting communications cable CB provided to the bottom surface thereof. Pulse wave sensor 4 is housed in pads 46, 46, and is fixed to the ear by the holding of the earlobe between the pads. Accordingly, in this embodiment, the pulse wave at the earlobe is measured.

In addition, while not shown in the figures, the various button switches shown in FIGS. 3(a) and 3(b) are provided to the embodiments shown in FIGS. 6 through 7, and are used for inputting the user's age and sex, etc.

Modification 2

In the third and fourth embodiments, physiological state is extracted from the pulse waves. However, the present invention is not limited this arrangement.

Namely, since heart rate (pulse rate) and exercise intensity are related as indicated by Equation (1) above, it is acceptable to use exercise intensity in place of heart rate when carrying out the exercise plan.

Further, when performing an exercise plan, it is not necessary to use all of the parameters of target pulse rate, exercise duration per session and exercise frequency. Rather, it is acceptable to use one or a combination of two of these.

Additionally, in the third and fourth embodiments, the standard value for the exercise target value was determined based on age and sex, as shown in FIG. 21. However, it is also acceptable to take into consideration resting pulse rate and the like when determining the standard value for the exercise target value.

In the third and fourth embodiments, portable portion 70 and stationary portion 80 were connected using a communications cable CB. However, in addition, it is also acceptable to employ optical communications using infrared or near infrared, or to employ wireless communications using radio waves. In this case, all information displayed on display device 17 of stationary portion 80 is displayed on display device 7 of portable portion 70. In this way, the connection between portable portion 70 and stationary portion 80 is rendered wireless, thereby substantially reducing the burden on the user since there is no need to bother with connecting a cable.

Additionally, it is also acceptable for the personal computer to directly measure the acceleration pulse wave, rather than providing a pulse wave sensor to the personal computer and then sending pulse waveform data from portable portion 70 to stationary portion 80.

Moreover, each of the preceding embodiments employed the acceleration pulse wave. However, the reason for this is simply that the acceleration pulse wave is the most widely known, and is easy to analyze. Accordingly, it is of course acceptable to employ the pulse wave's original waveform, the first derivative thereof, or a derivative higher than the acceleration pulse wave, in the present invention.

Figure 12A:
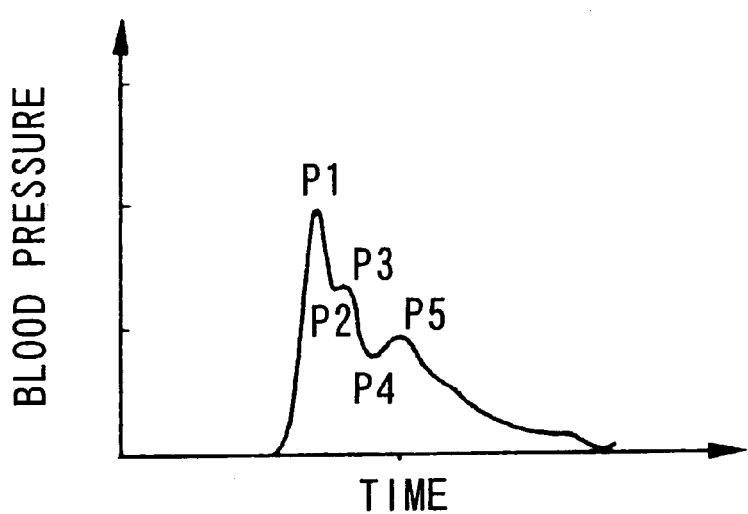
Figure 12B:
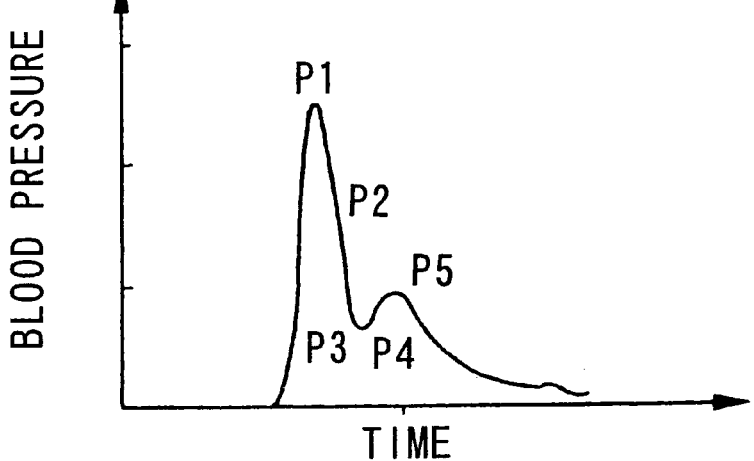
Figure 12C:
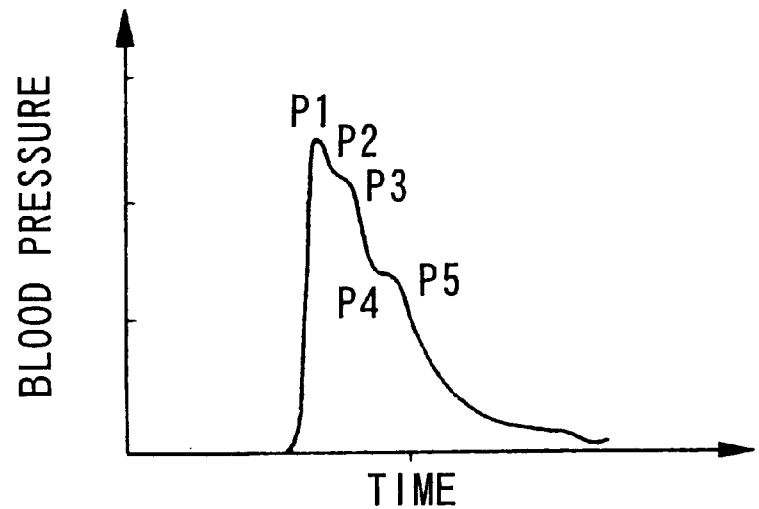

As one example of this approach, we will briefly explain the case where the original waveform of the pulse wave is employed. FIG. 12(a) and 12(b) shows a typical original waveform of a pulse wave. FIG. 12(a) is a so-called "normal wave," characterized in having three peaks. P1–P5 in this figure indicate inflection points (peaks) in the pulse wave. FIG. 12(b) shows a so-called "smooth wave," characterized in having two peaks. Finally, FIG. 12(c) is a so-called "violent wave."

With regard to the relationship between each of these pulse waves and exercise, the normal wave shown in FIG. 12(a) is typically seen prior to exercise. However, this wave may also be observed after completion of exercise, if the exercise carried out was too mild. In contrast, when exercise of the appropriate intensity is performed, then the smooth wave shown in FIG. 12(b) is typically seen after completion of exercise. On the other hand, when the exercise performed is excessive, then the violent wave shown in FIG. 12(c) is observed after the completion of exercise.

Accordingly, when employing the original waveform of the pulse wave, it is understood that an evaluation of the user's exercise may be carried out by determining whether the post-exercise pulse waveform is a normal, smooth or violent wave.

In order to ascertain the pulse wave characteristics by extracting inflection points P1–P5 from the measured pulse wave, a method may be employed such as disclosed in Japanese Patent Application Hei 5-197569 (Stress Evaluation Device and Physiological Age Evaluation Device) which was previously submitted by the present inventors. An overview of this method follows below.

Using this method, the following information is collected for the waveform of each beat in the pulse wave, to extract the pulse wave characteristics. Namely, as shown in FIG. 13:

1) Blood pressures $y_1$–$y_5$ at inflection points P1–P5 which sequentially appear in each beat of the pulse wave
2) Elapsed time $T_1$–$T_5$ until each inflection point P1–P5 appears, and elapsed time $T_6$ until the pulse wave of the next beat rises, where the pulse wave start time $t_0$, which is the point in time when the pulse wave starts to rise, is employed as the standard
3) Determination of whether each inflection point P1–P5 is a maximum or a minimum Elapsed time $T_1$–$T_6$, blood pressure $y_1$–$y_5$, determination of whether each inflection point is a maximum or a minimum, and the other pulse wave characteristics for normal, smooth and violent waves, respectively, are prestored in the ROM12 shown in FIG. 19.

Next, CPU1 or CPU11 checks the results of the above operations, and sets inflection points where zero was output for the time derivative of the waveform. For each of these points, CPU1 or CPU11 then obtains the clock time at which the waveform was collected and the blood pressure (corresponding to blood pressures $y_1$–$y_5$).

Next, each inflection point is determined to be a maximum or a minimum by referring to the slope information. In other words, when the slope information obtained for a given inflection point is positive, then that inflection point is a maximum. Conversely, when the slope information is negative, the inflection point is a minimum.

When detecting inflection points, CPU1 or CPU11 determines the blood pressure at that inflection point and the blood pressure at the immediately preceding inflection point. The thus-obtained difference is stored in RAM13 as stroke information.

After the above processing has been carried out for all of the pulse waves obtained during the duration of measurements, CPU1 or CPU11 carry out processing to separate the pulse wave into single beats. First, CPU1 or CPU11 reads out the slope and stroke information for each inflection point from RAM13, and selects the positive stroke information from among the read out stroke information. Next, starting with the largest stroke value, CPU1 or CPU11 selects a prespecified number of stroke data. From among the selected stroke information, CPU1 or CPU11 then selects the stroke information corresponding to the middle of the range, and sets this as the rising portion of each beat in the pulse wave. As a result, the start time of this rise in the pulse wave can be obtained as the pulse wave start time $t_0$.

In this way, inflection points P1–P5, maximum/minimum discrimination corresponding to these inflection points, and blood pressures $y_1$–$y_5$ at each of these inflection points are determined. Further, elapsed time $T_1$–$T_5$ can be calculated by determining the difference between the pulse wave start time $t_0$ and the waveform collection time at each inflection point. Similarly, elapsed time $T_6$ for each beat in the pulse wave can be obtained by determining the difference between the pulse wave start times $t_0$ of beats in adjacent pulse waves.

By comparing the measured pulse wave and the pulse wave prestored in ROM12 with respect to elapsed time $T_1$–$T_5$, blood pressure $y_1$–$y_5$, and maximum/minimum discrimination at inflection points P1–P5, it is possible to select the pulse wave type (normal, smooth, violent) which most closely fits the measured pulse wave. An evaluation of the exercise performed by the user can then be made based on the determination of the pulse wave type. Accordingly, if, for example, a violent wave is observed as the pulse waveform following exercise, the exercise target value can be lowered for the subsequent exercise plan.

Modification 3

The preceding embodiments were designed to provide a variety of notices to the user by means of a message display. However, it is also acceptable to employ a sound to provide this notification. For example, in the case where the device is incorporated in a wristwatch, the alarm function which is already part of the watch may be used. Moreover, even in the case where the device is incorporated in other types of portable devices, a sound source employing a piezoelement or speaker may be provided so that notification may be realized using an alarm or even a voice message. By carrying out notification using a sound in this way, full employment of the device is possible even for a visually impaired person. Moreover, since this arrangement removes the inconvenience of having to regularly look at the message display during exercise, it may be deemed preferable even for the normal user who has no visual impairment.

In addition, a modification may be considered in which the type or pitch of the sound generated is varied according to the results of the exercise evaluation or the type of directive given to the user, so that the user can recognize differences. It is also acceptable to employ messages and sound together.

In the case of a hearing-impaired individual, a modification which relies on sensation may be employed in place of messages or sounds. For example, the user can be notified by means of a vibration, by providing a structure in which a vibration plate is attached to the back of a wristwatch and vibrated, or the entire wristwatch vibrates. By varying the strength and duration of the vibration, notification of a variety of states can then be accomplished in the same way as where messages or sounds are employed.

Modification 4

In the first embodiment, acceleration sensor 5 was disposed near pulse wave sensor 4. In reality, however, acceleration sensor 5 may be attached anywhere on the user's body.

Modification 5

In the sixth and seventh embodiments, cable 101 and cable CB were designed to be independently attachable to connectors 105a,105b on device main body 100. However, the arrangement for attaching these cables is not limited thereto. Other arrangements for the purpose of connecting these cables to the wristwatch connector will now be explained. Additionally, it should be noted that the structure of the connectors explained below represents an improvement to the connectors disclosed in Japanese Patent Application First Publication No.: Hei 7-166551 (Title: Wristwatch-Type Pulse wave Measuring Device and Pulse wave Information Processing Device) submitted earlier by the present inventors.

Figure 25:
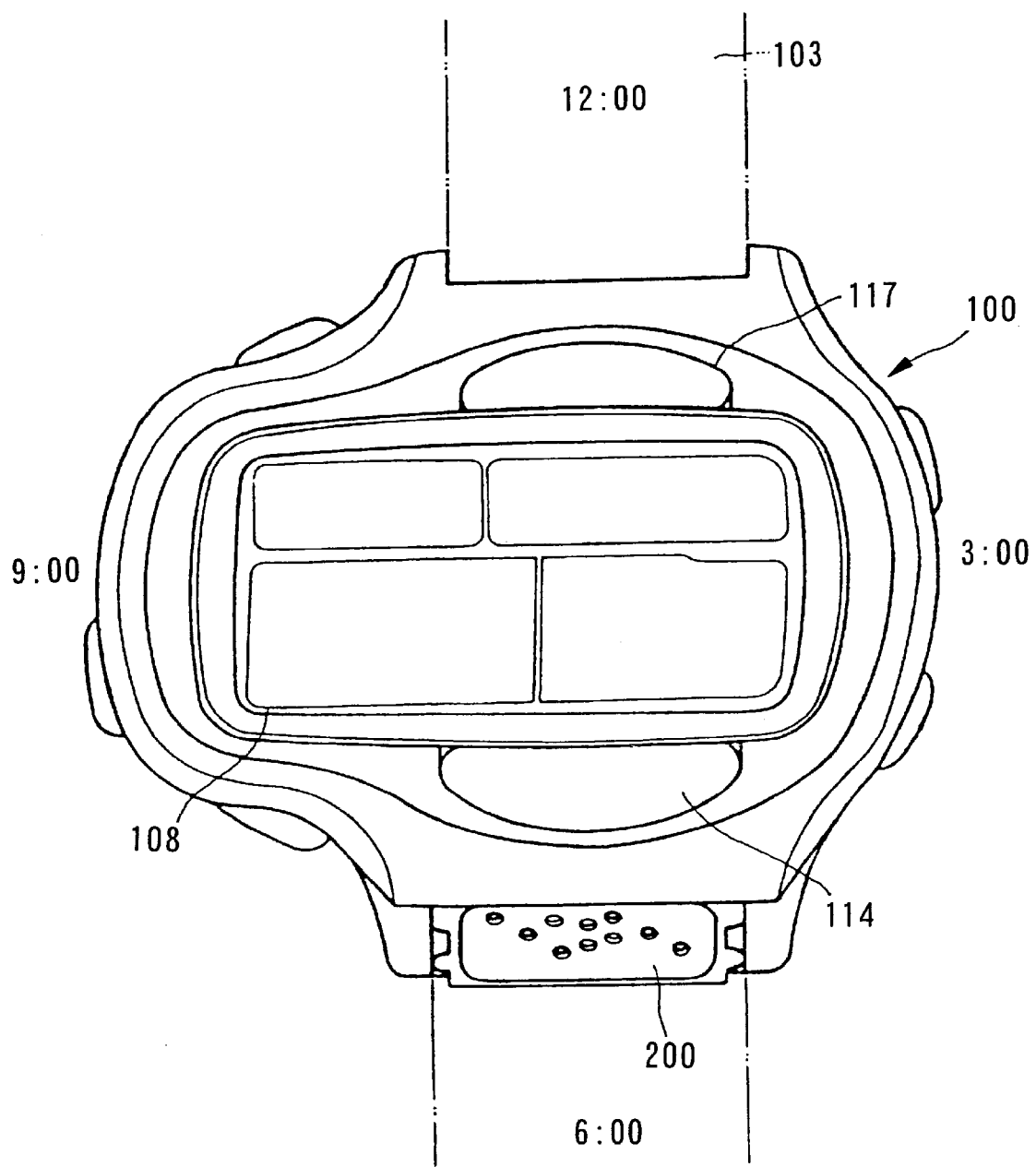
FIG. 25 is an upper view in which the wristwatch shown in FIG. 24 is enlarged.
Figure 26:
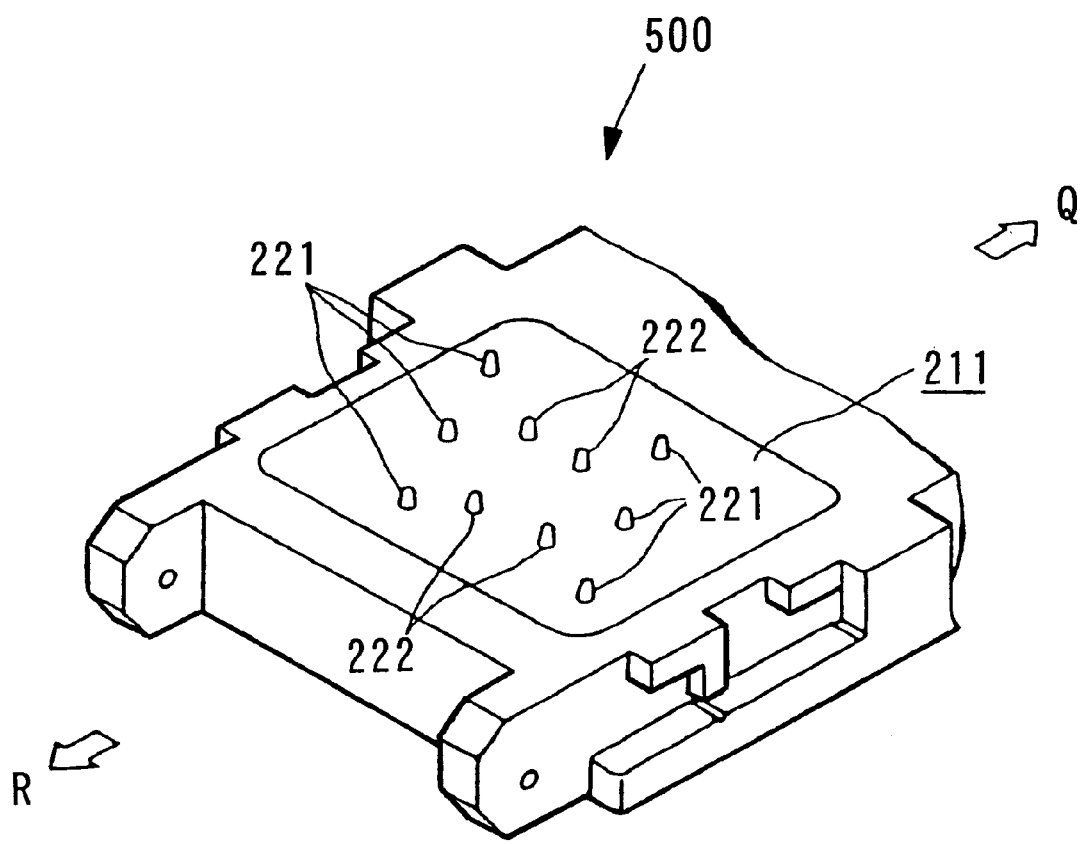
FIG. 26 is a perspective view of connector 500 on the wristwatch.

FIG. 25 is an enlarged view of the wristwatch shown in FIGS. 3 through 5, as seen from the upper surface thereof. Parts which are in common between these figures have been assigned the same numeric symbol, and an explanation thereof has been omitted. In FIG. 25, the cables are shown in a state of release, with the numeral 200 indicating the connector. FIG. 26 is a squint view showing an enlarged view of connector 500. As shown in this figure, terminals 221,222 are provided to the upper surface 211 of connector 500 for electrically connecting the pulse wave sensor 4 and communications cable CB in FIG. 19 to portable portion 70.

Figure 27A:
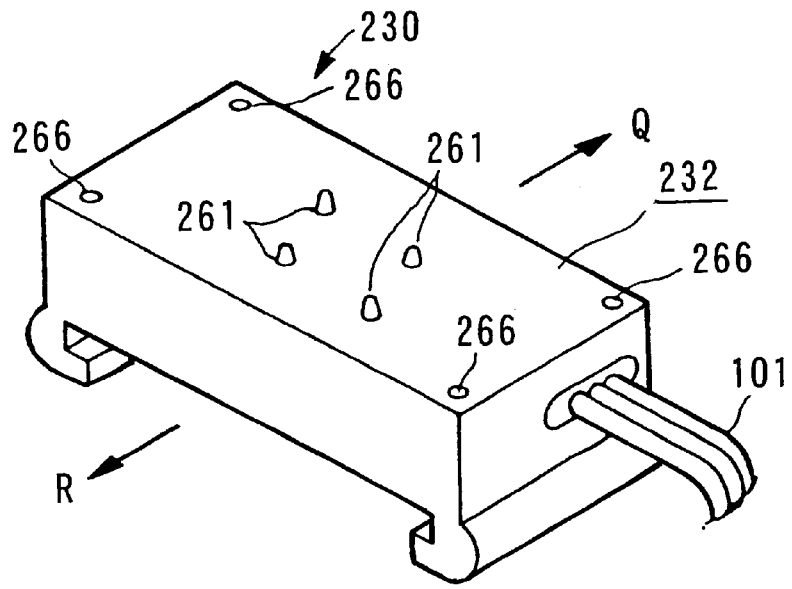
FIGS. 27(a) and 27(b) are perspective views of connector piece 230 which attaches to the wristwatch.
Figure 27B:
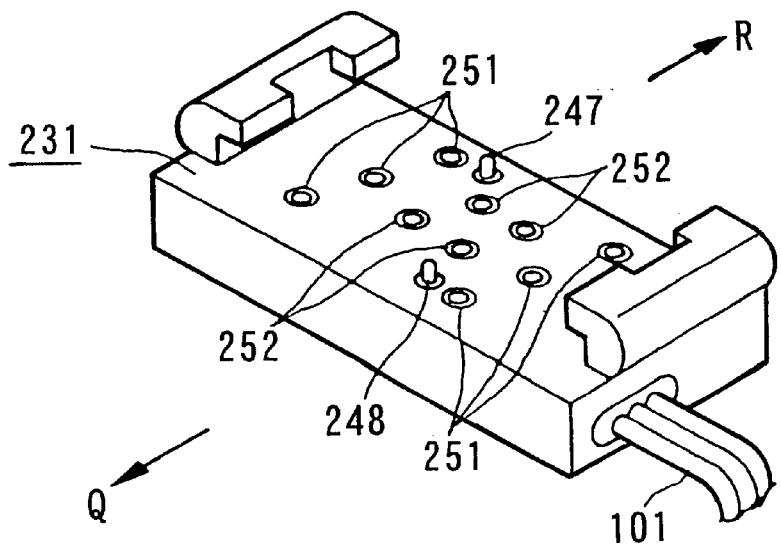

FIGS. 27(a) and 27(b) are perspective views of connector piece 230 which is attached to connector 500. Cable 101 is attached to connector piece 230. Movable pins 247–248, which operate a circuit (not shown) for preventing any effect from static electricity when cable 101 is connected, and electrodes 251,252, which electrically connect terminals 221,222, are formed to the bottom surface 231 of connector piece 230. In addition, a terminal 561, which has an electrical connection with connector piece 503 (explained below), is formed in the upper surface of 232 of connector piece 230, and openings 266 are formed in the four corners thereof.

To attach connector piece 230 to connector 500, connector piece 230 is pressed toward connector 500, and then slid in the direction indicated by arrow Q. As a result, terminals 221,222 are electrically connected with respect to electrodes 251,252. To remove connector piece 230 from connector 500, connector piece 230 is slid in the direction of arrow R, and then lifted up.

Figure 28A:
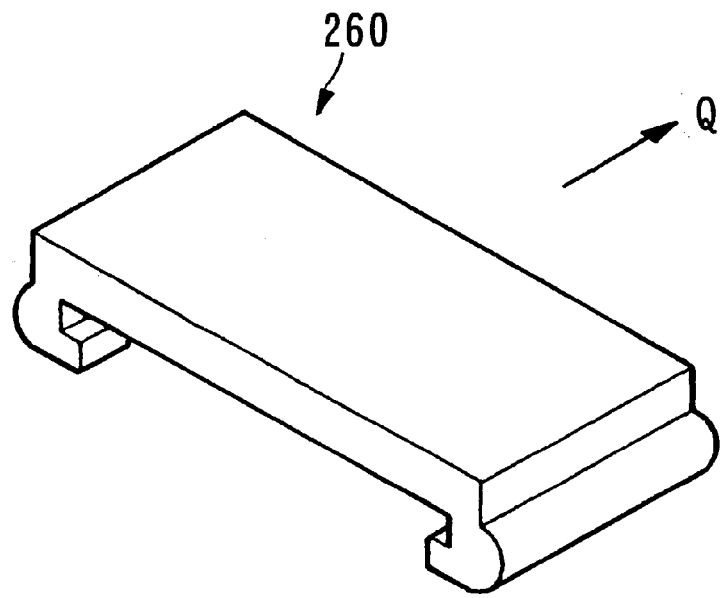
FIGS. 28(a) and 28(b) are perspective views of connector cover 260 which attaches to the wristwatch.
Figure 28B:
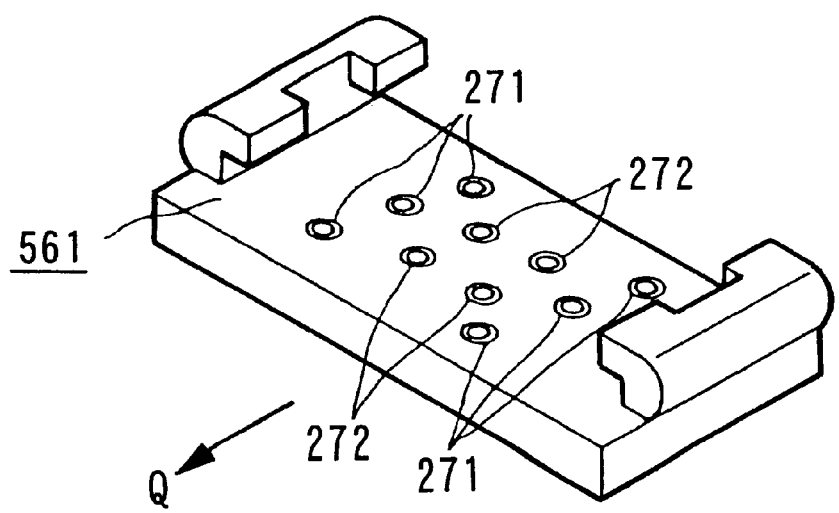

FIGS. 28(a) and 28(b) show the structure of connector cover 260. Connector cover 260 attaches to connector 500 when connector piece 230 is removed from the connector and the device is employed as an ordinary wristwatch. Openings 271,272 are formed to the bottom surface 261 of connector cover 260, corresponding to the positions at which the terminals 221,222 of connector 500 are disposed.

Figure 29A:
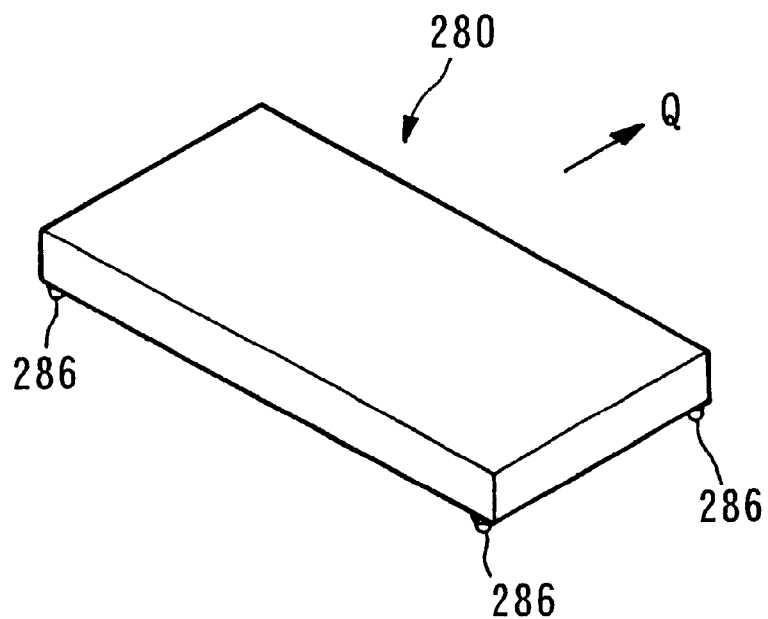
FIGS. 29(a) and 29(b) are perspective views of connector cover 280 which attaches to the wristwatch
Figure 29B:
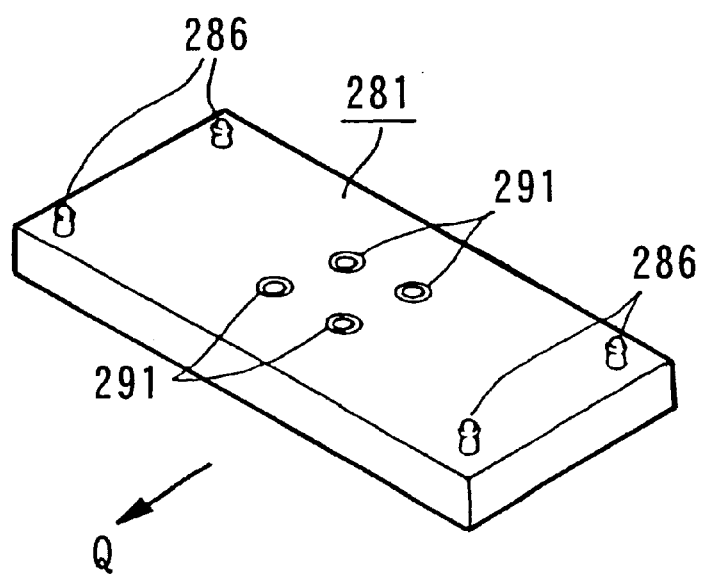

When only connector piece 230 is attached to connector 500, then a connector cover 280 as shown in FIGS. 29(a) and 29(b) are attached to protect terminals 561 provided in connector piece 230. Pins 286 are formed in the four corners of the bottom surface 281 of connector cover 280. These pins are designed to attach in openings 266 of connector piece 230, so that even during exercise, connector cover 280 does not detach from connector piece 230. Openings 291 are also provided in the bottom surface 281 of connector cover 280. These openings engage with terminals 561 of connector piece 230.

Figure 30A:
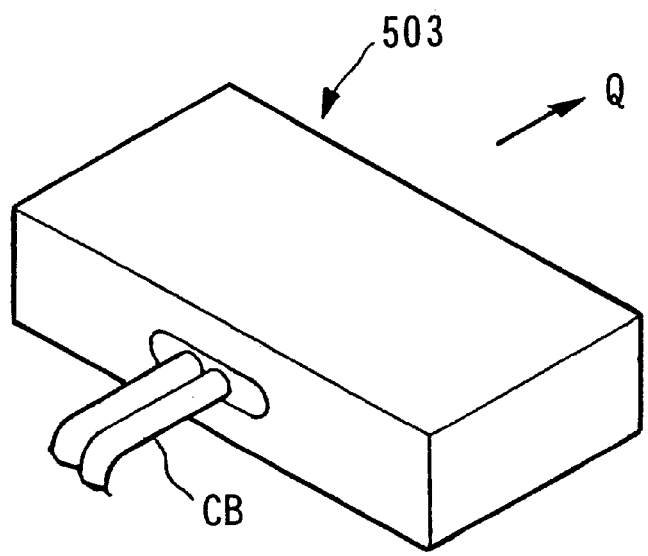
FIGS. 30(a) and 30(b) are perspective views of connector piece 503 which attaches to the wristwatch.
Figure 30B:
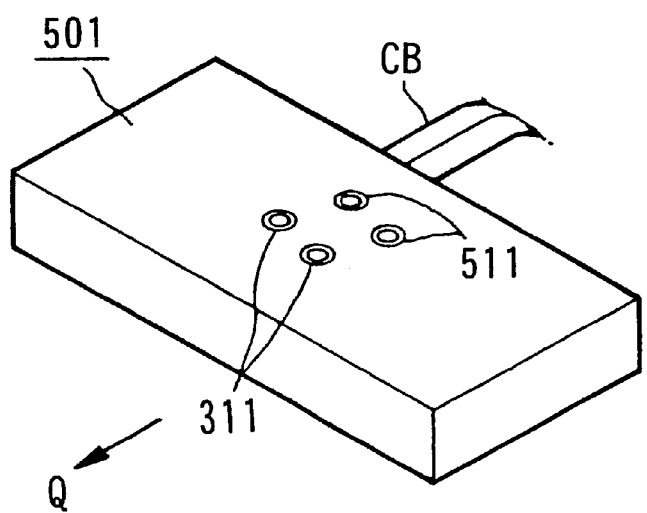

FIGS. 30(a) and 30(b) are perspective views of connector piece 503. Connector piece 503 is designed to be used by stacking on top of connector piece 230. As shown in the figure, cable CB is attached to connector piece 503. In addition, electrodes 511 are provided to the bottom surface 501 of connector piece 503. These electrodes are electrically connected to terminals 561 which are provided to connector piece 230. Additionally, as may be understood from the explanation of the preceding embodiments, is attached to connector piece 230 only when it is necessary to connect portable portion 70 and stationary portion 80.
Modification 6

In order to connect portable portion 70 and stationary portion 80, a variety of arrangements in addition to those described above may be considered. One example of these follows below.

Figure 31:
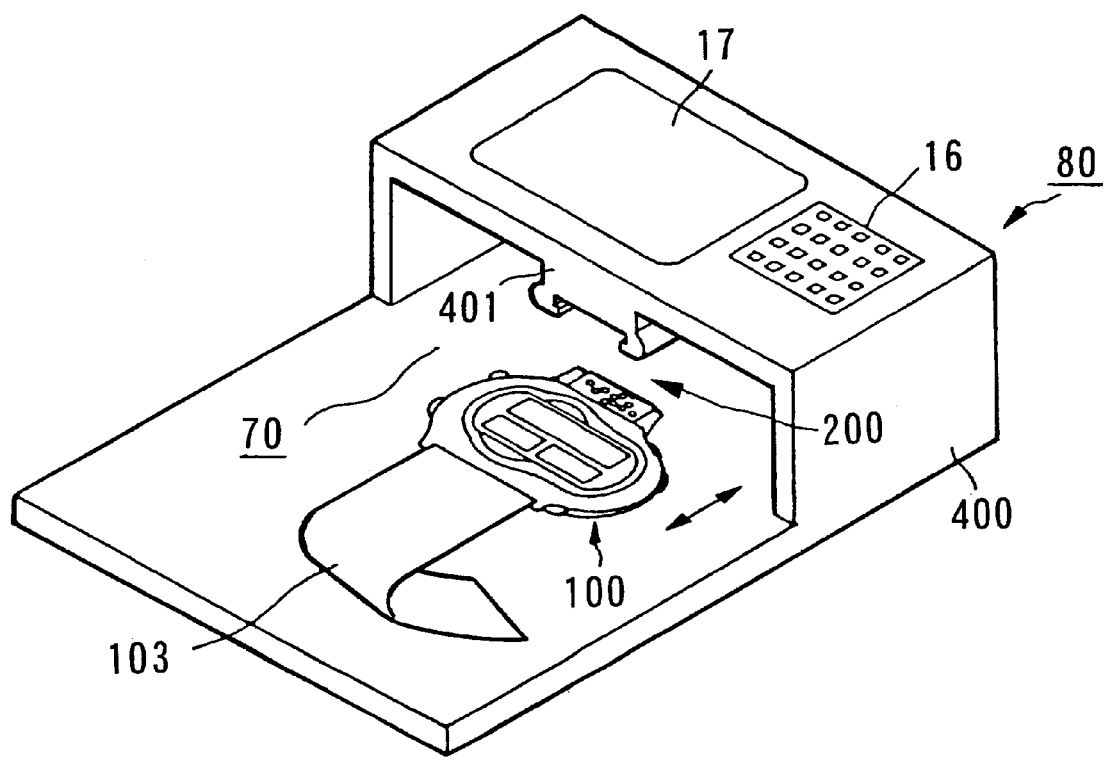
FIG. 31 is a view showing another embodiment for connecting portable portion 70 and stationary portion 80.
Figure 32:
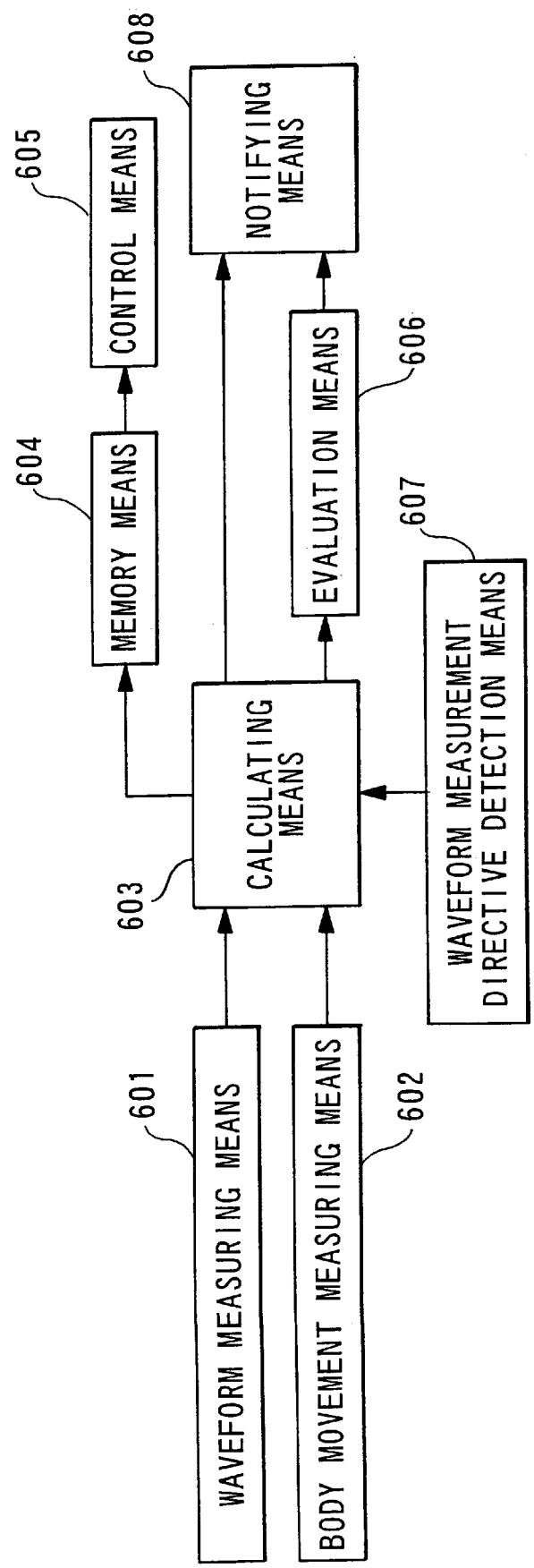
FIG. 32 shows an example of the structure of the present invention.

FIG. 31 shows the connection between portable portion 70 and stationary portion 80. Parts in this figure which are equivalent to those shown in FIGS. 19 through 30 have been assigned the same numeric symbol. FIG. 31 shows the case where cable 101 has been released from necklace 500, and band 103 is not attached to the terminal on connector 500.

In the figure, stationary portion 80 is housed in chassis 400, in place of the personal computer described above. A connector piece 401 is formed to chassis 400, and has a structure roughly equivalent to connector piece 230 shown in FIG. 27. The difference between these connector pieces is that connector piece 401 is not provided with electrode 251, terminals 561, and openings 266, since the connection of cable 101 is not necessary in the case of connector piece 401. Accordingly, a detailed explanation of connector piece 401 will be omitted.

The method for attaching and releasing connector 500 and connector piece 401 is the same as that employed in the case of connector 500 and connector piece 230. However, whereas connector piece 230 was gripped and attached to connector 500, here, connector 500 is attached to connector piece 401 by gripping the wristwatch.
Modification 7

Each of the preceding embodiments measured a patient's pulse rate, however, it is of course acceptable to measure heart rate.

Additionally, in the preceding embodiments and modifications, the user was notified of various information. However, it is also acceptable to notify a third party, in addition to the user. In this way, it is also possible for a third party to provide direction.

This arrangement can be realized as follows. Namely, as shown in FIG. 24, a portable portion 70 (or device main body 100) and a stationary portion 80 are connected using communications cable CB. All of the information displayed on liquid crystal display 108 inside portable portion 70 (or device main body 100) is relayed to stationary portion 80 via communications cable CB. Display device 17 in stationary portion 80 can then be made to display this information.

Additionally, keys corresponding to button switches 111–117 on portable portion 70 (device main body 100) may be provided to keyboard 16 on stationary portion 80. When these keys are manipulated, the information relating to which keys were pressed is relayed via communications cable CB, with the same processing carried out in portable portion 70 (or device main body 100) as performed when button switches 111–117 are operated.
Modification 8

In each of the preceding embodiments, it is also acceptable to design portable portion 70 and stationary portion 80 to convert physiological conditions such as the pulse wave to encoded information using character coding or the like, and then carry out bi-directional communications using this encoded information.

Namely, portable portion 70 uses one of the above-described methods to analyze pulse waveforms measured in the body, and determines whether the pulse wave type is normal, smooth or violent. This information is then encoded to a character code, for example, according to the type of pulse wave. The encoded information is then sent to stationary portion 80.

Stationary portion 80 recognizes whether the wave is a normal, smooth or violent wave based on the encoded information relayed to it. The pulse waveform corresponding to the waveform type recognized by stationary portion 80 is read out from a ROM or the like in stationary portion 80, and displayed on display device 17.

In addition to displaying the pulse waveform in this way, display device 17 may also be used to display the name corresponding to the classified waveform, i.e., normal, smooth, or violent, in letters. Alternatively, this information may be displayed using symbols or icons.

Further, if communication using compressed information is realized between portable portion 70 and stationary portion 80, then the amount of information to be relayed can be decreased. It should be noted that communication involving compressed information is equivalent to the case where information such as target values is relayed from stationary portion 80 to portable portion 70.
Modification 9

When setting the new exercise target in the preceding embodiments, it is also acceptable to compare the new exercise target value with the previous exercise target value, and notify the user of the difference between the two values. Additionally, in this case, a grade such as "higher", "unchanged" or "lower" may also be provided according to the results of this comparison.

Modification 10

In the previous embodiments, communication was carried out in both directions between portable portion 70 and stationary portion 80 via communications cable CB. However, the communications medium is not limited to a cable. Rather, wireless communication may also be employed by providing portable portion 70 and stationary portion 80 with a device for sending and receiving electric waves, light, ultrasonic waves, or the like.

What is claimed:

1. A health management device comprising:
   pulse wave measuring means for measuring a user's pulse waves;
   body movement measuring means for measuring said user's body movement;
   calculating means for obtaining an indicator showing the state of circulation in said user from said pulse waveform when the measured results of said body movement measuring means are below a prespecified value; and
   notifying means for notifying said user of said indicator.

2. A health management device according to claim 1, further comprising:
   pulse measuring means for measuring the heart rate or pulse rate of said user;
   wherein when the measured result of said body movement measuring means exceeds said prespecified value, said notifying means notifies said user of said measured pulse rate.

3. A health management device according to claim 1, further comprising:
   evaluation means for measuring an indicator when the measured result of said body movement measuring means is below said prespecified value, and measures the indicator again after the measured result of said body movement measuring means exceeds prespecified value and then again returns below said prespecified value, and then carries out an evaluation of the exercise performed by said user based on the difference in these indicators;
   wherein said notifying means notifies said user of the results of said exercise evaluation.

4. A health management device according to claim 1, wherein said notifying means provides notice of said indicator to a third party.

5. A health management device according to claim 1, wherein said calculating means obtains said pulse wave's acceleration pulse wave, selects two peaks and valleys from among the plurality of peaks and valleys appearing in said acceleration pulse wave, obtains an amplitude ratio for said selected peaks and valleys, and defines said ratio as the indicator.

6. A health management device according to claim 5, wherein said indicator is defined as the value obtained by dividing the amplitude value of the second valley by the amplitude value of the first peak in said acceleration pulse wave.

7. A health management device according to claim 1, wherein said calculating means calculates the time interval between adjacent pulse waves, carries out spectral analysis on the change over said time interval, and sets the amplitude value of the spectral component obtained from said spectral analysis as said indicator.

8. A health management device according to claim 1, wherein said calculating means calculates the time interval between adjacent pulse wave, conducts spectral analysis on the change over said time interval, calculates the ratio of the amplitudes of the low frequency and high frequency spectral components which are obtained from said spectral analysis, and sets said value as said indicator.

9. A health management device according to claim 1, wherein said calculating means calculates the time interval between adjacent pulse waves, and sets the number of times in which the amount of change in continuous said time intervals exceeds a prespecified time as said indicator.

10. A health management device according to claim 1, wherein the exercise to be performed by said user consists of a plurality of stages, said device further comprising:
    recording means in which target values for said indicator which are to be reached at each stage of exercise are prestored at each exercise stage; and
    comparing means for comparing the indicator calculated by said calculating means and said target value corresponding to each exercise stage, at the point in time when said user completes each exercise stage;
    wherein when the results of this comparison indicate that said indicator calculated by said calculating means has reached said target value, said notifying means notifies said user to proceed to the next stage of exercise.

11. A health management device according to claim 1, further comprising:
    recording means for recording said indicator obtained at prespecified times and the moving average for said indicators obtained over a past prespecified time interval; and
    control means for reading out from said recording means past indicators which were obtained at the same clock time as the present time, calculates the moving average of said past and current indicators, for storing the result in said recording means together with the current time, for determining the difference between said moving average of the indicators obtained over a past prespecified time interval and the current indicator, and for comparing this difference to a prespecified value;
    wherein if said difference exceeds the prespecified value, said notifying means provides a warning to said user.

12. A health management device comprising:
    a pulse wave measurer which measures a user's pulse waves;
    a body movement measurer which measures said user's body movement;
    a calculator which obtains an indicator showing the state of circulation in said user from said pulse waveform when the measured results of said body movement measurer are below a prespecified value; and
    a notifier which notifies said user of said indicator.

13. A health management device according to claim 12, further comprising:
    a pulse measurer which measures the heart rate or pulse rate of said user;
    wherein when the measured result of said body movement measurer exceeds said prespecified value, said notifier notifies said user of said measured pulse rate.

14. A health management device according to claim 12, further comprising:
    an evaluator which measures an indicator when the measured result of said body movement measurer is below said prespecified value, and measures the indicator again after the measured result of said body movement measurer exceeds said prespecified value and then again returns below said prespecified value, and then carries out an evaluation of the exercise performed by said user based on the difference in these indicators;

wherein said notifier notifies said user of the results of said exercise evaluation.

15. A health management device according to claim 12, wherein said notifier provides notice of said indicator to a third party.

16. A health management device according to claim 12, wherein said calculator obtains said pulse wave's acceleration pulse wave, selects two peaks and valleys from among the plurality of peaks and valleys appearing in said acceleration pulse wave, obtains an amplitude ratio for said selected peaks and valleys, and defines said ratio as the indicator.

17. A health management device according to claim 16, wherein said indicator is defined as the value obtained by dividing the amplitude value of the second valley by the amplitude value of the first peak in said acceleration pulse wave.

18. A health management device according to claim 12, wherein said calculator calculates the time interval between adjacent pulse waves, carries out spectral analysis on the change over said time interval, and sets the amplitude value of the spectral component obtained from said spectral analysis as said indicator.

19. A health management device according to claim 12, wherein said calculator calculates the time interval between adjacent pulse waves, and sets the number of times in which the amount of change in continuous said time intervals exceeds a prespecified time as said indicator.

20. A health management device according to claim 12, wherein the exercise to be performed by said user consists of a plurality of stages, said device further comprising:

a recorder in which target values for said indicator which are to be reached at each stage of exercise are prestored at each exercise stage; and a comparator which compares the indicator calculated by said calculator and said target value corresponding to each exercise stage, at the point in time when said user completes each exercise stage;

wherein when the results of this comparison indicate that said indicator calculated by said calculator has reached said target value, said notifier notifies said user to proceed to the next stage of exercise.

21. A health management device according to claim 12, further comprising:

a recorder which records said indicator obtained at prespecified times and the moving average for said indicators obtained over a past prespecified time interval; and a controller which reads out from said recorder past indicators which were obtained at the same clock time as the present time, calculates the moving average of said past and current indicators, stores this result in said recorder together with the current time, determines the difference between said moving average of the indicators obtained over a past prespecified time interval and the current indicator, and compares this difference to a prespecified value;

wherein if said difference exceeds the prespecified value, said notifier a warning to said user.

* * * * *